United States Patent
Arney et al.

(10) Patent No.: US 11,277,485 B2
(45) Date of Patent: Mar. 15, 2022

(54) MULTI-MODAL ACTIVITY TRACKING USER INTERFACE

(71) Applicant: Apple Inc., Cupertino, CA (US)

(72) Inventors: Julie A. Arney, Los Gatos, CA (US); Niharika Milind Bedekar, San Francisco, CA (US); Jay Blahnik, San Francisco, CA (US); Eamon F. Gilravi, San Francisco, CA (US); Brett L. Lareau, San Jose, CA (US); Danvin Ruangchan, San Jose, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 16/888,629

(22) Filed: May 29, 2020

(65) Prior Publication Data

US 2020/0382613 A1 Dec. 3, 2020

Related U.S. Application Data

(60) Provisional application No. 62/856,048, filed on Jun. 1, 2019.

(51) Int. Cl.
*H04L 29/08* (2006.01)
*H04L 67/50* (2022.01)
(Continued)

(52) U.S. Cl.
CPC ............ *H04L 67/22* (2013.01); *A61B 5/1118* (2013.01); *A61B 5/681* (2013.01); *G06F 1/163* (2013.01); *H04M 1/72463* (2021.01)

(58) Field of Classification Search
CPC ......... H04L 67/22; A61B 5/681; G06F 1/163; G06F 3/0482; G06F 3/0488; H04M 1/72463
See application file for complete search history.

(56) References Cited

U.S. PATENT DOCUMENTS

| | | | |
|---|---|---|---|
| 4,205,628 A | 6/1980 | Null | |
| 4,842,266 A | 6/1989 | Sweeney et al. | |
| (Continued) | | | |

FOREIGN PATENT DOCUMENTS

| | | |
|---|---|---|
| CA | 2815518 A1 | 5/2012 |
| CN | 1337638 A | 2/2002 |
| (Continued) | | |

OTHER PUBLICATIONS

Bagala et al., "Evaluation of Accelerometer-Based Fall Detection Algorithms on Real-World Falls", PloS ONE, vol. 7, No. 5, May 16, 2012, 9 pages.
(Continued)

*Primary Examiner* — Dino Kujundzic
(74) *Attorney, Agent, or Firm* — Dentons US LLP

(57) ABSTRACT

The present disclosure generally relates to user interfaces and techniques for monitoring fitness activity. In accordance with some embodiments, user interfaces and techniques for transitioning between a user interface mode for measuring an activity metric to a user interface mode for measuring a different activity, based on detecting that a user characteristic has changed, are described. In accordance with some embodiments, user interfaces and techniques for measuring activity data and providing activity commentary in response to activity-based events, where different activity commentary is provided based on a characteristic of a user, are described.

21 Claims, 37 Drawing Sheets

(51) Int. Cl.
  *A61B 5/11* (2006.01)
  *A61B 5/00* (2006.01)
  *G06F 1/16* (2006.01)
  *H04M 1/72463* (2021.01)

(56) References Cited

U.S. PATENT DOCUMENTS

| | | | |
|---|---|---|---|
| 5,423,863 A | 6/1995 | Felblinger et al. | |
| 5,458,548 A * | 10/1995 | Crossing | A63B 24/00 |
| | | | 482/6 |
| 5,474,077 A * | 12/1995 | Suga | A61B 5/222 |
| | | | 600/500 |
| 5,685,723 A | 11/1997 | Ladin et al. | |
| 5,788,655 A | 8/1998 | Yoshimura et al. | |
| 6,013,008 A | 1/2000 | Fukushima | |
| 6,095,949 A | 8/2000 | Arai | |
| 6,095,984 A | 8/2000 | Amano et al. | |
| 6,097,371 A | 8/2000 | Siddiqui et al. | |
| 6,097,385 A * | 8/2000 | Robinson | G06F 21/6218 |
| | | | 715/718 |
| 6,244,988 B1 | 6/2001 | Delman | |
| 6,302,789 B2 * | 10/2001 | Harada | G01C 22/006 |
| | | | 463/7 |
| 6,416,471 B1 | 7/2002 | Kumar et al. | |
| 6,603,477 B1 | 8/2003 | Tittle | |
| 6,639,584 B1 | 10/2003 | Li | |
| 6,705,972 B1 | 3/2004 | Takano et al. | |
| 6,837,827 B1 | 1/2005 | Lee | |
| 6,866,613 B1 | 3/2005 | Brown et al. | |
| 7,128,693 B2 | 10/2006 | Brown et al. | |
| 7,251,454 B2 | 7/2007 | White | |
| 7,302,272 B2 * | 11/2007 | Ackley | H04M 3/436 |
| | | | 455/466 |
| 7,662,065 B1 | 2/2010 | Kahn | |
| 7,739,148 B2 | 6/2010 | Suzuki et al. | |
| 8,060,229 B2 | 11/2011 | Gupta et al. | |
| 8,105,208 B2 | 1/2012 | Oleson et al. | |
| 8,321,006 B1 | 11/2012 | Snyder et al. | |
| 8,341,557 B2 | 12/2012 | Pisula et al. | |
| 8,475,339 B2 | 7/2013 | Hwang et al. | |
| 8,496,563 B2 | 7/2013 | Komatsu et al. | |
| 8,676,170 B2 | 3/2014 | Porrati et al. | |
| 8,784,115 B1 | 7/2014 | Chuang | |
| 8,825,445 B2 | 9/2014 | Hoffman et al. | |
| 8,934,963 B1 | 1/2015 | Farazi | |
| 8,990,006 B1 | 3/2015 | Wallace et al. | |
| 9,020,538 B1 | 4/2015 | White et al. | |
| 9,224,291 B2 | 12/2015 | Moll-carrillo et al. | |
| 9,230,076 B2 * | 1/2016 | King | G06F 21/53 |
| 9,557,881 B1 | 1/2017 | Jain et al. | |
| 9,589,445 B2 | 3/2017 | White et al. | |
| 9,712,629 B2 | 7/2017 | Molettiere et al. | |
| 9,734,477 B2 | 8/2017 | Weast et al. | |
| 9,813,642 B1 | 11/2017 | Chen et al. | |
| 9,817,481 B2 | 11/2017 | Pantelopoulos et al. | |
| 9,854,653 B1 | 12/2017 | Ackmann et al. | |
| 9,880,805 B1 | 1/2018 | Guralnick | |
| 9,940,682 B2 | 4/2018 | Hoffman et al. | |
| 10,056,006 B1 | 8/2018 | Hsu-hoffman et al. | |
| 10,220,258 B2 | 3/2019 | Gu et al. | |
| 10,300,334 B1 | 5/2019 | Chuang | |
| 10,304,347 B2 | 5/2019 | Wilson et al. | |
| 10,339,830 B2 | 7/2019 | Han et al. | |
| 10,398,381 B1 | 9/2019 | Heneghan et al. | |
| 10,489,508 B2 | 11/2019 | Zhai et al. | |
| 10,777,314 B1 | 9/2020 | Williams et al. | |
| 11,107,569 B1 * | 8/2021 | Devoto | G16H 40/67 |
| 2001/0049470 A1 | 12/2001 | Mault et al. | |
| 2002/0045960 A1 | 4/2002 | Phillips et al. | |
| 2002/0086774 A1 | 7/2002 | Warner | |
| 2002/0118121 A1 | 8/2002 | Lehrman et al. | |
| 2003/0023178 A1 | 1/2003 | Bischoff et al. | |
| 2003/0064860 A1 | 4/2003 | Yamashita et al. | |
| 2003/0134714 A1 | 7/2003 | Oishi et al. | |
| 2003/0179229 A1 * | 9/2003 | Van Erlach | H04M 1/724 |
| | | | 715/744 |
| 2003/0182628 A1 | 9/2003 | Lira | |
| 2003/0216971 A1 | 11/2003 | Sick et al. | |
| 2003/0226695 A1 | 12/2003 | Mault | |
| 2004/0014567 A1 | 1/2004 | Mendel | |
| 2004/0077462 A1 | 4/2004 | Brown et al. | |
| 2004/0128286 A1 | 7/2004 | Yasushi et al. | |
| 2005/0075214 A1 | 4/2005 | Brown et al. | |
| 2005/0079905 A1 | 4/2005 | Martens | |
| 2005/0113650 A1 | 5/2005 | Pacione et al. | |
| 2005/0124324 A1 | 6/2005 | Thomas et al. | |
| 2005/0139852 A1 | 6/2005 | Chen et al. | |
| 2005/0172311 A1 | 8/2005 | Hjelt et al. | |
| 2005/0197063 A1 | 9/2005 | White et al. | |
| 2005/0216867 A1 | 9/2005 | Marvit et al. | |
| 2005/0228735 A1 | 10/2005 | Duquette | |
| 2005/0272564 A1 | 12/2005 | Pyles et al. | |
| 2006/0020174 A1 | 1/2006 | Matsumura et al. | |
| 2006/0052727 A1 | 3/2006 | Palestrant | |
| 2006/0098109 A1 | 5/2006 | Ooki | |
| 2006/0106741 A1 | 5/2006 | Janarthanan | |
| 2006/0184800 A1 * | 8/2006 | Rosenberg | G07C 9/37 |
| | | | 713/186 |
| 2006/0240959 A1 | 10/2006 | Huang | |
| 2006/0250524 A1 | 11/2006 | Roche | |
| 2007/0021269 A1 | 1/2007 | Shum | |
| 2007/0032733 A1 | 2/2007 | Burton | |
| 2007/0033069 A1 | 2/2007 | Rao et al. | |
| 2007/0056727 A1 | 3/2007 | Newman | |
| 2007/0071256 A1 | 3/2007 | Ito | |
| 2007/0113726 A1 | 5/2007 | Oliver et al. | |
| 2007/0136093 A1 | 6/2007 | Rankin et al. | |
| 2007/0143433 A1 | 6/2007 | Daigle | |
| 2007/0169614 A1 | 7/2007 | Sasaki et al. | |
| 2007/0249949 A1 | 10/2007 | Hadley | |
| 2007/0271065 A1 | 11/2007 | Gupta et al. | |
| 2008/0020803 A1 * | 1/2008 | Rios | H04M 1/72448 |
| | | | 455/565 |
| 2008/0027673 A1 * | 1/2008 | Trumm | A63F 13/28 |
| | | | 702/160 |
| 2008/0051919 A1 | 2/2008 | Sakai et al. | |
| 2008/0052945 A1 | 3/2008 | Matas et al. | |
| 2008/0058626 A1 | 3/2008 | Miyata et al. | |
| 2008/0076637 A1 | 3/2008 | Gilley et al. | |
| 2008/0082145 A1 | 4/2008 | Skwarek et al. | |
| 2008/0086318 A1 | 4/2008 | Gilley et al. | |
| 2008/0096726 A1 | 4/2008 | Riley et al. | |
| 2008/0141135 A1 | 6/2008 | Mason et al. | |
| 2008/0150731 A1 | 6/2008 | Laukkanen et al. | |
| 2008/0161707 A1 | 7/2008 | Farringdon et al. | |
| 2008/0200312 A1 | 8/2008 | Tagliabue | |
| 2008/0229226 A1 | 9/2008 | Rowbottom et al. | |
| 2008/0254767 A1 * | 10/2008 | Jin | H04M 1/667 |
| | | | 455/411 |
| 2008/0300110 A1 | 12/2008 | Smith et al. | |
| 2009/0012988 A1 | 1/2009 | Brown | |
| 2009/0118100 A1 | 5/2009 | Oliver et al. | |
| 2009/0164567 A1 | 6/2009 | Hara | |
| 2009/0170532 A1 * | 7/2009 | Lee | H04M 1/72457 |
| | | | 455/456.3 |
| 2009/0192823 A1 | 7/2009 | Hawkins et al. | |
| 2009/0210078 A1 | 8/2009 | Crowley | |
| 2009/0216556 A1 | 8/2009 | Martin et al. | |
| 2009/0222056 A1 | 9/2009 | Lindh et al. | |
| 2009/0233771 A1 | 9/2009 | Quatrochi et al. | |
| 2009/0262088 A1 | 10/2009 | Moll-carrillo et al. | |
| 2009/0287103 A1 | 11/2009 | Pillai | |
| 2009/0319243 A1 | 12/2009 | Suarez-rivera et al. | |
| 2010/0031202 A1 | 2/2010 | Morris et al. | |
| 2010/0042949 A1 | 2/2010 | Chen | |
| 2010/0048358 A1 | 2/2010 | Tchao et al. | |
| 2010/0060586 A1 | 3/2010 | Pisula et al. | |
| 2010/0062818 A1 | 3/2010 | Haughay et al. | |
| 2010/0062905 A1 | 3/2010 | Rottler et al. | |
| 2010/0064255 A1 | 3/2010 | Rottler et al. | |
| 2010/0076331 A1 | 3/2010 | Chan et al. | |
| 2010/0079291 A1 | 4/2010 | Kroll et al. | |
| 2010/0121700 A1 | 5/2010 | Wigder et al. | |

(56) References Cited

U.S. PATENT DOCUMENTS

| | | |
|---|---|---|
| 2010/0145209 A1 | 6/2010 | Lee et al. |
| 2010/0179832 A1 | 7/2010 | Van et al. |
| 2010/0194692 A1 | 8/2010 | Orr et al. |
| 2010/0198453 A1 | 8/2010 | Dorogusker et al. |
| 2010/0281374 A1 | 11/2010 | Schulz et al. |
| 2010/0292600 A1 | 11/2010 | Dibenedetto et al. |
| 2010/0298899 A1 | 11/2010 | Donnelly et al. |
| 2010/0305965 A1 | 12/2010 | Benjamin et al. |
| 2010/0331145 A1 | 12/2010 | Lakovic et al. |
| 2011/0003665 A1 | 1/2011 | Burton et al. |
| 2011/0016120 A1 | 1/2011 | Haughay et al. |
| 2011/0032105 A1 | 2/2011 | Hoffman et al. |
| 2011/0066051 A1 | 3/2011 | Moon et al. |
| 2011/0071869 A1 | 3/2011 | O'Brien et al. |
| 2011/0074699 A1 | 3/2011 | Marr et al. |
| 2011/0098928 A1 | 4/2011 | Hoffman et al. |
| 2011/0106553 A1 | 5/2011 | Tanaka et al. |
| 2011/0112418 A1 | 5/2011 | Feild et al. |
| 2011/0125041 A1 | 5/2011 | Fischell et al. |
| 2011/0137678 A1 | 6/2011 | Williams |
| 2011/0137836 A1 | 6/2011 | Kuriyama et al. |
| 2011/0159469 A1 | 6/2011 | Hwang et al. |
| 2011/0167369 A1 | 7/2011 | Van |
| 2011/0201911 A1 | 8/2011 | Johnson et al. |
| 2011/0213276 A1 | 9/2011 | Sarussi et al. |
| 2011/0227872 A1 | 9/2011 | Huska et al. |
| 2011/0230169 A1 | 9/2011 | Ohki |
| 2011/0230986 A1 | 9/2011 | Lafortune et al. |
| 2011/0246509 A1 | 10/2011 | Migita et al. |
| 2011/0261079 A1 | 10/2011 | Ingrassia et al. |
| 2011/0275940 A1 | 11/2011 | Nims et al. |
| 2011/0306389 A1 | 12/2011 | Nagayama |
| 2011/0307821 A1 | 12/2011 | Martens |
| 2012/0015778 A1 | 1/2012 | Lee et al. |
| 2012/0015779 A1 | 1/2012 | Powch et al. |
| 2012/0030623 A1 | 2/2012 | Hoellwarth |
| 2012/0034897 A1 | 2/2012 | Kreitzer et al. |
| 2012/0041767 A1 | 2/2012 | Hoffman et al. |
| 2012/0042039 A1 | 2/2012 | Mark |
| 2012/0059664 A1 | 3/2012 | Georgiev et al. |
| 2012/0071770 A1 | 3/2012 | Grey et al. |
| 2012/0092383 A1 | 4/2012 | Hysek et al. |
| 2012/0105225 A1 | 5/2012 | Valtonen |
| 2012/0116550 A1 | 5/2012 | Hoffman et al. |
| 2012/0179319 A1 | 7/2012 | Gilman et al. |
| 2012/0232414 A1 | 9/2012 | Mollicone et al. |
| 2012/0253485 A1 | 10/2012 | Weast et al. |
| 2012/0274508 A1 | 11/2012 | Brown et al. |
| 2012/0283855 A1 | 11/2012 | Hoffman et al. |
| 2012/0290109 A1 | 11/2012 | Engelberg et al. |
| 2012/0302840 A1 | 11/2012 | Kubo |
| 2012/0317167 A1 | 12/2012 | Rahman et al. |
| 2012/0326873 A1 | 12/2012 | Utter, II |
| 2013/0054150 A1 | 2/2013 | Sacks et al. |
| 2013/0054720 A1 | 2/2013 | Kang et al. |
| 2013/0067050 A1 | 3/2013 | Kotteri et al. |
| 2013/0081083 A1 | 3/2013 | Yu et al. |
| 2013/0093715 A1 | 4/2013 | Marsden et al. |
| 2013/0106603 A1 | 5/2013 | Weast et al. |
| 2013/0106684 A1 | 5/2013 | Weast et al. |
| 2013/0110264 A1 | 5/2013 | Weast et al. |
| 2013/0115583 A1 | 5/2013 | Gordon et al. |
| 2013/0132028 A1 | 5/2013 | Crankson et al. |
| 2013/0137073 A1 | 5/2013 | Nacey et al. |
| 2013/0138734 A1 | 5/2013 | Crivello et al. |
| 2013/0141233 A1 | 6/2013 | Jacobs et al. |
| 2013/0151285 A1 | 6/2013 | Mclaren et al. |
| 2013/0158367 A1 | 6/2013 | Pacione et al. |
| 2013/0184613 A1 | 7/2013 | Homsi et al. |
| 2013/0187923 A1 | 7/2013 | Yoshimoto et al. |
| 2013/0188322 A1 | 7/2013 | Lowe et al. |
| 2013/0197679 A1 | 8/2013 | Balakrishnan et al. |
| 2013/0198672 A1 | 8/2013 | Yoon et al. |
| 2013/0203475 A1 | 8/2013 | Shin et al. |
| 2013/0215119 A1 | 8/2013 | Vanhoecke |
| 2013/0217979 A1 | 8/2013 | Blackadar et al. |
| 2013/0231575 A1 | 9/2013 | Erkkila et al. |
| 2013/0231711 A1 | 9/2013 | Kaib |
| 2013/0233097 A1 | 9/2013 | Hayner et al. |
| 2013/0262155 A1 | 10/2013 | Hinkamp |
| 2013/0263719 A1 | 10/2013 | Watterson et al. |
| 2013/0325358 A1* | 12/2013 | Oshima ................ G01C 22/006 702/19 |
| 2013/0325394 A1 | 12/2013 | Yuen et al. |
| 2013/0325396 A1 | 12/2013 | Yuen et al. |
| 2013/0330694 A1 | 12/2013 | Watterson |
| 2013/0332286 A1 | 12/2013 | Medelius et al. |
| 2013/0345978 A1 | 12/2013 | Lush et al. |
| 2014/0037107 A1 | 2/2014 | Marino et al. |
| 2014/0038781 A1 | 2/2014 | Foley et al. |
| 2014/0067096 A1 | 3/2014 | Aibara |
| 2014/0081666 A1 | 3/2014 | Teller et al. |
| 2014/0108998 A1 | 4/2014 | Chaudhri et al. |
| 2014/0139637 A1 | 5/2014 | Mistry et al. |
| 2014/0176346 A1 | 6/2014 | Brumback et al. |
| 2014/0176475 A1 | 6/2014 | Myers et al. |
| 2014/0189584 A1 | 7/2014 | Weng et al. |
| 2014/0200691 A1 | 7/2014 | Lee et al. |
| 2014/0218369 A1 | 8/2014 | Yuen et al. |
| 2014/0228647 A1 | 8/2014 | Sakamoto et al. |
| 2014/0239065 A1 | 8/2014 | Zhou et al. |
| 2014/0240122 A1 | 8/2014 | Roberts et al. |
| 2014/0240349 A1 | 8/2014 | Tuukkanen |
| 2014/0244009 A1 | 8/2014 | Mestas |
| 2014/0245161 A1 | 8/2014 | Yuen et al. |
| 2014/0257537 A1 | 9/2014 | Stroupe et al. |
| 2014/0275852 A1 | 9/2014 | Hong et al. |
| 2014/0275854 A1 | 9/2014 | Venkatraman et al. |
| 2014/0277628 A1 | 9/2014 | Nieminen et al. |
| 2014/0278229 A1 | 9/2014 | Hong et al. |
| 2014/0282153 A1 | 9/2014 | Christiansen et al. |
| 2014/0288680 A1 | 9/2014 | Hoffman et al. |
| 2014/0310598 A1 | 10/2014 | Sprague et al. |
| 2014/0310643 A1 | 10/2014 | Karmanenko et al. |
| 2014/0331314 A1* | 11/2014 | Fujioka .................. G06F 21/10 726/17 |
| 2014/0336796 A1 | 11/2014 | Agnew |
| 2014/0337450 A1 | 11/2014 | Choudhary et al. |
| 2014/0337451 A1 | 11/2014 | Choudhary et al. |
| 2014/0344723 A1 | 11/2014 | Malik et al. |
| 2014/0344951 A1 | 11/2014 | Brewer |
| 2014/0371887 A1 | 12/2014 | Hoffman et al. |
| 2015/0004578 A1 | 1/2015 | Gilley et al. |
| 2015/0018632 A1 | 1/2015 | Khair |
| 2015/0046814 A1 | 2/2015 | Haughay et al. |
| 2015/0057943 A1 | 2/2015 | Self et al. |
| 2015/0065302 A1 | 3/2015 | Ou et al. |
| 2015/0067513 A1 | 3/2015 | Zambetti et al. |
| 2015/0067811 A1 | 3/2015 | Agnew et al. |
| 2015/0074571 A1 | 3/2015 | Marti et al. |
| 2015/0081059 A1 | 3/2015 | Hwang et al. |
| 2015/0083970 A1 | 3/2015 | Koh et al. |
| 2015/0098309 A1 | 4/2015 | Adams et al. |
| 2015/0100245 A1 | 4/2015 | Huang et al. |
| 2015/0106025 A1 | 4/2015 | Keller et al. |
| 2015/0112700 A1 | 4/2015 | Sublett et al. |
| 2015/0113553 A1 | 4/2015 | Pan |
| 2015/0118657 A1 | 4/2015 | Shrake et al. |
| 2015/0130830 A1 | 5/2015 | Nagasaki et al. |
| 2015/0142689 A1* | 5/2015 | Squires .................. G01C 22/00 705/329 |
| 2015/0153943 A1 | 6/2015 | Wang |
| 2015/0180746 A1* | 6/2015 | Day, II .................. H04L 51/16 455/405 |
| 2015/0181314 A1 | 6/2015 | Swanson |
| 2015/0185967 A1 | 7/2015 | Ly et al. |
| 2015/0193805 A1 | 7/2015 | Filipiak |
| 2015/0196804 A1 | 7/2015 | Koduri et al. |
| 2015/0199494 A1 | 7/2015 | Koduri et al. |
| 2015/0205492 A1 | 7/2015 | Nobil |
| 2015/0205930 A1 | 7/2015 | Shaanan et al. |
| 2015/0217163 A1 | 8/2015 | Amis et al. |
| 2015/0220883 A1 | 8/2015 | Bfar et al. |
| 2015/0269848 A1 | 9/2015 | Yuen et al. |

(56) References Cited

U.S. PATENT DOCUMENTS

| | | |
|---|---|---|
| 2015/0293592 A1 | 10/2015 | Cheong et al. |
| 2015/0297134 A1 | 10/2015 | Albert et al. |
| 2015/0301691 A1 | 10/2015 | Qin |
| 2015/0324751 A1 | 11/2015 | Orenstein et al. |
| 2015/0331589 A1 | 11/2015 | Kawakita |
| 2015/0347711 A1 | 12/2015 | Soli et al. |
| 2015/0374310 A1 | 12/2015 | Lee |
| 2016/0015275 A1 | 1/2016 | Samadani et al. |
| 2016/0019360 A1 | 1/2016 | Pahwa et al. |
| 2016/0027282 A1 | 1/2016 | Lee |
| 2016/0048298 A1 | 2/2016 | Choi et al. |
| 2016/0058336 A1 | 3/2016 | Blahnik et al. |
| 2016/0058337 A1 | 3/2016 | Blahnik et al. |
| 2016/0062582 A1 | 3/2016 | Wilson et al. |
| 2016/0065505 A1 | 3/2016 | Iskander |
| 2016/0070275 A1 | 3/2016 | Anderson et al. |
| 2016/0072896 A1 | 3/2016 | Petersen et al. |
| 2016/0085937 A1 | 3/2016 | Dertinger et al. |
| 2016/0107031 A1 | 4/2016 | Palatsi et al. |
| 2016/0135731 A1 | 5/2016 | Drennan |
| 2016/0140828 A1 | 5/2016 | Deforest |
| 2016/0156584 A1 | 6/2016 | Hum et al. |
| 2016/0196635 A1 | 7/2016 | Cho et al. |
| 2016/0210099 A1 | 7/2016 | Hampapuram et al. |
| 2016/0220225 A1 | 8/2016 | Wang et al. |
| 2016/0235374 A1 | 8/2016 | Miller et al. |
| 2016/0250517 A1 | 9/2016 | Tilvis et al. |
| 2016/0256082 A1 | 9/2016 | Ely et al. |
| 2016/0256741 A1 | 9/2016 | Holma et al. |
| 2016/0263435 A1 | 9/2016 | Venkatraman et al. |
| 2016/0278659 A1 | 9/2016 | Kaib et al. |
| 2016/0278667 A1 | 9/2016 | Villard et al. |
| 2016/0279475 A1 | 9/2016 | Aragones et al. |
| 2016/0301794 A1 | 10/2016 | Schlakman et al. |
| 2016/0324457 A1 | 11/2016 | Dagum |
| 2016/0328736 A1 | 11/2016 | Wang et al. |
| 2016/0332025 A1 | 11/2016 | Repka |
| 2016/0346607 A1 | 12/2016 | Rapfogel |
| 2016/0371464 A1 | 12/2016 | Bricker |
| 2016/0375306 A1 | 12/2016 | Gu et al. |
| 2016/0379511 A1 | 12/2016 | Dawson et al. |
| 2017/0001073 A1 | 1/2017 | Krueger et al. |
| 2017/0011210 A1* | 1/2017 | Cheong ................. H04W 4/00 |
| 2017/0014037 A1 | 1/2017 | Coppola et al. |
| 2017/0021184 A1 | 1/2017 | Pavel et al. |
| 2017/0024399 A1 | 1/2017 | Boyle et al. |
| 2017/0024539 A1 | 1/2017 | Webb et al. |
| 2017/0032168 A1 | 2/2017 | Kim |
| 2017/0053542 A1 | 2/2017 | Wilson et al. |
| 2017/0065224 A1 | 3/2017 | Rahko et al. |
| 2017/0095695 A1 | 4/2017 | Mangusson et al. |
| 2017/0143262 A1 | 5/2017 | Kurunmäki et al. |
| 2017/0153606 A1 | 6/2017 | Pitis et al. |
| 2017/0153804 A1 | 6/2017 | Kim et al. |
| 2017/0161014 A1 | 6/2017 | Kikugawa et al. |
| 2017/0209766 A1 | 7/2017 | Riley et al. |
| 2017/0237694 A1 | 8/2017 | Choudhary et al. |
| 2017/0239524 A1 | 8/2017 | Lee et al. |
| 2017/0243508 A1 | 8/2017 | Cheng et al. |
| 2017/0266494 A1 | 9/2017 | Crankson et al. |
| 2017/0269792 A1 | 9/2017 | Xu et al. |
| 2017/0274149 A1 | 9/2017 | Aeschlimann |
| 2017/0274267 A1 | 9/2017 | Blahnik |
| 2017/0281026 A1 | 10/2017 | Nick et al. |
| 2017/0281057 A1 | 10/2017 | Blahnik et al. |
| 2017/0294174 A1 | 10/2017 | Albadawi et al. |
| 2017/0300186 A1 | 10/2017 | Kuhar et al. |
| 2017/0319941 A1 | 11/2017 | Smith et al. |
| 2017/0330297 A1 | 11/2017 | Cronin et al. |
| 2017/0333752 A1 | 11/2017 | Korkala et al. |
| 2017/0348562 A1 | 12/2017 | Jung et al. |
| 2017/0354845 A1 | 12/2017 | Williams et al. |
| 2017/0357520 A1 | 12/2017 | De Vries et al. |
| 2018/0000426 A1 | 1/2018 | Li |
| 2018/0001184 A1 | 1/2018 | Tran et al. |
| 2018/0053200 A1 | 2/2018 | Cronin et al. |
| 2018/0056132 A1 | 3/2018 | Foley et al. |
| 2018/0065025 A1 | 3/2018 | Toda et al. |
| 2018/0074462 A1 | 3/2018 | Helder et al. |
| 2018/0074464 A1 | 3/2018 | Essery et al. |
| 2018/0078182 A1 | 3/2018 | Chen et al. |
| 2018/0126248 A1 | 5/2018 | Dion et al. |
| 2018/0137937 A1 | 5/2018 | Gass et al. |
| 2018/0140903 A1 | 5/2018 | Poure et al. |
| 2018/0150709 A1 | 5/2018 | Ha |
| 2018/0189077 A1 | 7/2018 | Gupta et al. |
| 2018/0206766 A1 | 7/2018 | Blahnik et al. |
| 2018/0272190 A1 | 9/2018 | Miura et al. |
| 2018/0294053 A1 | 10/2018 | Runyon et al. |
| 2018/0318647 A1 | 11/2018 | Foley et al. |
| 2018/0329584 A1 | 11/2018 | Williams et al. |
| 2018/0339195 A1 | 11/2018 | Bernotas |
| 2018/0345078 A1 | 12/2018 | Blahnik et al. |
| 2019/0008467 A1 | 1/2019 | Averina et al. |
| 2019/0025995 A1 | 1/2019 | Williams |
| 2019/0034049 A1 | 1/2019 | Williams et al. |
| 2019/0034050 A1 | 1/2019 | Williams et al. |
| 2019/0104951 A1 | 4/2019 | Valys et al. |
| 2019/0184234 A1 | 6/2019 | Packles et al. |
| 2019/0209777 A1 | 7/2019 | O'connell et al. |
| 2019/0232110 A1 | 8/2019 | Williams et al. |
| 2019/0232111 A1 | 8/2019 | Williams et al. |
| 2019/0274565 A1 | 9/2019 | Soli et al. |
| 2019/0279520 A1 | 9/2019 | Wilson et al. |
| 2019/0336044 A1 | 11/2019 | Williams et al. |
| 2019/0336045 A1 | 11/2019 | Williams et al. |
| 2019/0336827 A1 | 11/2019 | Intonate et al. |
| 2019/0339849 A1 | 11/2019 | Williams et al. |
| 2019/0342616 A1 | 11/2019 | Domm et al. |
| 2019/0387982 A1 | 12/2019 | Buller |
| 2020/0014967 A1 | 1/2020 | Putnam |
| 2020/0101365 A1 | 4/2020 | Wilson et al. |
| 2020/0297249 A1 | 9/2020 | Williams et al. |
| 2020/0357522 A1 | 11/2020 | Pahwa et al. |
| 2020/0381100 A1 | 12/2020 | Williams et al. |
| 2021/0007632 A1 | 1/2021 | Blahnik et al. |
| 2021/0007633 A1 | 1/2021 | Blahnik et al. |
| 2021/0110908 A1 | 4/2021 | Blahnik et al. |
| 2021/0113116 A1 | 4/2021 | Chen et al. |
| 2021/0145321 A1 | 5/2021 | Chen et al. |
| 2021/0191584 A1 | 6/2021 | Williams et al. |
| 2021/0193293 A1 | 6/2021 | Blahnik et al. |
| 2021/0252337 A1 | 8/2021 | Devine et al. |
| 2021/0252341 A1 | 8/2021 | Devine et al. |
| 2021/0252369 A1 | 8/2021 | Devine et al. |
| 2021/0255747 A1 | 8/2021 | Devine et al. |
| 2021/0255758 A1 | 8/2021 | Devine et al. |
| 2021/0255826 A1 | 8/2021 | Devine et al. |

FOREIGN PATENT DOCUMENTS

| | | |
|---|---|---|
| CN | 1397904 A | 2/2003 |
| CN | 1585943 A | 2/2005 |
| CN | 101150810 A | 3/2008 |
| CN | 101541387 A | 9/2009 |
| CN | 101651870 A | 2/2010 |
| CN | 101836894 A | 9/2010 |
| CN | 101978374 A | 2/2011 |
| CN | 102339201 A | 2/2012 |
| CN | 102448555 A | 5/2012 |
| CN | 102804238 A | 11/2012 |
| CN | 102989159 A | 3/2013 |
| CN | 103212197 A | 7/2013 |
| CN | 103370924 A | 10/2013 |
| CN | 103403627 A | 11/2013 |
| CN | 104288983 A | 1/2015 |
| CN | 104501043 A | 4/2015 |
| CN | 104508426 A | 4/2015 |
| CN | 106537397 A | 3/2017 |
| CN | 106709235 A | 5/2017 |
| CN | 106878550 A | 6/2017 |
| EP | 1935339 A1 | 6/2008 |
| EP | 2025368 A2 | 2/2009 |
| EP | 3122038 A1 | 1/2017 |

(56) References Cited

FOREIGN PATENT DOCUMENTS

| | | |
|---|---|---|
| JP | 6-187118 A | 7/1994 |
| JP | 2001-76078 A | 3/2001 |
| JP | 2002-190007 A | 7/2002 |
| JP | 2003-337863 A | 11/2003 |
| JP | 2004-102609 A | 4/2004 |
| JP | 2004-113466 A | 4/2004 |
| JP | 2005-79814 A | 3/2005 |
| JP | 2006-230679 A | 9/2006 |
| JP | 2007-260288 A | 10/2007 |
| JP | 2007-330513 A | 12/2007 |
| JP | 2008-104758 A | 5/2008 |
| JP | 2008-183339 A | 8/2008 |
| JP | 2009-78134 A | 4/2009 |
| JP | 2010-12335 A | 1/2010 |
| JP | 2010-517725 A | 5/2010 |
| JP | 2010-122901 A | 6/2010 |
| JP | 2010-162297 A | 7/2010 |
| JP | 2010-181280 A | 8/2010 |
| JP | 2011-125633 A | 6/2011 |
| JP | 2011-183101 A | 9/2011 |
| JP | 2011-192126 A | 9/2011 |
| JP | 2011-198184 A | 10/2011 |
| JP | 2011-206323 A | 10/2011 |
| JP | 2011-259253 A | 12/2011 |
| JP | 2012-35071 A | 2/2012 |
| JP | 2012-59264 A | 3/2012 |
| JP | 2012-524640 A | 10/2012 |
| JP | 2012-230503 A | 11/2012 |
| JP | 2013-103020 A | 5/2013 |
| JP | 2013-117690 A | 6/2013 |
| JP | 2013-544140 A | 12/2013 |
| JP | 2016-502875 A | 2/2016 |
| JP | 2016-528016 A | 9/2016 |
| JP | 2016-177151 A | 10/2016 |
| JP | 2016-202751 A | 12/2016 |
| JP | 2017-134689 A | 8/2017 |
| JP | 2017-211994 A | 11/2017 |
| JP | 2017-532069 A | 11/2017 |
| KR | 10-2006-0117570 A | 11/2006 |
| KR | 10-2011-0017076 A | 2/2011 |
| KR | 10-2012-0023657 A | 3/2012 |
| KR | 10-2012-0076559 A | 7/2012 |
| KR | 10-2013-0043698 A | 5/2013 |
| KR | 10-2013-0111569 A | 10/2013 |
| KR | 10-2013-0111570 A | 10/2013 |
| KR | 10-2013-0135282 A | 12/2013 |
| KR | 10-2017-0003608 A | 1/2017 |
| WO | 99/41682 A2 | 8/1999 |
| WO | 02/27530 A2 | 4/2002 |
| WO | 2005/070289 A1 | 8/2005 |
| WO | 2009/129402 A1 | 10/2009 |
| WO | 2010/126825 A1 | 11/2010 |
| WO | 2012/021507 A2 | 2/2012 |
| WO | 2012/061438 A2 | 5/2012 |
| WO | 2012/061440 A2 | 5/2012 |
| WO | 2012/078079 A2 | 6/2012 |
| WO | 2012/086910 A1 | 6/2012 |
| WO | 2013/052789 A1 | 4/2013 |
| WO | 2013/109762 A1 | 7/2013 |
| WO | 2013/109777 A1 | 7/2013 |
| WO | 2013/109916 A1 | 7/2013 |
| WO | 2013/173838 A2 | 11/2013 |
| WO | 2014/207294 A1 | 12/2014 |
| WO | 2015/027133 A1 | 2/2015 |
| WO | 2015/179592 A1 | 11/2015 |
| WO | 2015/198488 A1 | 12/2015 |
| WO | 2016/036582 A2 | 3/2016 |
| WO | 2017/037242 A1 | 3/2017 |
| WO | 2018/222313 A1 | 12/2018 |
| WO | 2019/017508 A1 | 1/2019 |
| WO | 2019/024603 A1 | 2/2019 |
| WO | 2019/231982 A1 | 12/2019 |

OTHER PUBLICATIONS

International Search Report and Written Opinion received for PCT Patent Application No. PCT/US2020/035199, dated Oct. 30, 2020, 20 pages.
Office Action received for European Patent Application No. 20182116.2, dated Nov. 6, 2020, 9 pages.
Office Action received for Korean Patent Application No. 10-2019-7025781, dated Oct. 30, 2020, 10 pages (4 pages of English Translation and 6 pages of Official Copy).
Applicant-Initiated Interview Summary received for U.S. Appl. No. 16/138,809, dated Dec. 16, 2020, 7 pages.
Board Decision received for Chinese Patent Application No. 201380081349.6, dated Nov. 23, 2020, 2 pages (1 page of English Translation and 1 page of Official Copy).
Non-Final Office Action received for U.S. Appl. No. 16/820,383, dated Dec. 14, 2020, 11 pages.
Non-Final Office Action received for U.S. Appl. No. 17/031,859, dated Dec. 15, 2020, 13 pages.
Notice of Allowance received for U.S. Appl. No. 16/144,753, dated Dec. 4, 2020, 22 pages.
Applicant-Initiated Interview Summary received for U.S. Appl. No. 16/377,892, dated Oct. 13, 2020, 5 pages.
Applicant-Initiated Interview Summary received for U.S. Appl. No. 16/378,136, dated Oct. 13, 2020, 4 pages.
Final Office Action received for U.S. Appl. No. 15/627,069, dated Oct. 20, 2020, 25 pages.
Non-Final Office Action received for U.S. Appl. No. 16/894,309, dated Oct. 15, 2020, 24 pages.
Notice of Allowance received for U.S. Appl. No. 15/705,849, dated Oct. 16, 2020, 14 pages.
Notice of Allowance received for U.S. Appl. No. 16/556,023, dated Oct. 15, 2020, 8 pages.
Result of Consultation received for European Patent Application No. 19721883.7, dated Oct. 7, 2020, 3 pages.
Applicant-Initiated Interview Summary received for U.S. Appl. No. 17/031,859, dated Feb. 26, 2021, 4 pages.
Applicant-Initiated Interview Summary received for U.S. Appl. No. 17/031,874, dated Feb. 26, 2021, 4 pages.
Decision to Refuse received for European Patent Application No. 18154145.9, dated Feb. 17, 2021, 20 pages.
Final Office Action received for U.S. Appl. No. 16/894,309, dated Feb. 24, 2021, 30 pages.
Minutes of the Oral Proceedings received for European Patent Application No. 18154145.9, mailed on Feb. 12, 2020, 8 pages.
Notice of Acceptance received for Australian Patent Application No. 2017277971, dated Feb. 17, 2021, 3 pages.
Office Action received for Chinese Patent Application No. 201380081349.6, dated Jan. 5, 2021, 16 pages (7 pages of English Translation and 9 pages of Official Copy).
Office Action received for Chinese Patent Application No. 201680047983.1, dated Feb. 1, 2021, 6 pages (3 pages of English Translation and 3 pages of Official Copy).
Office Action received for Korean Patent Application No. 10-2020-7026035, dated Feb. 19, 2021, 13 pages (6 pages of English Translation and 7 pages of Official Copy).
Applicant Initiated Interview Summary received for U.S. Appl. No. 15/608,848, dated Oct. 26, 2020, 3 pages.
Applicant-Initiated Interview Summary received for U.S. Appl. No. 15/925,652, dated Nov. 3, 2020, 4 pages.
Applicant-Initiated Interview Summary received for U.S. Appl. No. 16/144,753, dated Nov. 4, 2020, 3 pages.
European Search Report received for European Patent Application No. 20182116.2, dated Oct. 21, 2020, 4 pages.
Notice of Allowance received for U.S. Appl. No. 16/144,735, dated Oct. 28, 2020, 13 pages.
Office Action received for Japanese Patent Application No. 2020-104679, dated Sep. 18, 2020, 13 pages (7 pages of English Translation and 6 pages of Official Copy).
Adeniyi Samuel, "How to connect a second PS4 controller to a PlayStation 4 console", Online available on: https://www.youtube.com/watch?v=mOZX_SrNISE, May 28, 2017, 2 pages.

(56) References Cited

OTHER PUBLICATIONS

Allison Conor, "Working out with Fiit's wearable-powered boutique fitness classes", Online available at: https://www.wareable.com/wearable-tech/fiit-fitness-classesreview-3849, May 14, 2018, 8 pages.
Applicant Initiated Interview Summary received for U.S. Appl. No. 16/894,309, dated Jan. 26, 2021, 3 pages.
Applicant-Initiated Interview Summary received for U.S. Appl. No. 15/627,069, dated Jan. 22, 2021, 4 pages.
Decision to Refuse received for European Patent Application No. 17810749.6, dated Jan. 29, 2021, 24 pages.
Extended European Search Report received for European Patent Application No. 20203526.7, dated Jan. 29, 2021, 13 pages.
Final Office Action received for U.S. Appl. No. 16/377,892, dated Jan. 28, 2021, 11 pages.
Final Office Action received for U.S. Appl. No. 16/378,136, dated Jan. 28, 2021, 9 pages.
Hamilton Jim, "Peloton Tips", Online available on: https://www.youtube.com/watch?app=desktop&v=OneXtB0kaD4, Oct. 22, 2015, 3 pages.
Intention to Grant received for Danish Patent Application No. PA201670656, dated Jan. 18, 2021, 2 pages.
Minutes of the Oral Proceedings received for European Patent Application No. 17810749.6, mailed on Jan. 26, 2021, 8 pages.
Notice of Allowance received for Chinese Patent Application No. 201710439448.7, dated Jan. 26, 2021, 2 pages (1 page of English Translation and 1 page of Official Copy).
Office Action received for European Patent Application No. 16837432.0, dated Jan. 27, 2021, 7 pages.
Office Action received for Japanese Patent Application No. 2020-000492, dated Dec. 11, 2020, 6 pages (3 pages English Translation and 3 pages of Official Copy).
Office Action received for Korean Patent Application No. 10-2019-7033834, dated Jan. 22, 2021, 13 pages (6 pages of English Translation and 7 pages of Official Copy).
Result of Consultation received for European Patent Application No. 17810749.6, dated Jan. 18, 2021, 3 pages.
Result of Consultation received for European Patent Application No. 17810749.6, dated Jan. 21, 2021, 18 pages.
Supplemental Notice of Allowance received for U.S. Appl. No. 15/925,652, dated Jan. 26, 2021, 3 pages.
Supplemental Notice of Allowance received for U.S. Appl. No. 16/556,023, dated Feb. 3, 2021, 2 pages.
Vicky's Blog, "How to Log in to PS4 Automatically with Particular User?", Online available on: https://www.youtube.com/watch?v=kqdlzXAvOkY, May 30, 2018, 3 pages.
Yoyodavid, "How to Use Multiple Accounts on the Playstation 4", Online available at: https://www.youtube.com/watch?v=5V21obRMeKE, Jan. 9, 2014, 3 pages.
Applicant-Initiated Interview Summary received for U.S. Appl. No. 16/820,383, dated Mar. 11, 2021, 2 pages.
Notice of Acceptance received for Australian Patent Application No. 2019250251, dated Feb. 18, 2021, 3 pages.
Notice of Allowance received for U.S. Appl. No. 15/925,652, dated Mar. 9, 2021, 9 pages.
Notice of Allowance received for U.S. Appl. No. 16/144,864, dated Mar. 12, 2021, 2 pages.
Office Action received for Chinese Patent Application No. 202010606407.4, dated Jan. 27, 2021, 16 pages (7 pages of English Translation and 9 pages of Official Copy).
Office Action received for Japanese Patent Application No. 2019-563407, dated Feb. 5, 2021, 5 pages (2 pages of English Translation and 3 pages of Official Copy).
Final Office Action received for U.S. Appl. No. 15/608,848, dated Aug. 21, 2020, 15 pages.
Final Office Action received for U.S. Appl. No. 16/138,809, dated Aug. 27, 2020, 24 pages.
Office Action received for Australian Patent Application No. 2017277971, dated Aug. 12, 2020, 3 pages.
Office Action received for Chinese Patent Application No. 201380081349.6, dated Jul. 15, 2020, 9 pages (4 pages of English Translation and 5 pages of Official Copy).
Office Action received for Korean Patent Application No. 10-2019-7025538, dated Aug. 15, 2020, 8 pages (4 pages of English Translation and 4 pages of Official Copy).
Non-Final Office Action received for U.S. Appl. No. 15/608,848, dated Feb. 12, 2021, 14 pages.
Notice of Allowance received for U.S. Appl. No. 16/144,753, dated Feb. 10, 2021, 8 pages.
Notice of Allowance received for U.S. Appl. No. 16/144,864, dated Feb. 9, 2021, 13 pages.
Supplemental Notice of Allowance received for U.S. Appl. No. 15/925,652, dated Feb. 17, 2021, 3 pages.
CBS This Morning, "This smart mirror puts a personal trainer in your reflection", Available at: https://www.youtube.com/watch?v=nSmTTZcpVGg, Oct. 13, 2018, 4 pages.
Non-Final Office Action received for U.S. Appl. No. 15/925,652, dated Aug. 7, 2020, 39 pages.
Office Action received for Australian Patent Application No. 2019250251, dated Aug. 6, 2020, 3 pages.
Summons to Attend Oral Proceedings received for European Patent Application No. 17810749.6, mailed on Aug. 12, 2020, 11 pages.
Advisory Action received for U.S. Appl. No. 16/144,864, dated Jul. 6, 2020, 6 pages.
Applicant-Initiated Interview Summary received for U.S. Appl. No. 15/705,849, dated Jun. 29, 2020, 3 pages.
Office Action Received for Danish Patent Application No. PA201670656, dated Jul. 1, 2020, 4 pages.
Office Action received for Japanese Patent Application No. 2019-044107, dated May 29, 2020, 6 pages (3 pages of English Translation and 3 pages of Official Copy).
Final Office Action received for U.S. Appl. No. 16/418,786, dated Jan. 13, 2021, 14 pages.
Notice of Acceptance received for Australian Patent Application No. 2018268972, dated Dec. 18, 2020, 3 pages.
Notice of Allowance received for Japanese Patent Application No. 2018-014096, dated Jan. 5, 2021, 3 pages (1 page of English Translation and 2 pages of Official Copy).
Notice of Allowance received for Japanese Patent Application No. 2020-104679, dated Jan. 4, 2021, 4 pages (1 page of English Translation and 3 pages of Official Copy).
Notice of Allowance received for U.S. Appl. No. 16/556,023, dated Jan. 13, 2021, 8 pages.
Search Report and Opinion received for Danish Patent Application No. PA202070614, dated Jan. 14, 2021, 9 pages.
Supplemental Notice of Allowance received for U.S. Appl. No. 15/925,652, dated Jan. 6, 2021, 3 pages.
Notice of Acceptance received for Australian Patent Application No. 2020204153, dated Jul. 6, 2020, 3 pages.
Notice of Allowance received for U.S. Appl. No. 15/705,849, dated Jul. 28, 2020, 10 pages.
Notice of Allowance received for U.S. Appl. No. 16/144,864, dated Jul. 28, 2020, 27 pages.
Office Action received for Chinese Patent Application No. 201680047983.1, dated Jul. 1, 2020, 6 pages (3 pages of English Translation and 3 pages of Official Copy).
Non-Final Office Action received for U.S. Appl. No. 17/031,874, dated Dec. 28, 2020, 14 pages.
Result of Consultation received for European Patent Application No. 17810749.6, dated Dec. 15, 2020, 3 pages.
Advisory Action received for U.S. Appl. No. 16/144,864, dated Jul. 29, 2019, 6 pages.
Advisory Action received for U.S. Appl. No. 14/732,773, dated Aug. 23, 2019, 6 pages.
Advisory Action received for U.S. Appl. No. 14/732,773, dated Nov. 9, 2018, 6 pages.
Advisory Action received for U.S. Appl. No. 14/839,922, dated Mar. 24, 2017, 4 pages.
Advisory Action received for U.S. Appl. No. 16/144,849, dated Aug. 12, 2019, 5 pages.

(56) References Cited

OTHER PUBLICATIONS

Apple, "iPhone User's Guide", Available at <http://mesnotices.20minutes.fr/manuel-notice-mode-emploi/APPLE/IPHONE%2D%5FE#>, Retrieved on Mar. 27, 2008, Jun. 2007, 137 pages.
Applicant Initiated Interview Summary received for U.S. Appl. No. 15/608,848, dated May 12, 2020, 5 pages.
Applicant Initiated Interview Summary received for U.S. Appl. No. 15/627,069, dated Nov. 4, 2019, 6 pages.
Applicant Initiated Interview Summary received for U.S. Appl. No. 16/144,849, dated Jan. 21, 2020, 6 pages.
Applicant Initiated Interview Summary received for U.S. Appl. No. 16/144,864, dated Apr. 29, 2020, 4 pages.
Applicant-Initiated Interview Summary received for U.S. Appl. No. 15/600,243, dated Nov. 1, 2019, 6 pages.
Applicant-Initiated Interview Summary received for U.S. Appl. No. 15/608,848, dated Nov. 1, 2019, 3 pages.
Applicant-Initiated Interview Summary received for U.S. Appl. No. 15/705,849, dated Feb. 14, 2020, 3 pages.
Applicant-Initiated Interview Summary received for U.S. Appl. No. 16/138,809, dated Jun. 9, 2020, 7 pages.
Certificate of Examination received for Australian Patent Application No. 2018101855, mailed on Aug. 6, 2019, 2 pages.
Certification of Examination received for Australian Patent Application No. 2018100158, mailed on Oct. 23, 2018, 2 pages.
Cho H.S, "Satisfactory Innovative Smart-watch (Fitbit force), review after seven days of use, such as the amount of sleep and movement (improving sleep is the object of X-Blue", Online Available at: <https://x-blueuv.blogspot.com/2013/12/fitbit-force.html>, Dec. 3, 2013, 8 pages (2 pages of English Translation and 6 pages of Official Copy).
CNET,"Google Fit's automatic activity tracking is getting smarter on Android Wear", Available online at: https://www.youtube.com/watch?v=IttzlCid_d8, May 18, 2016, 1 page.
Codrington Simon, "Intuitive Scrolling Interfaces with CSS Scroll Snap Points", Online Available at: https://www.sitepoint.com/intuitive-scrolling-interfaces-with-css-scroll-snap-points/, Dec. 8, 2015, 14 pages.
Corrected Notice of Allowance received for U.S. Appl. No. 14/732,773, dated Feb. 10, 2020, 3 pages.
Corrected Notice of Allowance received for U.S. Appl. No. 14/732,773, dated Mar. 24, 2020, 3 pages.
Corrected Notice of Allowance received for U.S. Appl. No. 15/183,663, dated Feb. 25, 2019, 3 pages.
Corrected Notice of Allowance received for U.S. Appl. No. 15/183,663, dated Mar. 27, 2019, 2 pages.
Corrected Notice of Allowance received for U.S. Appl. No. 15/600,243, dated Feb. 5, 2020, 3 pages.
Corrected Notice of Allowance received for U.S. Appl. No. 15/600,243, dated Mar. 13, 2020, 3 pages.
Corrected Notice of Allowance received for U.S. Appl. No. 15/600,243, dated Mar. 31, 2020, 5 pages.
DC Rainmaker, "Garmin Fenix3 New Auto Climb Functionality", Available online at: https://www.youtube.com/watch?v=iuavOSNpVRc, Feb. 19, 2015, 1 page.
Decision to Grant received for Danish Patent Application No. PA201870379, dated Jul. 5, 2019, 2 pages.
Decision to Refuse received for European Application No. 13811085.3, dated Sep. 11, 2018, 21 pages.
Decision to Refuse received for European Patent Application No. 15771747.1, dated Aug. 10, 2018, 22 pages.
DwProgressBar v2: Stepping and Events, davidwalsh.name/dwprogressbar-2-stepping-events-mootools-progress-bar, retrieved from the Way back Machine, Aug. 31, 2008, 4 pages.
Evergreen et al, "Bar Chart", Better Evaluation, Available Online at: https://www.betterevaluation.org/en/evaluation-options/BarChart, Oct. 31, 2014, 8 pages.
Extended European Search Report received for European Patent Application No. 16837432.0, dated Mar. 11, 2019, 10 pages.
Extended European Search Report received for European Patent Application No. 18154145.9, dated Mar. 2, 2018, 8 pages.

Final Office Action received for U.S. Appl. No. 12/205,847, dated Apr. 25, 2012, 42 pages.
Final Office Action received for U.S. Appl. No. 14/732,773, dated Jul. 13, 2018, 48 pages.
Final Office Action received for U.S. Appl. No. 14/732,773, dated Jun. 21, 2019, 32 pages.
Final Office Action received for U.S. Appl. No. 14/839,922, dated Dec. 14, 2016, 22 pages.
Final Office Action received for U.S. Appl. No. 15/608,848, dated Jun. 26, 2019, 27 pages.
Final Office Action received for U.S. Appl. No. 15/627,069, dated Mar. 2, 2020, 22 pages.
Final Office Action received for U.S. Appl. No. 15/705,849, dated May 1, 2020, 17 pages.
Final Office Action received for U.S. Appl. No. 15/925,652, dated Aug. 1, 2019, 30 Pages.
Final Office Action received for U.S. Appl. No. 16/144,735, dated May 4, 2020, 12 pages.
Final Office Action received for U.S. Appl. No. 16/144,849, dated Jun. 7, 2019, 29 pages.
Final Office Action received for U.S. Appl. No. 16/144,864, dated May 17, 2019, 24 pages.
Final Office Action received for U.S. Appl. No. 16/144,864, dated May 28, 2020, 29 pages.
"Fitbit App", Available online at: http://web.archive.org/web/20180114083150/https://www.fitbit.com/au/app, Jan. 14, 2018, 8 pages.
Garmin, "Fenix 5x Owner's Manual", Online Available at:—https://web.archive.org/web/20180127170640/https://static.garmin.com/pumac/fenix5x_OM_EN.pdf, Jan. 27, 2018, 42 pages.
"Graphs and Charts", Online Available at: https://www.teachervision.com/lesson-planning/graph-chart-teacher-resources, retrieved on Dec. 12, 2018, 4 pages.
Intention to Grant received for Danish Patent Application No. PA201570668, dated Mar. 27, 2017, 2 pages.
Intention to Grant received for Danish Patent Application No. PA201870379, dated May 2, 2019, 2 pages.
International Preliminary Report on Patentability received for PCT Application No. PCT/US2016/037686, dated Mar. 1, 2018, 12 pages.
International Preliminary Report on Patentability received for PCT Patent Application No. PCT/US2013/073195, dated Jun. 16, 2016, 10 pages.
International Preliminary Report on Patentability received for PCT Patent Application No. PCT/US2015/047282, dated Mar. 16, 2017, 26 pages.
International Preliminary Report on Patentability received for PCT Patent Application No. PCT/US2017/035554, dated Dec. 20, 2018, 39 pages.
International Preliminary Report on Patentability received for PCT Patent Application No. PCT/US2018/031662, dated Nov. 28, 2019, 12 pages.
International Search Report and Written Opinion received for PCT Patent Application No. PCT/US2015/047282, dated May 9, 2016, 33 pages.
International Search Report and Written Opinion received for PCT Patent Application No. PCT/US2016/037686, dated Sep. 9, 2016, 19 pages.
International Search Report and Written Opinion received for PCT Patent Application No. PCT/US2017/035554, dated Sep. 22, 2017, 42 pages.
International Search Report and Written Opinion received for PCT Patent Application No. PCT/US2018/031662, dated Sep. 27, 2018, 17 pages.
International Search Report and Written Opinion received for PCT Patent Application No. PCT/US2019/024570, dated Aug. 8, 2019, 18 pages.
International Search Report received for PCT Patent Application No. PCT/US2013/073195, dated Jun. 23, 2014, 3 pages.
International Written Opinion received for PCT Patent Application No. PCT/US2013/073195, dated Jun. 23, 2014, 8 pages.

(56) References Cited

OTHER PUBLICATIONS

Invitation to Pay Addition Fees and Partial International Search Report received for PCT Patent Application No. PCT/US2018/031662, dated Jul. 16, 2018, 13 pages.
Invitation to Pay Additional Fees received for PCT Patent Application No. PCT/US2015/047282, dated Dec. 22, 2015, 7 pages.
Invitation to Pay Additional Fees received for PCT Patent Application No. PCT/US2017/035554, dated Jul. 20, 2017, 2 pages.
Jenbsjourney, "Wondering About a Fitbit?", Available at: https://jenbsjourney.blogspot.kr/2013/08/wondering-about-fitbit.html, Aug. 6, 2013, 12 pages.
Minutes of Oral Proceedings received for European Patent Application No. 13811085.3, mailed on Sep. 11, 2018, 3 pages.
Minutes of Oral Proceedings received for European Patent Application No. 15771747.1, mailed on Aug. 10, 2018, 11 pages.
Le Mugs, Online Available at: https://web.archive.org/web/20151029034349/http://le-mugs.com/, Oct. 29, 2015, 14 pages.
Multi-Set Bar Chart, The Data Visualization Catalogue, Available Online at: https://datavizcatalogue.com/methods/multiset_barchart.html, Feb. 8, 2014, 3 pages.
My CalStep, http://www.surprisesoftware.com/mycalstep/, retrieved from the Way back Machine, May 9, 2007, 2 pages.
Non-Finai Office Action received for U.S. Appl. No. 15/608,848, dated Nov. 2, 2018, 21 pages.
Non-Final Office Action received for U.S. Appl. No. 12/205,847, dated Oct. 3, 2011, 59 pages.
Non-Final Office Action received for Fitbit U.S. Appl. No. 14/732,773, dated Feb. 8, 2019, 32 pages.
Non-Final Office Action received for U.S. Appl. No. 14/732,773, dated Jan. 19, 2018, 45 pages.
Non-Final Office Action received for U.S. Appl. No. 14/839,916, dated Feb. 4, 2016, 19 pages.
Non-Final Office Action received for U.S. Appl. No. 14/839,916, dated May 1, 2017, 18 pages.
Non-Final Office Action received for U.S. Appl. No. 14/839,922, dated Aug. 17, 2016, 25 pages.
Non-Final Office Action received for U.S. Appl. No. 14/839,922, dated Feb. 25, 2016, 20 pages.
Non-Final Office Action received for U.S. Appl. No. 15/183,663, dated Jul. 9, 2018, 13 pages.
Non-Final Office Action received for U.S. Appl. No. 15/600,243, dated Jun. 27, 2019, 17 pages.
Non-Final Office Action received for U.S. Appl. No. 15/608,848, dated Feb. 6, 2020, 12 pages.
Non-Final Office Action received for U.S. Appl. No. 15/627,069, dated Jun. 21, 2019, 22 pages.
Non-Final Office Action received for U.S. Appl. No. 15/627,069, dated May 26, 2020, 25 pages.
Non-Final Office Action received for U.S. Appl. No. 15/705,849, dated Nov. 12, 2019, 15 pages.
Non-Final Office Action received for U.S. Appl. No. 15/925,652, dated Apr. 5, 2019, 28 pages.
Non-Final Office Action received for U.S. Appl. No. 16/138,809, dated Feb. 28, 2020, 22 pages.
Non-Final Office Action received for U.S. Appl. No. 16/144,735, dated Feb. 19, 2020, 10 pages.
Non-Final Office Action received for U.S. Appl. No. 16/144,753, dated Mar. 5, 2020, 9 pages.
Non-Final Office Action received for U.S. Appl. No. 16/144,849, dated Dec. 31, 2018, 28 pages.
Non-Final Office Action received for U.S. Appl. No. 16/144,849, dated Sep. 17, 2019, 9 pages.
Non-Final Office Action Received for U.S. Appl. No. 16/144,864, dated Dec. 18, 2018, 19 pages.
Non-Final Office Action received for U.S. Appl. No. 16/144,864, dated Jan. 31, 2020, 29 pages.
Non-Final Office Action received for U.S. Appl. No. 16/377,892, dated May 21, 2020, 9 pages.
Non-Final Office Action received for U.S. Appl. No. 16/378,136, dated Jun. 2, 2020, 8 pages.
Non-Final Office Action received for U.S. Appl. No. 16/418,786, dated Apr. 24, 2020, 16 pages.
Notice of Acceptance received for Australian Patent Application No. 2015312215, dated Oct. 9, 2017, 3 pages.
Notice of Acceptance received for Australian Patent Application No. 2019201583, dated Jul. 15, 2019, 3 pages.
Notice of Acceptance received for Australian Patent Application No. 2019222943, dated May 5, 2020, 3 pages.
Notice of Allowance received for Chinese Patent Application No. 201580037927.5, dated Oct. 17, 2019, 3 pages (1 page of English Translation and 2 pages of Official Copy).
Notice of Allowance received for Chinese Patent Application No. 201810105846.X, dated Feb. 18, 2020, 2 pages (1 page of English Translation and 1 page of Official Copy).
Notice of Allowance received for Danish Patent Application No. PA201570666, dated Sep. 15, 2016, 1 page.
Notice of Allowance received for Danish Patent Application No. PA201570668, dated Oct. 30, 2017, 2 pages.
Notice of Allowance received for Japanese Patent Application No. 2016-535045, dated Mar. 2, 2018, 4 pages (1 page of English Translation and 3 pages of Official Copy).
Notice of Allowance received for Japanese Patent Application No. 2016-557650, dated Apr. 9, 2019, 4 pages (1 page of English Translation and 3 pages of Official Copy).
Notice of Allowance received for Japanese Patent Application No. 2018-068846, dated Dec. 9, 2019, 4 pages (1 page of English Translation and 3 pages of Official Copy).
Notice of Allowance received for Korean Patent Application No. 10-2016-7014577, dated May 30, 2019, 5 pages (2 pages of English Translation and 3 pages of Official Copy).
Notice of Allowance received for Korean Patent Application No. 10-2016-7033638, dated May 31, 2017, 5 pages (2 pages of English Translation and 3 pages of Official Copy).
Notice of Allowance received for Taiwanese Patent Application No. 104128685, dated May 3, 2017, 3 pages (Official Copy Only) (See Communication under 37 CFR § 1.98(a) (3)).
Notice of Allowance received for U.S. Appl. No. 12/205,847, dated Aug. 20, 2012, 13 pages.
Notice of Allowance received for U.S. Appl. No. 14/732,773, dated Dec. 18, 2019, 21 pages.
Notice of Allowance received for U.S. Appl. No. 14/839,916, dated Aug. 31, 2016, 11 pages.
Notice of Allowance received for U.S. Appl. No. 14/839,916, dated Jan. 10, 2018, 19 pages.
Notice of Allowance received for U.S. Appl. No. 14/839,922, dated Jan. 26, 2018, 2 pages.
Notice of Allowance received for U.S. Appl. No. 14/839,922, dated Jul. 6, 2017, 8 pages.
Notice of Allowance received for U.S. Appl. No. 14/839,922, dated Nov. 2, 2017, 8 pages.
Notice of Allowance received for U.S. Appl. No. 15/183,663, dated Jan. 17, 2019, 6 pages.
Notice of Allowance received for U.S. Appl. No. 15/600,243, dated Dec. 12, 2019, 7 pages.
Notice of Allowance received for U.S. Appl. No. 15/616,480, dated Jan. 3, 2019, 8 pages.
Notice of Allowance received for U.S. Appl. No. 16/144,671, dated Feb. 10, 2020, 17 pages.
Notice of Allowance received for U.S. Appl. No. 16/144,849, dated Apr. 17, 2020, 2 pages.
Notice of Allowance received for U.S. Appl. No. 16/144,849, dated Mar. 6, 2020, 9 pages.
Office Action received for Australian Patent Application No. 2015312215, dated Oct. 13, 2016, 3 pages.
Office Action received for Australian Patent Application No. 2017100667, dated Aug. 3, 2017, 9 pages.
Office Action received for Australian Patent Application No. 2018100158, dated Apr. 23, 2018, 5 pages.
Office Action received for Australian Patent Application No. 2018101855, dated Feb. 22, 2019, 4 pages.
Office Action received for Australian Patent Application No. 2018200428, dated Mar. 7, 2018, 4 pages.

(56) References Cited

OTHER PUBLICATIONS

Office Action received for Australian Patent Application No. 2018200428, dated Nov. 15, 2018, 4 pages.
Office Action received for Australian Patent Application No. 2019100495, dated Mar. 6, 2020, 3 pages.
Office Action received for Australian Patent Application No. 2019100495, dated Mar. 16, 2020, 3 pages.
Office Action received for Australian Patent Application No. 2019100495, dated Sep. 17, 2019, 7 pages.
Office Action received for Australian Patent Application No. 2019222943, dated Oct. 3, 2019, 3 pages.
Office Action received for Chinese Patent Application No. 201380081349.6, dated Feb. 26, 2019, 12 pages (6 pages of English Translation and 6 pages of Official Copy).
Office Action received for Chinese Patent Application No. 201380081349.6, dated Jan. 16, 2020, 11 pages (6 pages of English Translation and 5 pages of Official Copy).
Office Action received for Chinese Patent Application No. 201380081349.6, dated Jul. 15, 2019, 10 pages (5 pages of English Translation and 5 pages of Official copy).
Office Action received for Chinese Patent Application No. 201580037927.5, dated Apr. 22, 2019, 9 pages (4 pages of English Translation and 5 pages of Official Copy).
Office Action received for Chinese Patent Application No. 201580037927.5, dated Jul. 20, 2018, 21 pages (6 pages of English Translation and 15 pages of Official copy).
Office Action received for Chinese Patent Application No. 201680047983.1, dated Mar. 18, 2019, 18 pages (6 pages of English Translation and 12 pages of Official Copy).
Office Action received for Chinese Patent Application No. 201680047983.1, dated Nov. 28, 2019, 9 pages (4 pages of English Translation and 5 pages of Official Copy).
Office Action received for Chinese Patent Application No. 201710439448.7, dated Mar. 27, 2020, 13 pages (7 pages of English Translation and 6 pages of Official Copy).
Office Action received for Chinese Patent Application No. 201810105846.X, dated Aug. 27, 2019, 12 pages (5 pages of English Translation and 7 pages of Official Copy).
Office Action received for Chinese Patent Application No. 201810105846.X, dated Feb. 25, 2019, 10 pages (5 pages of English Translation and 5 pages of Official copy).
Office Action received for Chinese Patent Application No. 201810105846.X, dated Nov. 28, 2019, 9 pages (5 pages of English Translation and 4 pages of Official Copy).
Office Action received for Danish Patent Application No. PA201570666, dated Feb. 2, 2016, 9 pages.
Office Action received for Danish Patent Application No. PA201570666, dated Jun. 27, 2016, 4 pages.
Office Action received for Danish Patent Application No. PA201570668, dated Apr. 8, 2016, 8 pages.
Office Action received for Danish Patent Application No. PA201570668, dated Sep. 9, 2016, 3 pages.
Office Action received for Danish Patent Application No. PA201670656, dated Jun. 14, 2017, 3 pages.
Office Action Received for Danish Patent Application No. PA201670656, dated May 2, 2019, 4 pages.
Office Action Received for Danish Patent Application No. PA201670656, dated May 30, 2018, 5 pages.
Office Action Received for Danish Patent Application No. PA201670656, dated Nov. 3, 2016, 8 pages.
Office Action received for Danish Patent Application No. PA201770191, dated Jan. 25, 2018, 3 pages.
Office Action received for Danish Patent Application No. PA201770191, dated Nov. 21, 2018, 4 pages.
Office Action received for Danish Patent Application No. PA201770191, dated Oct. 25, 2019, 4 pages.
Office Action received for Danish Patent Application No. PA201770423, dated Jun. 12, 2018, 7 pages.
Office Action received for Danish Patent Application No. PA201770423, dated Mar. 29, 2019, 6 pages.
Office Action received for Danish Patent Application No. PA201870378, dated Feb. 25, 2019, 3 pages.
Office Action received for Danish Patent Application No. PA201870378, dated Jan. 6, 2020, 3 pages.
Office Action received for Danish Patent Application No. PA201870379, dated Feb. 28, 2019, 3 pages.
Office Action received for Danish Patent Application No. PA201870380, dated Mar. 5, 2020, 2 pages.
Office Action received for Danish Patent Application No. PA201870380, dated Mar. 27, 2019, 4 pages.
Office Action received for Danish Patent Application No. PA201870380, dated Sep. 11, 2018, 9 pages.
Office Action received for European Patent Application No. 13811085.3, dated Apr. 20, 2018, 15 pages.
Office Action received for European Patent Application No. 16837432.0, dated Jan. 10, 2020, 7 pages.
Office Action received for European Patent Application No. 17810749.6, dated Aug. 20, 2019, 9 pages.
Office Action received for European Patent Application No. 18154145.9, dated Apr. 3, 2018, 6 pages.
Office Action received for European Patent Application No. 19721883.7, dated Jan. 10, 2020, 4 pages.
Office Action received for European Patent Application No. 19721883.7, dated May 28, 2020, 11 pages.
Office Action received for European Patent Application No. 15771747.1, dated Oct. 31, 2017, 7 pages.
Office Action received for German Patent Application No. 112015002326.7, dated Feb. 20, 2019, 7 pages (2 pages of English Translation and 5 pages of Official Copy).
Office Action received for Japanese Patent Application No. 2016-535045, dated May 12, 2017, 10 pages (5 pages of English Translation and 5 pages of Official Copy).
Office Action received for Japanese Patent Application No. 2016-557650, dated Apr. 13, 2018, 9 pages (5 pages of English Translation and 4 pages of Official Copy).
Office Action received for Japanese Patent Application No. 2016-557650, dated Aug. 10, 2017, 10 pages (5 pages of English Translation and 5 pages of Official Copy).
Office Action received for Japanese Patent Application No. 2016-557650, dated Nov. 9, 2018, 6 pages (3 pages of English Translation and 3 pages of Official copy).
Office Action received for Japanese Patent Application No. 2018-014096, dated Jan. 6, 2020, 17 pages (8 pages of English Translation and 9 pages of Official Copy).
Office Action received for Japanese Patent Application No. 2018-014096, dated Jun. 29, 2018, 20 pages (11 pages of English Translation and 9 pages of Official Copy).
Office Action received for Japanese Patent Application No. 2018-014096, dated May 8, 2019, 14 pages (7 pages of English Translation and 7 pages of Official Copy).
Office Action received for Japanese Patent Application No. 2018-014096, dated Nov. 6, 2018, 15 pages (7 pages of English Translation and 8 pages of Official Copy).
Office Action received for Japanese Patent Application No. 2018-068846, dated Jan. 8, 2019, 6 pages (3 pages of English Translation and 3 pages of Official copy).
Office Action received for Japanese Patent Application No. 2019-162293, dated Jan. 31, 2020, 8 pages (4 pages of English Translation and 4 pages of Official Copy).
Office Action received for Korean Patent Application No. 10-2016-7014577, dated Dec. 26, 2017, 14 pages (6 pages of English Translation and 8 pages of Official Copy).
Office Action received for Korean Patent Application No. 10-2016-7014577, dated Oct. 31, 2018, 11 pages (5 pages of English Translation and 6 pages of Official Copy).
Office Action received for Korean Patent Application No. 10-2016-7033638, dated Jan. 31, 2017, 6 pages (2 pages of English Translation and 4 pages of Official Copy).
Office Action received for Korean Patent Application No. 10-2019-7025538, dated Feb. 17, 2020, 12 pages (6 pages of English Translation and 6 pages of Official Copy).

(56) References Cited

OTHER PUBLICATIONS

Office Action received for Korean Patent Application No. 10-2019-7025781, dated Nov. 26, 2019, 10 pages (4 pages of English Translation and 6 pages of Official Copy).
Office Action received for Taiwanese Patent Application No. 104128685, dated Jan. 4, 2017, 40 pages (15 pages of English Translation and 25 pages of Official Copy).
Partial Supplementary European Search Report received for European Patent Application No. 17810749.6, dated Apr. 25, 2019, 8 pages.
Razykdreviews, "In Depth Review of Apple Watch Activity and Workout App", available at: https://www.youtube.com/watch?v=GkKI3qlK0ow>, Category: X Claims: 1-5, Category: L Reason: Internet citation/video, May 11, 2015, 1 page.
Rizknows, "Garmin Connect Mobile App—Review #2", https://www.youtube.com/watch?v=7my3wMpeRbE, Category: X Claims: 1-5 Category: L Reason: Internet citation/video, Oct. 22, 2015, 1 page.
Rizknows, "Tom Tom Multisport Cardio Review", Online available athttps://www.youtube.com/watch?v=WoVCzLrSN9A, Sep. 4, 2015, 1 page.
Search report and opinion received for Danish Patent Application No. PA201770191, dated Jun. 30, 2017, 9 pages.
Search Report and Opinion received for Danish Patent Application No. PA201770423, dated Oct. 4, 2017, 10 pages.
Search Report and Opinion received for Danish Patent Application No. PA201870378, dated Sep. 10, 2018, 9 pages.
Search Report and Opinion received for Danish Patent Application No. PA201870379, dated Sep. 14, 2018, 9 pages.
Smith, "Garmin Fenix 5 Activity/Smart Watch Review", Online Available athttps://www.youtube.com/watch?v=6PkQxXQxpoU, Sep. 2, 2017, 1 page.
Sportstechguides, "Garmin Fenix 5: How to Add Power Data Fields", Online Available athttps://www.youtube.com/watch?v=ZkPptnnXEiQ, Apr. 29, 2017, 2 pages.
Sportstechguides, "Garmin Fenix 5: How to Set Up Run Alerts", Online Available athttps://www.youtube.com/watch?v=gSMwv8vlhB4, May 13, 2017, 2 pages.
Summons to attend oral proceedings received for European Patent Application No. 13811085.3, mailed on Jan. 26, 2018, 14 pages.
Summons to Attend Oral Proceedings received for European Patent Application No. 15771747.1, mailed on May 25, 2018, 17 pages.
Supplemental Notice of Allowance received for U.S. Appl. No. 15/616,480, dated Mar. 28, 2019, 2 pages.
Supplemental Notice of Allowance received for U.S. Appl. No. 16/144,849, dated Mar. 31, 2020, 2 pages.
Supplementary European Search Report received for European Patent Application No. 17810749.6, dated Aug. 6, 2019, 6 pages.
Suunto Spartan Trainer Wrist HR 1.12, Online Available at: https://web.archive.org/web/20180127155200/https://ns.suunto.com/Manuals/Spartan_Trainer_WristHR/Userguides/Suunto_Spartan_Trainer_WristHR_UserGuide_EN.pdf, Jan. 17, 2018, 47 pages.
Suunto, "Suunto Spartan—Heart Rate Zones", Online Available athttps://www.youtube.com/watch?v=aixfoCnS0OU, Mar. 19, 2018, 2 pages.
Teunmo, "Data field: Visual Pace Alarm", Garmin Forum; Available online at: https://forums.garmin.com/forum/developers/connect-iq/connect-iq-showcase/115996-data-field-visual-pace-alarm, Nov. 17, 2015, 10 pages.
Tomtom, "TomTom Runner & Multi-Sport Reference Guide", Online available athttps://web.archive.org/web/20150908075934/http://download.tomtom.com/open/manuals/Runner_Multi-Sport/refman/TomTom-Runner-Multi-Sport-RG-en-gb.pdf, Sep. 8, 2015, 44 pages.
Utilization of Galaxy S4—S Health, ChatOn and Samsung Hub, Available at: http://seeit.kr/1263, Jun. 12, 2013, 25 pages (Official Copy only) (See Communication under 37 CFR § 1.98(a) (3)).
Visual Pace Alarm app, Available Online at: https://apps.garmin.com/en-US/apps/3940f3a2-4847-4078-a911-d77422966c82, Oct. 19, 2016, 1 page.

Wesley, "Apple Watch Series 1", online available at: http://toolbox.info/blog/archives/1737-unknown.html, May 28, 2015, 5 pages (Official copy only) (See Communication under 37 CFR § 1.98(a) (3)).
Youtube, "Apple Watch Series 3", Online available athttps://www.youtube.com/watch?v=iBPr9gEfkK8, Nov. 21, 2017, 15 pages (Official copy only) (See Communication under 37 CFR § 1.98(a) (3)).
Zlelik, "Garmin Fenix 5 Open Water Swimming Activity Demo", Online Available athttps://www.youtube.com/watch?v=iSVhdvw2dcs, Jun. 9, 2017, 1 page.
International Preliminary Report on Patentability received for PCT Patent Application No. PCT/US2019/024570, dated Nov. 19, 2020, 10 pages.
Notice of Allowance received for U.S. Appl. No. 15/925,652, dated Nov. 20, 2020, 9 pages.
Office Action received for Chinese Patent Application No. 201710439448.7, dated Oct. 10, 2020, 19 pages (8 pages of English Translation and 11 pages of Official Copy).
Result of Consultation received for European Patent Application No. 18154145.9, mailed on Nov. 30, 2020, 17 pages.
Applicant-Initiated Interview Summary received for U.S. Appl. No. 15/627,069, dated Jul. 20, 2020, 5 pages.
Cyclespeed Tours, "The Most Useful Data Fields to Display on Your Garmin", Online Available at: https://www.youtube.com/watch?v=AN0Eo50yxdg, Nov. 16, 2016, 3 pages.
Notice of Allowance received for U.S. Appl. No. 16/144,735, dated Jul. 21, 2020, 13 pages.
Office Action received for Australian Patent Application No. 2018268972, dated Jul. 9, 2020, 4 pages.
International Search Report and written Opinion received for PCT Patent Application No. PCT/US2020/025997, dated Jul. 1, 2020, 16 pages.
International Search Report and Written Opinion received for PCT Patent Application No. PCT/US2020/025997, dated Jul. 14, 2020, 15 pages.
Invitation to Pay Additional Fees received for PCT Patent Application No. PCT/US2020/035199, dated Sep. 8, 2020, 12 pages.
Notice of Allowance received for U.S. Appl. No. 16/144,864, dated Sep. 10, 2020, 3 pages.
Notice of Allowance received for U.S. Appl. No. 16/144,864, dated Sep. 16, 2020, 2 pages.
Notice of Allowance received for U.S. Appl. No. 16/588,950, dated Feb. 10, 2020, 9 pages.
Notice of Allowance received for U.S. Appl. No. 16/588,950, dated May 5, 2020, 9 pages.
Office Action received for Chinese Patent Application No. 201910858933.7, dated Aug. 18, 2020, 14 pages (7 pages of English Translation and 7 pages of Official Copy).
Office Action received for Danish Patent Application No. PA201970532, dated May 29, 2020, 3 pages.
Office Action received for Japanese Patent Application No. 2018-014096, dated Aug. 28, 2020, 4 pages (2 pages of English Translation and 2 pages of Official Copy).
Office Action received for Japanese Patent Application No. 2019-162293, dated Jul. 27, 2020, 9 pages (5 pages of English Translation and 4 pages of Official Copy).
Result of Consultation received for European Patent Application No. 18154145.9, mailed on Sep. 4, 2020, 3 pages.
Search Report and Opinion received for Danish Patent Application No. PA201970532, dated Nov. 8, 2019, 9 pages.
Supplemental Notice of Allowance received for U.S. Appl. No. 16/588,950, dated Apr. 1, 2020, 2 pages.
Supplemental Notice of Allowance received for U.S. Appl. No. 16/588,950, dated Jul. 29, 2020, 2 pages.
Supplemental Notice of Allowance received for U.S. Appl. No. 16/588,950, dated Jun. 18, 2020, 2 pages.
Final Office Action received for U.S. Appl. No. 16/144,753, dated Sep. 22, 2020, 9 pages.
Notice of Allowance received for U.S. Appl. No. 16/144,864, dated Sep. 29, 2020, 2 pages.
Summons to Attend Oral Proceedings received for European Patent Application No. 18154145.9, mailed on Sep. 17, 2020, 11 pages.

(56) References Cited

OTHER PUBLICATIONS

Applicant-Initiated Interview Summary received for U.S. Appl. No. 16/144,735, dated Jun. 18, 2020, 3 pages.
Applicant-Initiated Interview Summary received for U.S. Appl. No. 16/144,753, dated Jun. 18, 2020, 3 pages.
Applicant-Initiated Interview Summary received for U.S. Appl. No. 16/144,864, dated Jun. 22, 2020, 3 pages.
Office Action received for Australian Patent Application No. 2017277971, dated Jun. 3, 2020, 3 pages.
Applicant Initiated Interview Summary received for U.S. Appl. No. 17/030,318, dated Jul. 30, 2021, 4 pages.
Applicant Initiated Interview Summary received for U.S. Appl. No. 17/030,321, dated Jul. 30, 2021, 2 pages.
Corrected Notice of Allowance received for U.S. Appl. No. 16/377,892, dated Aug. 11, 2021, 3 pages.
Corrected Notice of Allowance received for U.S. Appl. No. 16/378,136, dated Aug. 11, 2021, 2 pages.
Corrected Notice of Allowance received for U.S. Appl. No. 16/820,383, dated Aug. 13, 2021, 2 pages.
Corrected Notice of Allowance received for U.S. Appl. No. 16/820,383, dated Aug. 19, 2021, 2 pages.
Final Office Action received for U.S. Appl. No. 17/030,321, dated Apr. 2, 2021, 28 pages.
Final Office Action received for U.S. Appl. No. 17/192,161, dated Aug. 16, 2021, 22 pages.
"Gym Book—Strength Training Planner, Logger and Analyzer", GymBookApp, Available Online at: <https://web.archive.org/web/20160401104508/https://gymbookapp.com/>, Apr. 1, 2016, 10 pages.
Invitation to Pay Additional Fees received for PCT Patent Application No. PCT/US2021/017736, mailed on Jun. 15, 2021, 14 pages.
Non-Final Office Action received for U.S. Appl. No. 17/030,318, dated Apr. 2, 2021, 28 pages.
Non-Final Office Action received for U.S. Appl. No. 17/030,318, dated Dec. 3, 2020, 22 pages.
Non-Final Office Action received for U.S. Appl. No. 17/030,321, dated Dec. 15, 2020, 25 pages.
Notice of Acceptance received for Australian Patent Application No. 2020256383, dated Aug. 3, 2021, 3 pages.
Notice of Allowance received for U.S. Appl. No. 15/608,848, dated Aug. 25, 2021, 9 pages.
Office Action received for Australian Patent Application No. 2020239743, dated Mar. 25, 2021, 8 pages.
Office Action received for Australian Patent Application No. 2020239748, dated Apr. 21, 2021, 6 pages.
Office Action received for Australian Patent Application No. 2020239752, dated Jun. 4, 2021, 8 pages.
Office Action received for Chinese Patent Application No. 201780034203.4, dated Jul. 14, 2021, 12 pages (5 pages of English Translation and 7 pages of Official Copy).
Search Report and Opinion received for Danish Patent Application No. PA202070612, dated Jun. 7, 2021, 9 pages.
Search Report and Opinion received for Danish Patent Application No. PA202070613, dated Jan. 22, 2021, 9 pages.
Search Report and Opinion received for Danish Patent Application No. PA202070615, dated Jan. 22, 2021, 9 pages.
Search Report and Opinion received for Danish Patent Application No. PA202070616, dated Feb. 3, 2021, 8 pages.
Corrected Notice of Allowance received for U.S. Appl. No. 16/378,136, dated Jun. 11, 2021, 2 pages.
Notice of Allowance received for U.S. Appl. No. 16/378,136, dated Jun. 3, 2021, 7 pages.
Office Action received for Australian Patent Application No. 2020256383, dated Jun. 4, 2021, 3 pages.
Office Action received for European Patent Application No. 20182116.2, dated May 25, 2021, 9 pages.
Office Action received for Japanese Patent Application No. 2020-115940, dated May 7, 2021, 3 pages (1 page of English Translation and 2 pages of Official Copy).
European Search Report received for European Patent Application No. 21168916.1, dated Jul. 14, 2021, 5 pages.
Notice of Allowance received for Korean Patent Application No. 10-2019-7025781, dated Jun. 29, 2021, 5 pages (2 pages of English Translation and 3 pages of Official Copy).
Notice of Allowance received for Korean Patent Application No. 10-2019-7033834, dated Jul. 3, 2021, 4 pages (2 page of English Translation and 2 pages of Official Copy).
Notice of Allowance received for U.S. Appl. No. 16/138,809, dated Jul. 20, 2021, 6 pages.
Notice of Allowance received for U.S. Appl. No. 16/820,383, dated Jul. 21, 2021, 11 pages.
Office Action received for Chinese Patent Application No. 201380081349.6, dated Jun. 2, 2021, 17 pages (8 pages of English Translation and 9 pages of Official Copy).
Office Action received for Chinese Patent Application No. 201910858933.7, dated Jun. 29, 2021, 8 pages (3 pages of English Translation and 5 pages of Official Copy).
Supplemental Notice of Allowance received for U.S. Appl. No. 15/627,069, dated Jul. 12, 2021, 2 pages.
Applicant-Initiated Interview Summary received for U.S. Appl. No. 16/894,309, dated Jun. 25, 2021, 4 pages.
Applicant-Initiated Interview Summary received for U.S. Appl. No. 17/031,859, dated Jun. 30, 2021, 4 pages.
Applicant-Initiated Interview Summary received for U.S. Appl. No. 17/031,874, dated Jun. 30, 2021, 4 pages.
Applicant-Initiated Interview Summary received for U.S. Appl. No. 17/192,161, dated Jun. 29, 2021, 4 pages.
Decision to Grant received for Danish Patent Application No. PA201670656, dated Jun. 21, 2021, 2 pages.
Decision to Grant received for German Patent Application No. 112015002326.7, dated Jun. 15, 2021, 10 pages (1 page of English Translation and 9 pages of Official Copy).
European Search Report received for European Patent Application No. 21165295.3, dated Jun. 18, 2021, 4 pages.
Notice of Allowance received for U.S. Appl. No. 15/627,069, dated Jun. 17, 2021, 14 pages.
Office Action received for Chinese Patent Application No. 202010606407.4, dated Jun. 2, 2021, 12 pages (5 pages of English Translation and 7 pages of Official Copy).
Office Action received for European Patent Application No. 19721883.7, dated Jun. 15, 2021, 9 pages.
Office Action received for European Patent Application No. 21165295.3, dated Jul. 1, 2021, 10 pages.
Communication of the Board of Appeal received for European Patent Application No. 15771747.1, dated Aug. 25, 2021, 9 pages.
Notice of Allowance received for Japanese Patent Application No. 2019-563407, dated Aug. 20, 2021, 4 pages (1 page of English Translation and 3 pages of Official Copy).
Notice of Allowance received for Korean Patent Application No. 10-2020-7026035, dated Aug. 23, 2021, 4 pages (2 page of English Translation and 2 pages of Official Copy).
Notice of Allowance received for U.S. Appl. No. 16/377,892, dated Sep. 9, 2021, 9 pages.
Office Action received for Australian Patent Application No. 2020239748, dated Sep. 1, 2021, 4 pages.
Office Action received for European Patent Application No. 21168916.1, dated Aug. 23, 2021, 8 pages.
Non-Final Office Action received for U.S. Appl. No. 17/192,161, dated May 13, 2021, 28 pages.
Notice of Allowance received for Chinese Patent Application No. 201680047983.1, dated Apr. 28, 2021, 3 pages (1 page of English Translation and 2 pages of Official Copy).
Notice of Allowance received for U.S. Appl. No. 16/377,892, dated May 24, 2021, 9 pages.
Summons to Oral Proceedings received for European Patent Application No. 15771747.1, mailed on Apr. 29, 2021, 8 pages.
Applicant-Initiated Interview Summary received for U.S. Appl. No. 17/192,161, dated Sep. 29, 2021, 3 pages.
Corrected Notice of Allowance received for U.S. Appl. No. 16/820,383, dated Oct. 5, 2021, 2 pages.
Final Office Action received for U.S. Appl. No. 17/030,318, dated Sep. 30, 2021, 28 pages.

(56) References Cited

OTHER PUBLICATIONS

International Search Report and Written Opinion received for PCT Patent Application No. PCT/US2021/017736, dated Sep. 2, 2021, 25 pages.
Non-Final Office Action received for U.S. Appl. No. 16/418,786, dated Oct. 4, 2021, 10 pages.
Office Action received for Danish Patent Application No. PA202070613, dated Sep. 30, 2021, 4 pages.
Office Action received for Danish Patent Application No. PA202070614, dated Sep. 28, 2021, 4 pages.
Notice of Allowance received for U.S. Appl. No. 16/378,136, dated Sep. 22, 2021, 7 pages.
Office Action received for Australian Patent Application No. 2020239743, dated Sep. 3, 2021, 4 pages.
Office Action received for Japanese Patent Application No. 2019-044107, dated Jul. 30, 2021, 9 pages (5 pages of English Translation and 4 pages of Official Copy).
Office Action received for Korean Patent Application No. 10-2021-7026284, dated Aug. 31, 2021, 10 pages (4 pages of English Translation and 6 pages of Official Copy).
Notice of Allowance received for Japanese Patent Application No. 2019-162293, dated Apr. 9, 2021, 4 pages (1 page of English Translation and 3 pages of Official Copy).
Office Action received for Danish Patent Application No. PA202170113, dated Apr. 15, 2021, 2 pages.
Non-Final Office Action received for U.S. Appl. No. 16/994,352, dated Jul. 30, 2021, 11 pages.
Notice of Allowance received for Japanese Patent Application No. 2020-000492, dated Jul. 16, 2021, 4 pages (1 page of English Translation and 3 pages of Official Copy).
Applicant-Initiated Interview Summary received for U.S. Appl. No. 16/377,892, dated Mar. 26, 2021, 2 pages.
Applicant-Initiated Interview Summary received for U.S. Appl. No. 16/378,136, dated Mar. 26, 2021, 2 pages.
Applicant-Initiated Interview Summary received for U.S. Appl. No. 16/418,786, dated Mar. 30, 2021, 4 pages.
Decision on Appeal received for Korean Patent Application No. 10-2019-7025538, dated Feb. 24, 2021, 20 pages (4 pages of English Translation and 16 pages of Official Copy).
Notice of Allowance received for Korean Patent Application No. 10-2019-7025538, dated Mar. 10, 2021, 5 pages (2 pages of English Translation and 3 pages of Official Copy).
Notice of Allowance received for U.S. Appl. No. 16/144,864, dated Mar. 30, 2021, 2 pages.
Notice of Allowance received for U.S. Appl. No. 16/820,383, dated Mar. 31, 2021, 11 pages.
Office Action received for European Patent Application No. 18727543.3, dated Mar. 26, 2021, 7 pages.
Search Report and Opinion received for Danish Patent Application No. PA202070815, dated Mar. 16, 2021, 8 pages.
Advisory Action received for U.S. Appl. No. 16/377,892, dated Apr. 9, 2021, 4 pages.
Advisory Action received for U.S. Appl. No. 16/378,136, dated Apr. 12, 2021, 4 pages.
Applicant Initiated Interview Summary received for U.S. Appl. No. 15/608,848, dated Apr. 13, 2021, 4 pages.
Final Office Action received for U.S. Appl. No. 17/031,859, dated Apr. 16, 2021, 14 pages.
Final Office Action received for U.S. Appl. No. 17/031,874, dated Apr. 16, 2021, 17 pages.
Notice of Acceptance received for Australian Patent Application No. 2021200787, dated Mar. 19, 2021, 3 pages.
Notice of Allowance received for U.S. Appl. No. 16/138,809, dated Apr. 16, 2021, 11 pages.
Office Action received for Japanese Patent Application No. 2018-184532, dated Mar. 1, 2021, 11 pages (6 pages of English Translation and 5 pages of Official Copy).
International Preliminary Report on Patentability received for PCT Patent Application No. PCT/US2020/035199, dated Dec. 16, 2021, 14 pages.

* cited by examiner

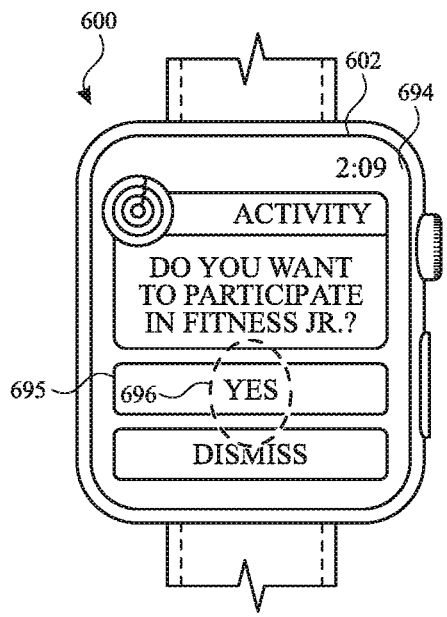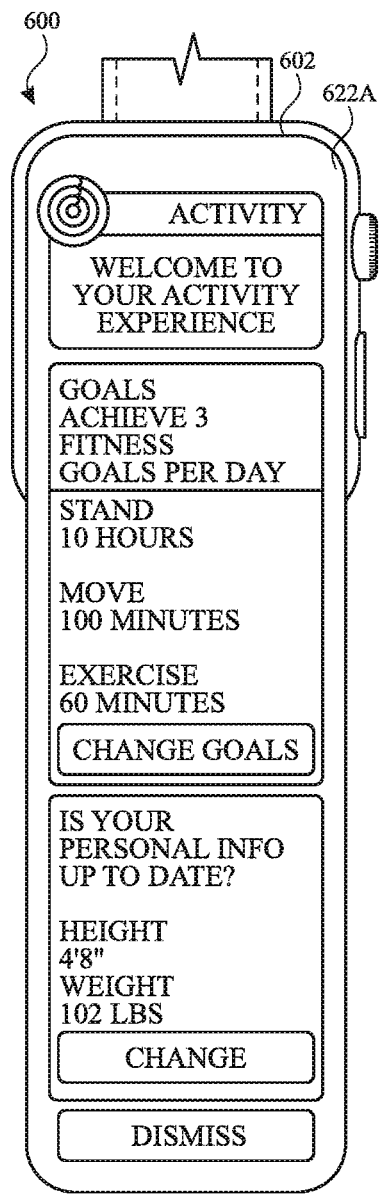
*FIG. 6T*
*FIG. 6U*

732
While the device is in a third respective device mode selected from a group consisting of the first device mode and the second device mode, receive, from a second external device, a second request to transition a device mode.

734
In response to receiving the second request to transition a device mode, display a second confirmation user interface that includes a second confirmation affordance and a first rejection affordance.

736
While displaying the second confirmation affordance, receive a first input.

738
In response to receiving the first input:

740
In accordance with a determination that the first input corresponds to the second confirmation affordance, transition to a second respective device mode selected from the group consisting of the first device mode and the second device mode, wherein the third respective device mode is different than the fourth respective device mode.

742
In accordance with a determination that the first input corresponds to the second confirmation affordance, remain in the third respective device mode.

744
While the device is in a fifth respective device mode selected from a group consisting of the first device mode and the second device mode, receive, via the input device, a third request to transition a device mode.

746
In response to receiving the third request to transition a device mode, transition to a sixth respective device mode selected from the group consisting of the first device mode and the second device mode, wherein the sixth respective device mode is different than the fifth respective device mode.

*FIG. 7C*

748
While the electronic device is operating in the first device mode, display a first physical activity tracking user interface that includes a first set of one or more activity tracking affordances that includes a first activity tracking affordance that, when selected, initiates a first activity tracking function.

750
While the electronic device is operating in the second device mode, display a second physical activity tracking user interface that includes a second set of one or more activity tracking affordances that includes the first activity tracking and a second activity tracking affordance that, when selected, initiates a second activity tracking function, wherein the second activity tracking affordance is not included in the first physical activity tracking user interface.

752
While the electronic device is operating in the first device mode, display a first settings user interface that includes a first set of one or more settings affordances that includes a first setting affordance that, when selected, alters a first setting.

754
While the electronic device is operating in the second device mode, display a second settings user interface that includes a second set of one or more settings affordances that includes the first setting affordance and a second setting affordance that, when selected, alters a second setting, wherein the second setting affordance is not included in the first settings user interface.

*FIG. 7D*

MULTI-MODAL ACTIVITY TRACKING USER INTERFACE

CROSS-REFERENCE TO RELATED APPLICATIONS

This application claims priority to U.S. Provisional Patent Application No. 62/856,048, filed Jun. 1, 2019, entitled "MULTI-MODAL ACTIVITY TRACKING USER INTERFACE," the content of which is hereby incorporated by reference in its entirety for all purposes.

FIELD

The present disclosure relates generally to computer user interfaces, and more specifically to user interfaces and techniques for monitoring fitness activity.

BACKGROUND

Users rely on portable multifunction devices for a variety of operations, including keeping time and running an assortment of software applications that enhance device functionality. A user may also want to access different types of information, such as various forms of physical activity-related data measured by the device, in order to further their health and fitness-related goals. Moreover, users vary in their physical characteristics.

BRIEF SUMMARY

Some techniques for monitoring fitness activity using electronic devices, however, are generally cumbersome and inefficient. For example, some existing techniques use a complex and time-consuming user interface, which may include multiple key presses or keystrokes. As another example, some existing techniques do not accommodate differences in characteristics of users, such as age. It is therefore desirable to allow the user to access physical activity-related data while keeping the interface simple and intuitive to use. Other existing techniques rely on the ability of a user to decipher complicated or confusing information, which may make it particularly difficult for some users (e.g., children) to meaningfully monitor their levels of physical activity. Existing techniques may be prone to error or require more time than necessary, wasting user time and device energy. This latter consideration is particularly important in battery-operated devices.

Accordingly, the present technique provides electronic devices with faster, more efficient methods and interfaces for monitoring fitness activity. Such methods and interfaces optionally complement or replace other methods for monitoring fitness activity. Such methods and interfaces reduce the cognitive burden on a user and produce a more efficient human-machine interface. For battery-operated computing devices, such methods and interfaces conserve power and increase the time between battery charges.

In accordance with some embodiments, a method performed at an electronic device including a display device and a first set of sensors is described. The method comprises: while the electronic device is operating in a first device mode, detecting a change in a first user physical characteristic from a first physical characteristic value to a second physical characteristic value; in response to detecting the change in the first user physical characteristic: in accordance with a determination that the second physical characteristic value satisfies a set of mode change criteria; and in accordance with a determination that the second physical characteristic value does not satisfy a set of mode change criteria, remaining in the first device mode; while the electronic device is operating in the first device mode: receiving first user activity data from the first set of sensors; subsequent to receiving the first user activity data, displaying a first activity user interface that includes a first activity metric based on the user activity data received from the first set of sensors; and while the electronic device is operating in the second device mode: receiving second user activity data from the first set of sensors; and subsequent to receiving the second user activity data, displaying a second activity user interface that includes a second activity metric, different from the first activity metric, based on the user activity data received from the first set of sensors.

In accordance with some embodiments, a non-transitory computer-readable storage medium storing one or more programs configured to be executed by one or more processors of an electronic device with a display device and a first set of sensors is described. The one or more programs include instructions for: while the electronic device is operating in a first device mode, detecting a change in a first user physical characteristic from a first physical characteristic value to a second physical characteristic value; in response to detecting the change in the first user physical characteristic: in accordance with a determination that the second physical characteristic value satisfies a set of mode change criteria; and in accordance with a determination that the second physical characteristic value does not satisfy a set of mode change criteria, remaining in the first device mode; while the electronic device is operating in the first device mode: receiving first user activity data from the first set of sensors; subsequent to receiving the first user activity data, displaying a first activity user interface that includes a first activity metric based on the user activity data received from the first set of sensors; and while the electronic device is operating in the second device mode: receiving second user activity data from the first set of sensors; and subsequent to receiving the second user activity data, displaying a second activity user interface that includes a second activity metric, different from the first activity metric, based on the user activity data received from the first set of sensors.

In accordance with some embodiments, a transitory computer-readable storage medium storing one or more programs configured to be executed by one or more processors of an electronic device with a display device and a first set of sensors is described. The one or more programs include instructions for: while the electronic device is operating in a first device mode, detecting a change in a first user physical characteristic from a first physical characteristic value to a second physical characteristic value; in response to detecting the change in the first user physical characteristic: in accordance with a determination that the second physical characteristic value satisfies a set of mode change criteria; and in accordance with a determination that the second physical characteristic value does not satisfy a set of mode change criteria, remaining in the first device mode; while the electronic device is operating in the first device mode: receiving first user activity data from the first set of sensors; subsequent to receiving the first user activity data, displaying a first activity user interface that includes a first activity metric based on the user activity data received from the first set of sensors; and while the electronic device is operating in the second device mode: receiving second user activity data from the first set of sensors; and subsequent to receiving the second user activity data, displaying a second activity user interface that includes a second activity metric, different from the first activity metric, based on the user activity data received from the first set of sensors.

In accordance with some embodiments, an electronic device is described. The electronic device comprises: a display device; a first set of sensors one or more processors; one or more processors; and memory storing one or more programs configured to be executed by the one or more processors, the one or more programs include instructions for: while the electronic device is operating in a first device mode, detecting a change in a first user physical characteristic from a first physical characteristic value to a second physical characteristic value; in response to detecting the change in the first user physical characteristic: in accordance with a determination that the second physical characteristic value satisfies a set of mode change criteria; and in accordance with a determination that the second physical characteristic value does not satisfy a set of mode change criteria, remaining in the first device mode; while the electronic device is operating in the first device mode: receiving first user activity data from the first set of sensors; subsequent to receiving the first user activity data, displaying a first activity user interface that includes a first activity metric based on the user activity data received from the first set of sensors; and while the electronic device is operating in the second device mode: receiving second user activity data from the first set of sensors and subsequent to receiving the second user activity data, displaying a second activity user interface that includes a second activity metric, different from the first activity metric, based on the user activity data received from the first set of sensors.

In accordance with some embodiments, an electronic device is described. The electronic device comprises: a display device; a first set of sensors; means, while the electronic device is operating in a first device mode, for detecting a change in a first user physical characteristic from a first physical characteristic value to a second physical characteristic value; means, in response to detecting the change in the first user physical characteristic, for: in accordance with a determination that the second physical characteristic value satisfies a set of mode change criteria, initiating a process to transition from the first device mode to a second device mode; and in accordance with a determination that the second physical characteristic value does not satisfy a set of mode change criteria, remaining in the first device mode; means, while the electronic device is operating in the first device mode, for: receiving first user activity data from the first set of sensors; means, subsequent to receiving the first user activity data, for displaying a first activity user interface that includes a first activity metric based on the user activity data received from the first set of sensors; and means, while the electronic device is operating in the second device mode, for: receiving second user activity data from the first set of sensors; and subsequent to receiving the second user activity data, displaying a second activity user interface that includes a second activity metric, different from the first activity metric, based on the user activity data received from the first set of sensors.

In accordance with some embodiments, a method performed at a first electronic device including a display device is described. The method comprises: receiving user activity data; and subsequent to receiving the user activity data and in accordance with a determination that the user activity data satisfies a first set of activity commentary display criteria, displaying, via the display device, a first user interface, including: in accordance with a determination that a value of a user characteristic satisfies a set of first commentary criteria, a first activity commentary based on the user activity data; and in accordance with a determination that the value of the user characteristic satisfies a set of second commentary criteria, a second activity commentary based on the user activity data, the second activity commentary different from the first commentary.

In accordance with some embodiments, a non-transitory computer-readable storage medium storing one or more programs configured to be executed by one or more processors of a first electronic device that includes a display device is described. The one or more programs include instructions for: receiving user activity data; and subsequent to receiving the user activity data and in accordance with a determination that the user activity data satisfies a first set of activity commentary display criteria, displaying, via the display device, a first user interface, including: in accordance with a determination that a value of a user characteristic satisfies a set of first commentary criteria, a first activity commentary based on the user activity data; and in accordance with a determination that the value of the user characteristic satisfies a set of second commentary criteria, a second activity commentary based on the user activity data, the second activity commentary different from the first commentary.

In accordance with some embodiments, a transitory computer-readable storage medium storing one or more programs configured to be executed by one or more processors of a first electronic device that includes a display device is described. The one or more programs include instructions for: receiving user activity data; and subsequent to receiving the user activity data and in accordance with a determination that the user activity data satisfies a first set of activity commentary display criteria, displaying, via the display device, a first user interface, including: in accordance with a determination that a value of a user characteristic satisfies a set of first commentary criteria, a first activity commentary based on the user activity data; and in accordance with a determination that the value of the user characteristic satisfies a set of second commentary criteria, a second activity commentary based on the user activity data, the second activity commentary different from the first commentary.

In accordance with some embodiments, a first electronic device is described. The first electronic device comprises: a display device; one or more processors; and memory storing one or more programs configured to be executed by the one or more processors, the one or more programs including instructions for: receiving user activity data; and subsequent to receiving the user activity data and in accordance with a determination that the user activity data satisfies a first set of activity commentary display criteria, displaying, via the display device, a first user interface, including: in accordance with a determination that a value of a user characteristic satisfies a set of first commentary criteria, a first activity commentary based on the user activity data; and in accordance with a determination that the value of the user characteristic satisfies a set of second commentary criteria, a second activity commentary based on the user activity data, the second activity commentary different from the first commentary.

In accordance with some embodiments, a first electronic device is described. The first electronic device comprises: a display device; means for receiving user activity data; and means, subsequent to receiving the user activity data and in accordance with a determination that the user activity data satisfies a first set of activity commentary display criteria, for displaying, via the display device, a first user interface, including: in accordance with a determination that a value of a user characteristic satisfies a set of first commentary criteria, a first activity commentary based on the user activity data; and in accordance with a determination that the value of the user characteristic satisfies a set of second commentary criteria, a second activity commentary based on the user activity data, the second activity commentary different from the first commentary.

Executable instructions for performing these functions are, optionally, included in a non-transitory computer-readable storage medium or other computer program product configured for execution by one or more processors. Executable instructions for performing these functions are, optionally, included in a transitory computer-readable storage medium or other computer program product configured for execution by one or more processors.

Thus, devices are provided with faster, more efficient methods and interfaces for monitoring fitness activity, thereby increasing the effectiveness, efficiency, and user satisfaction with such devices. Such methods and interfaces may complement or replace other methods for monitoring fitness activity.

DESCRIPTION OF THE FIGURES

For a better understanding of the various described embodiments, reference should be made to the Description of Embodiments below, in conjunction with the following drawings in which like reference numerals refer to corresponding parts throughout the figures.

FIGS. 7A-7D illustrate a flow diagram depicting a method for providing user interfaces in accordance with some embodiments.

DESCRIPTION OF EMBODIMENTS

Figure 1A:
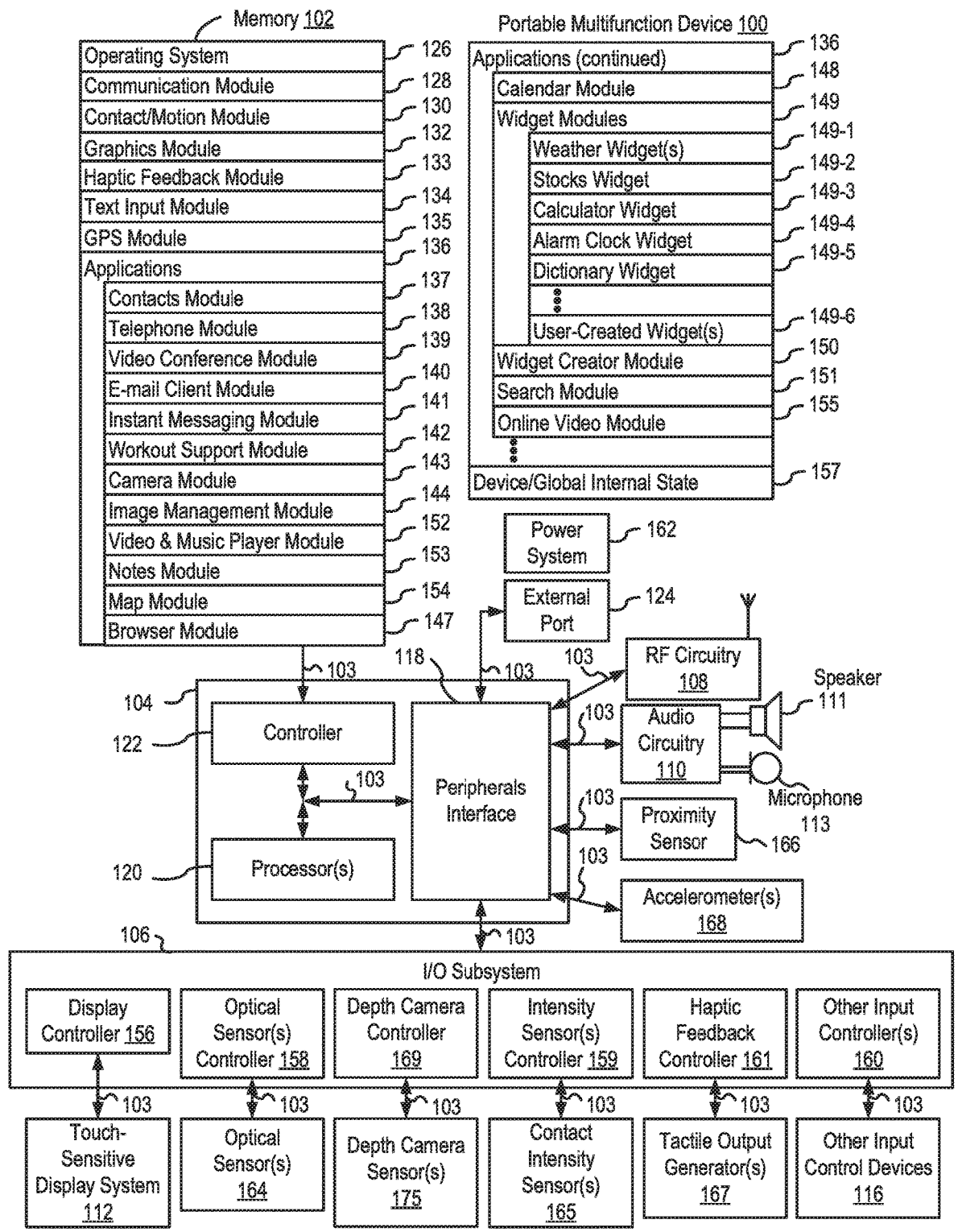
FIG. 1A is a block diagram illustrating a portable multifunction device with a touch-sensitive display in accordance with some embodiments.

The following description sets forth exemplary methods, parameters, and the like. It should be recognized, however, that such description is not intended as a limitation on the scope of the present disclosure but is instead provided as a description of exemplary embodiments.

There is a need for electronic devices that provide efficient methods and interfaces for monitoring fitness activity. For example, a user that seeks to increase their level of physical activity in order obtain the associated health benefits (e.g., prevention and improved management of health conditions such as high blood pressure, type 2 diabetes, depression and anxiety, arthritis, etc.) often relies on tracking progress toward their goals mentally, manually (via pen and pad), or using devices that provide inaccurate data and worse, require navigation of cumbersome interfaces to access such data. More efficient techniques can reduce the cognitive burden on a user who accesses fitness activity data, thereby enhancing productivity and the likelihood of reaching their fitness and health goals. Further, such techniques can reduce processor and battery power otherwise wasted on redundant user inputs.

Below, FIGS. 1A-1B, 2, 3, 4A-4B, and 5A-5H provide a description of exemplary devices for performing the techniques for monitoring fitness activity. FIGS. 6A-6W illustrate exemplary user interfaces for monitoring fitness activity. FIGS. 7A-7D are a flow diagram illustrating methods of monitoring fitness activity in accordance with some embodiments. The user interfaces in FIGS. 6A-6W are used to illustrate the processes described below, including the processes in FIGS. 7A-7D. FIGS. 8A-8H illustrate exemplary user interfaces for providing dynamic activity commentary. FIGS. 9A-9B are a flow diagrams illustrating methods of providing dynamic activity commentary in accordance with some embodiments. The user interfaces in FIGS. 8A-8H are used to illustrate the processes described below, including the processes in FIGS. 9A-9B. Although the following description uses terms "first," "second," etc. to describe various elements, these elements should not be limited by the terms. These terms are only used to distinguish one element from another. For example, a first touch could be termed a second touch, and, similarly, a second touch could be termed a first touch, without departing from the scope of the various described embodiments. The first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as PDA and/or music player functions. Exemplary embodiments of portable multifunction devices include, without limitation, the iPhone, iPod Touch®, and iPad® devices from Apple Inc. of Cupertino, Calif. Other portable electronic devices, such as laptops or tablet computers with touch-sensitive surfaces (e.g., touch screen displays and/or touchpads), are, optionally, used. It should also be understood that, in some embodiments, the device is not a portable communications device, but is a desktop computer with a touch-sensitive surface (e.g., a touch screen display and/or a touchpad). In some embodiments, the electronic device is a computer system that is in communication (e.g., via wireless communication, via wired communication) with a display generation component. The display generation component is configured to provide visual output, such as display via a CRT display, display via an LED display, or display via image projection. In some embodiments, the display generation component is integrated with the computer system. In some embodiments, the display generation component is separate from the computer system. As used herein, "displaying" content includes causing to display the content (e.g., video data rendered or decoded by display controller 156) by transmitting, via a wired or wireless connection, data (e.g., image data or video data) to an integrated or external display generation component to visually produce the content.

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system."

Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that may otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs and/or sets of instructions stored in memory 102 to perform various functions for device 100 and to process data. In some embodiments, peripherals interface 118, CPU 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, depth camera controller 169, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some alternate embodiments, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206, FIG. 2). In some embodiments, the electronic device is a computer system that is in communication (e.g., via wireless communication, via wired communication) with one or more input devices. In some embodiments, the one or more input devices include a touch-sensitive surface (e.g., a trackpad, as part of a touch-sensitive display). In some embodiments, the one or more input devices include one or more camera sensors (e.g., one or more optical sensors 164 and/or one or more depth camera sensors 175), such as for tracking a user's gestures (e.g., hand gestures) as input. In some embodiments, the one or more input devices are integrated with the computer system. In some embodiments, the one or more input devices are separate from the computer system.

A quick press of the push button optionally disengages a lock of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) optionally turns power to device 100 on or off. The functionality of one or more of the buttons are, optionally, user-customizable. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output optionally includes graphics, text, icons, video, and any combination thereof (collectively termed "graphics"). In some embodiments, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Touch screen 112 optionally uses LCD (liquid crystal display) technology, LPD (light emitting polymer display) technology, or LED (light emitting diode) technology, although other display technologies are used in other embodiments. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, Calif.

A touch-sensitive display in some embodiments of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

Touch screen 112 optionally has a video resolution in excess of 100 dpi. In some embodiments, the touch screen has a video resolution of approximately 160 dpi. The user optionally makes contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad for activating or deactivating particular functions. In some embodiments, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some embodiments, an optical sensor is located on the back of device 100, opposite touch screen display 112 on the front of the device so that the touch screen display is enabled for use as a viewfinder for still and/or video image acquisition. In some embodiments, an optical sensor is located on the front of the device so that the user's image is, optionally, obtained for video conferencing while the user views the other video conference participants on the touch screen display. In some embodiments, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more depth camera sensors 175. FIG. 1A shows a depth camera sensor coupled to depth camera controller 169 in I/O subsystem 106. Depth camera sensor 175 receives data from the environment to create a three dimensional model of an object (e.g., a face) within a scene from a viewpoint (e.g., a depth camera sensor). In some embodiments, in conjunction with imaging module 143 (also called a camera module), depth camera sensor 175 is optionally used to determine a depth map of different portions of an image captured by the imaging module 143. In some embodiments, a depth camera sensor is located on the front of device 100 so that the user's image with depth information is, optionally, obtained for video conferencing while the user views the other video conference participants on the touch screen display and to capture selfies with depth map data. In some embodiments, the depth camera sensor 175 is located on the back of device, or on the back and the front of the device 100. In some embodiments, the position of depth camera sensor 175 can be changed by the user (e.g., by rotating the lens and the sensor in the device housing) so that a depth camera sensor 175 is used along with the touch screen display for both video conferencing and still and/or video image acquisition.

In some embodiments, a depth map (e.g., depth map image) contains information (e.g., values) that relates to the distance of objects in a scene from a viewpoint (e.g., a camera, an optical sensor, a depth camera sensor). In one embodiment of a depth map, each depth pixel defines the position in the viewpoint's Z-axis where its corresponding two-dimensional pixel is located. In some embodiments, a depth map is composed of pixels wherein each pixel is defined by a value (e.g., 0-255). For example, the "0" value represents pixels that are located at the most distant place in a "three dimensional" scene and the "255" value represents pixels that are located closest to a viewpoint (e.g., a camera, an optical sensor, a depth camera sensor) in the "three dimensional" scene. In other embodiments, a depth map represents the distance between an object in a scene and the plane of the viewpoint. In some embodiments, the depth map includes information about the relative depth of various features of an object of interest in view of the depth camera (e.g., the relative depth of eyes, nose, mouth, ears of a user's face). In some embodiments, the depth map includes information that enables the device to determine contours of the object of interest in a z direction.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; Ser. No. 11/240,788, "Proximity Detector In Handheld Device"; Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals," which are hereby incorporated by reference in their entirety. In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112, which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer and a GPS (or GLONASS or other global navigation system) receiver for obtaining information concerning the location and orientation (e.g., portrait or landscape) of device 100.

Figure 3:
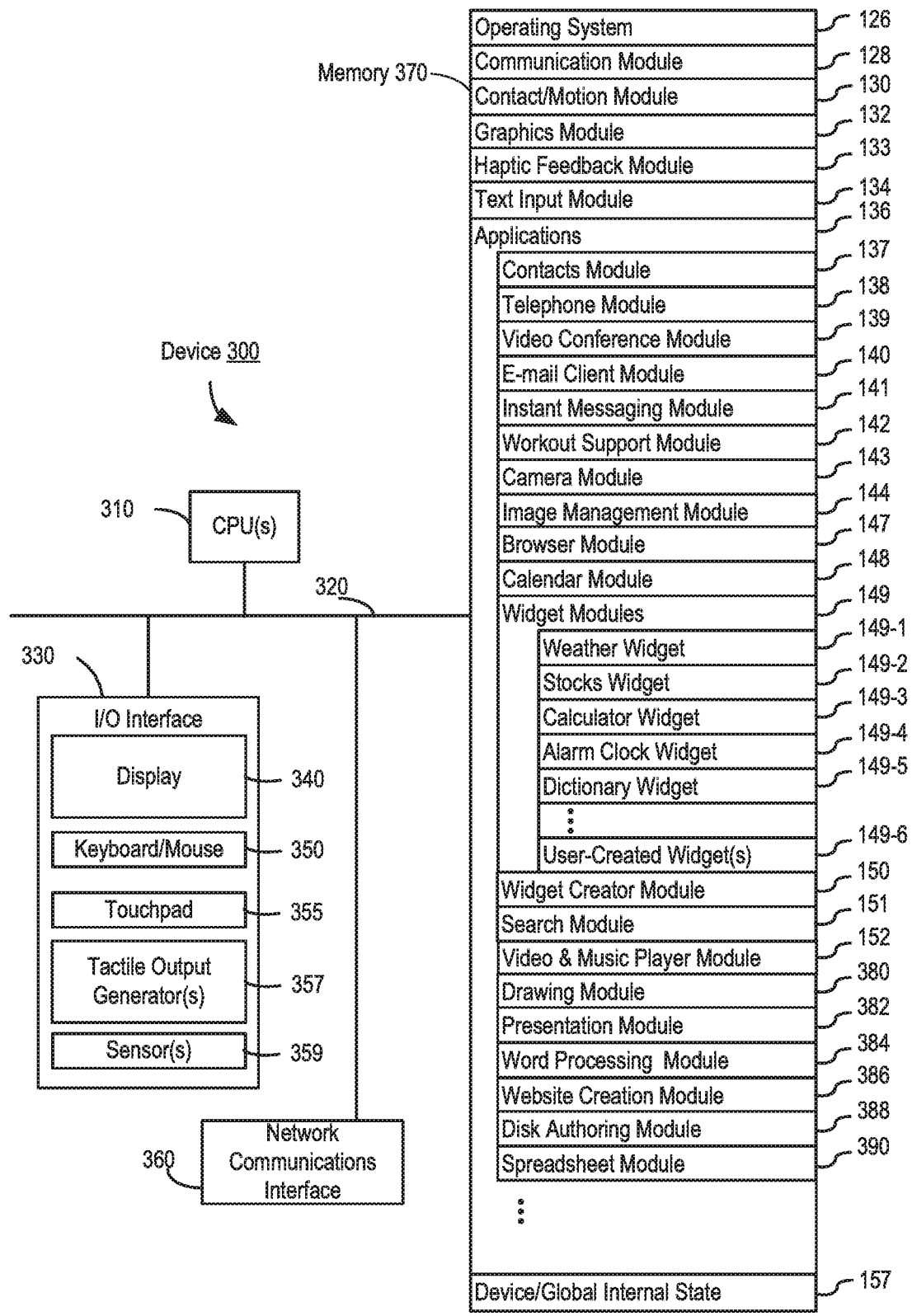
FIG. 3 is a block diagram of an exemplary multifunction device with a display and a touch-sensitive surface in accordance with some embodiments.

In some embodiments, the software components stored in memory 102 include operating system 126, communication module (or set of instructions) 128, contact/motion module (or set of instructions) 130, graphics module (or set of instructions) 132, text input module (or set of instructions) 134, Global Positioning System (GPS) module (or set of instructions) 135, and applications (or sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIREWIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts 137, e-mail 140, IM 141, browser 147, and any other application that needs text input).

GPS module 135 determines the location of the device and provides this information for use in various applications (e.g., to telephone 138 for use in location-based dialing; to camera 143 as picture/video metadata; and to applications that provide location-based services such as weather widgets, local yellow page widgets, and map/navigation widgets).

Applications 136 optionally include the following modules (or sets of instructions), or a subset or superset thereof:

Contacts module 137 (sometimes called an address book or contact list);

Telephone module 138;
Video conference module 139;
E-mail client module 140;
Instant messaging (IM) module 141;
Workout support module 142;
Camera module 143 for still and/or video images;
Image management module 144;
Video player module;
Music player module;
Browser module 147;
Calendar module 148;
Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
Widget creator module 150 for making user-created widgets 149-6;
Search module 151;
Video and music player module 152, which merges video player module and music player module,
Notes module 153;
Map module 154; and/or
Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference module 139, e-mail 140, or IM 141; and so forth.

In conjunction with RF circuitry 108, audio circuitry 110, speaker 111, microphone 113, touch screen 112, display controller 156, contact/motion module 130, graphics module 132, and text input module 134, telephone module 138 are optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo!Widgets).

In conjunction with RF circuitry 108, touch screen 112, display controller 156, contact/motion module 130, graphics module 132, text input module 134, and browser module 147, the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.).

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs, procedures, or modules, and thus various subsets of these modules are, optionally, combined or otherwise rearranged in various embodiments. For example, video player module is, optionally, combined with music player module into a single module (e.g., video and music player module 152, FIG. 1A). In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
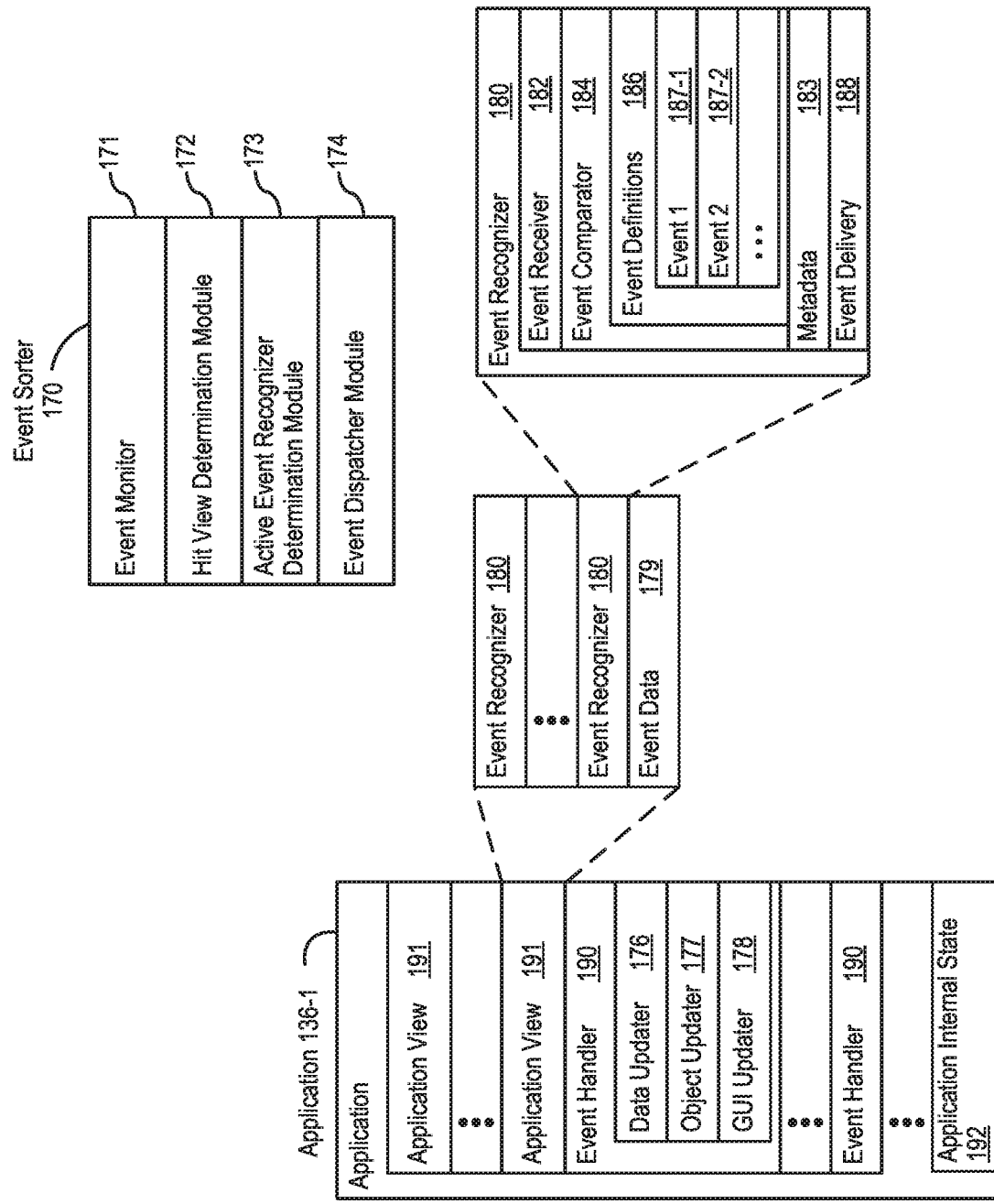
FIG. 1B is a block diagram illustrating exemplary components for event handling in accordance with some embodiments.

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180).

In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit or a higher level object from which application 136-1 inherits methods and other properties. In some embodiments, a respective event handler 190 includes one or more of: data updater 176, object updater 177, GUI updater 178, and/or event data 179 received from event sorter 170. Event handler 190 optionally utilizes or calls data updater 176, object updater 177, or GUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (187) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definition 187 includes a definition of an event for a respective user-interface object. In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

Figure 2:
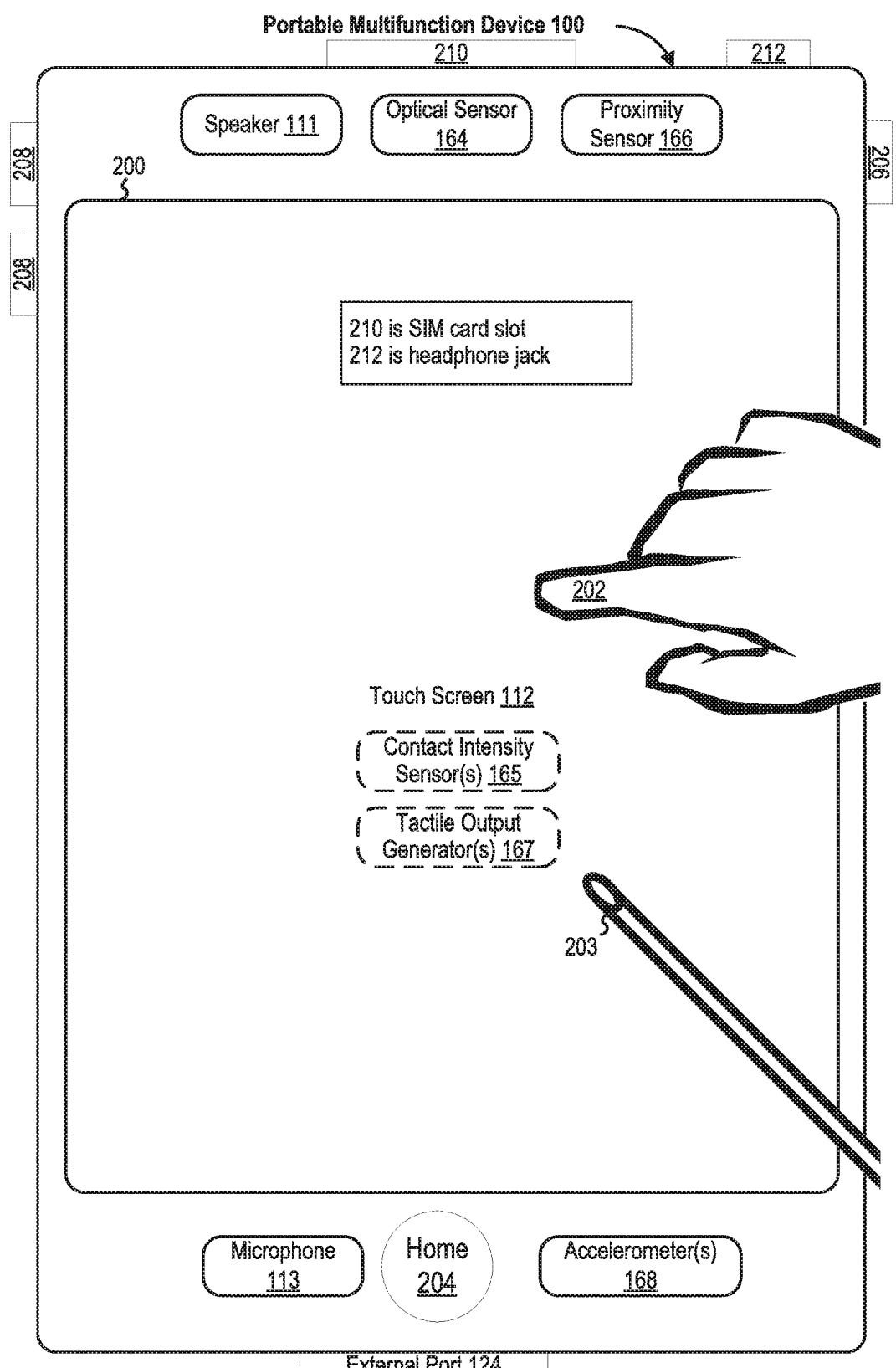
FIG. 2 illustrates a portable multifunction device having a touch screen in accordance with some embodiments.

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 is, optionally, stored in one or more of the previously mentioned memory devices. Each of the above-identified modules corresponds to a set of instructions for performing a function described above. The above-identified modules or programs (e.g., sets of instructions) need not be implemented as separate software programs, procedures, or modules, and thus various subsets of these modules are, optionally, combined or otherwise rearranged in various embodiments. In some embodiments, memory 370 optionally stores a subset of the modules and data structures identified above. Furthermore, memory 370 optionally stores additional modules and data structures not described above.

Attention is now directed towards embodiments of user interfaces that are, optionally, implemented on, for example, portable multifunction device 100.

Figure 4A:
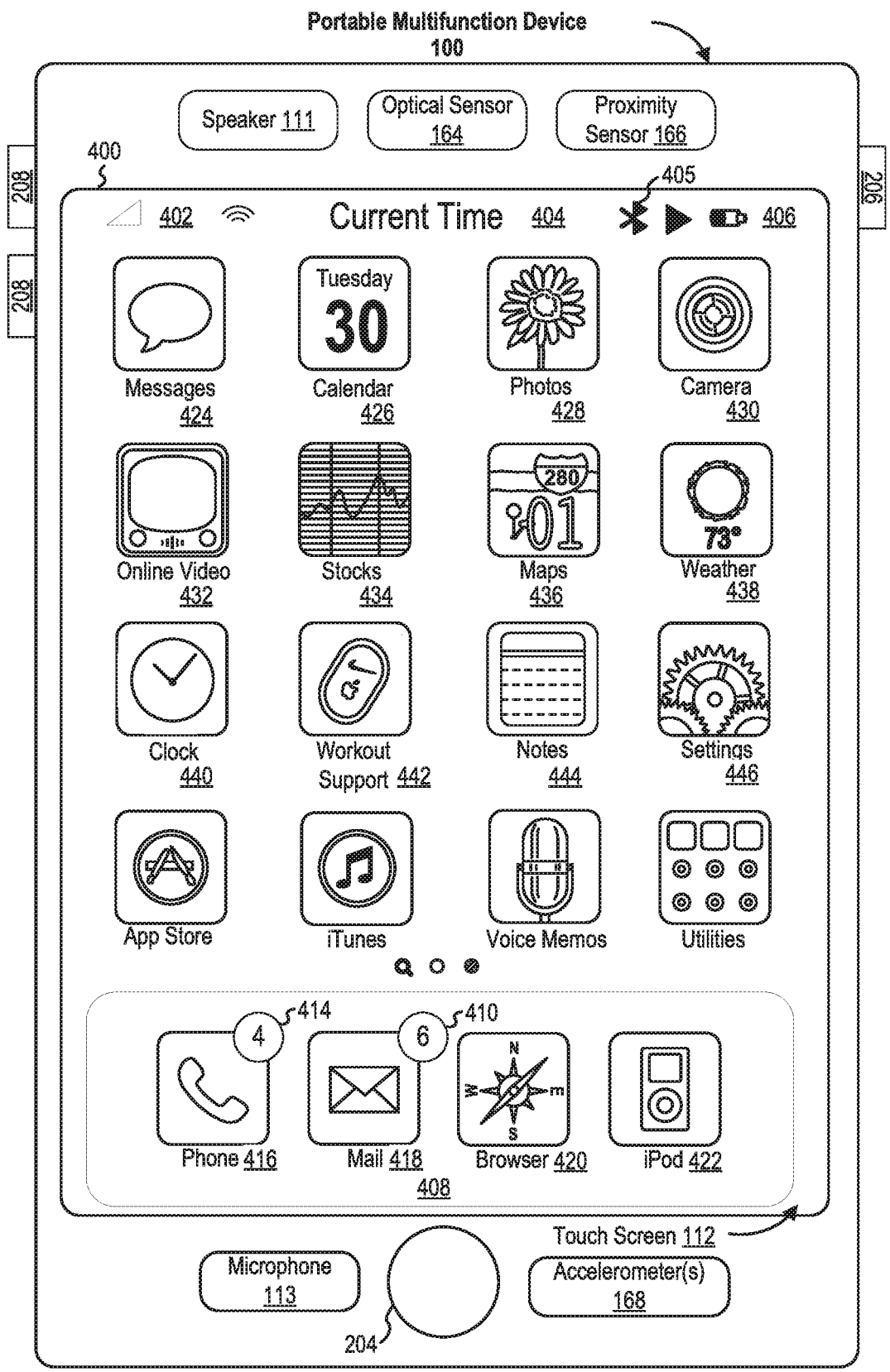
FIG. 4A illustrates an exemplary user interface for a menu of applications on a portable multifunction device in accordance with some embodiments.

FIG. 4A illustrates an exemplary user interface for a menu of applications on portable multifunction device 100 in accordance with some embodiments. Similar user interfaces are, optionally, implemented on device 300. In some embodiments, user interface 400 includes the following elements, or a subset or superset thereof:

Signal strength indicator(s) 402 for wireless communication(s), such as cellular and Wi-Fi signals;
Time 404;
Bluetooth indicator 405;
Battery status indicator 406;
Tray 408 with icons for frequently used applications, such as:
  Icon 416 for telephone module 138, labeled "Phone," which optionally includes an indicator 414 of the number of missed calls or voicemail messages;
  Icon 418 for e-mail client module 140, labeled "Mail," which optionally includes an indicator 410 of the number of unread e-mails;
  Icon 420 for browser module 147, labeled "Browser;" and
  Icon 422 for video and music player module 152, also referred to as iPod (trademark of Apple Inc.) module 152, labeled "iPod;" and
Icons for other applications, such as:
  Icon 424 for IM module 141, labeled "Messages;"
  Icon 426 for calendar module 148, labeled "Calendar;"
  Icon 428 for image management module 144, labeled "Photos;"
  Icon 430 for camera module 143, labeled "Camera;"
  Icon 432 for online video module 155, labeled "Online Video;"
  Icon 434 for stocks widget 149-2, labeled "Stocks;"
  Icon 436 for map module 154, labeled "Maps;"
  Icon 438 for weather widget 149-1, labeled "Weather;"
  Icon 440 for alarm clock widget 149-4, labeled "Clock;"
  Icon 442 for workout support module 142, labeled "Workout Support;"
  Icon 444 for notes module 153, labeled "Notes;" and
  Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 is labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

Figure 4B:
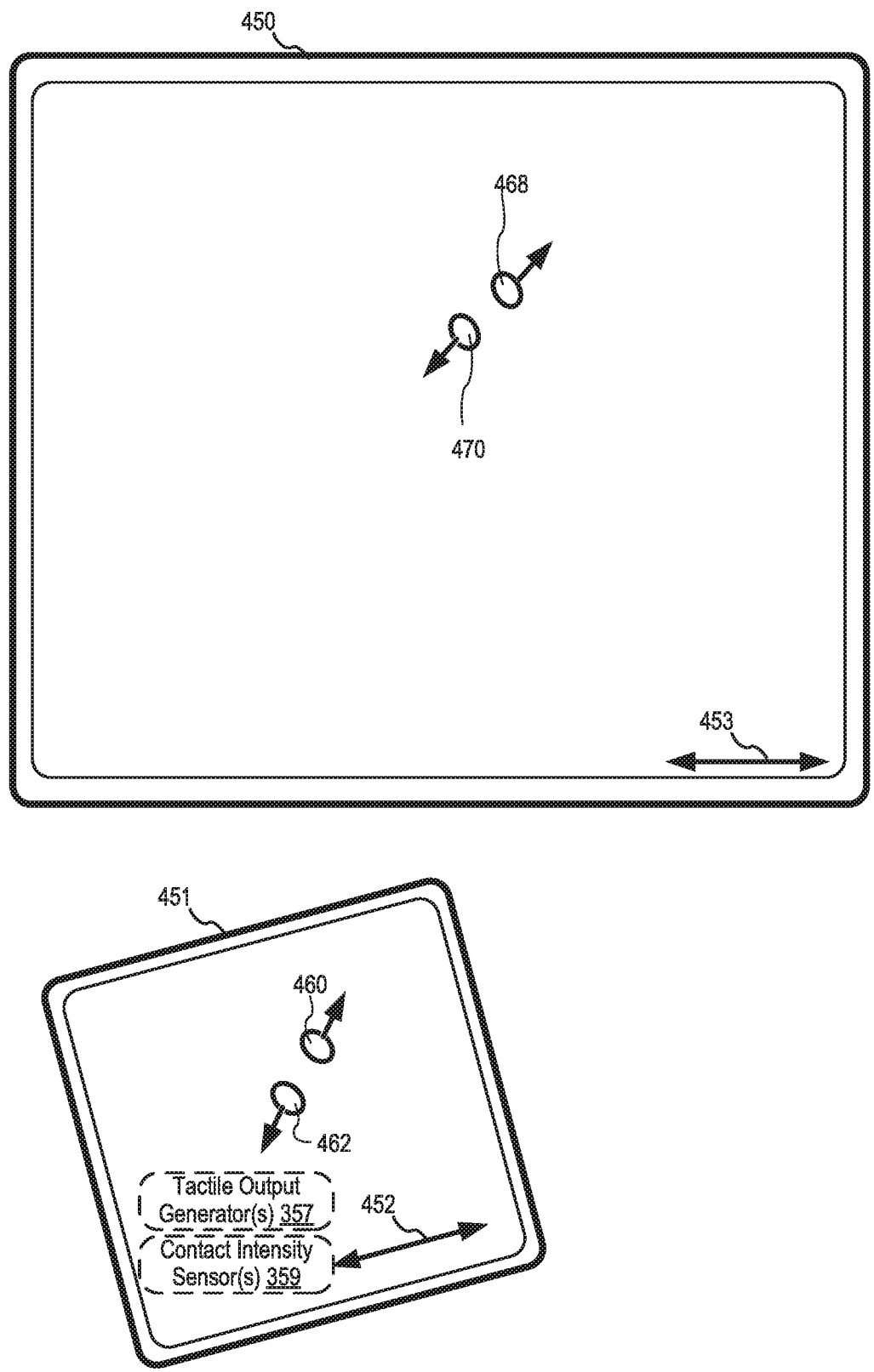
FIG. 4B illustrates an exemplary user interface for a multifunction device with a touch-sensitive surface that is separate from the display in accordance with some embodiments.

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples that follow will be given with reference to inputs on touch screen display 112 (where the touch-sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 5A:
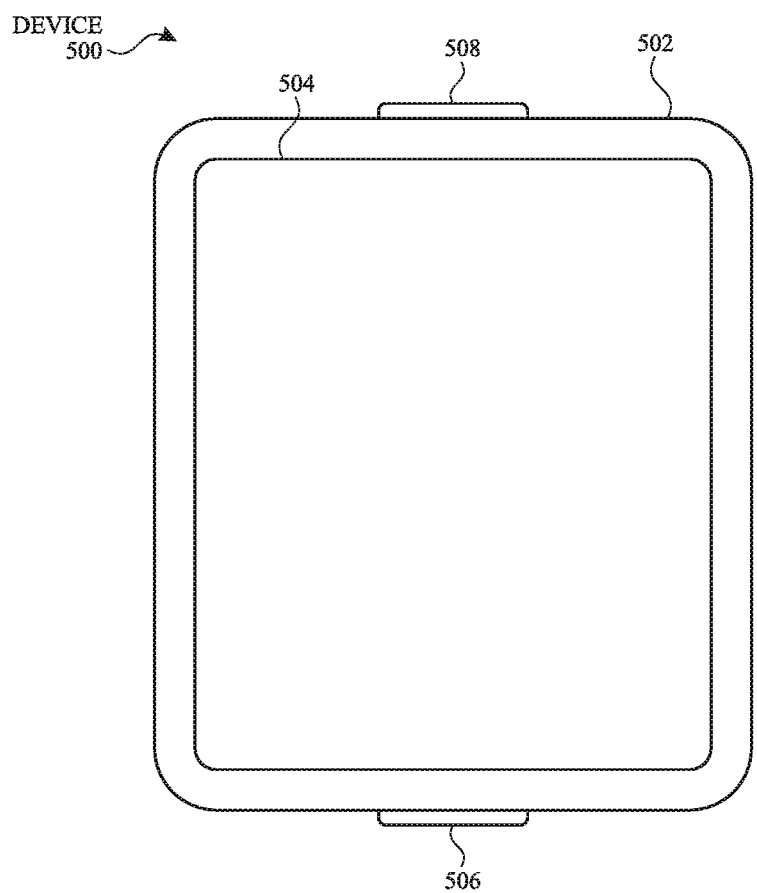
FIG. 5A illustrates a personal electronic device in accordance with some embodiments.
Figure 6A:
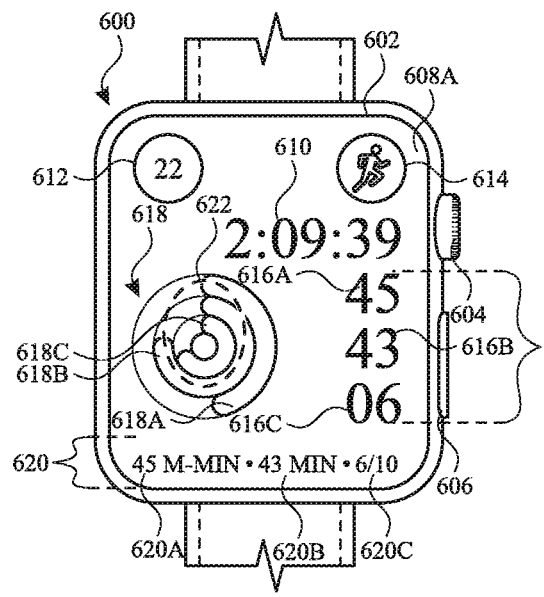
FIGS. 6A-6W illustrate exemplary user interfaces for monitoring fitness activity.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504. Alternatively, or in addition to touch screen 504, device 500 has a display and a touch-sensitive surface. As with devices 100 and 300, in some embodiments, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Exemplary techniques for detecting and processing touch intensity are found, for example, in related applications: International Patent Application Serial No. PCT/US2013/040061, titled "Device, Method, and Graphical User Interface for Displaying User Interface Objects Corresponding to an Application," filed May 8, 2013, published as WIPO Publication No. WO/2013/169849, and International Patent Application Serial No. PCT/US2013/069483, titled "Device, Method, and Graphical User Interface for Transitioning Between Touch Input to Display Output Relationships," filed Nov. 11, 2013, published as WIPO Publication No. WO/2014/105276, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms permit device 500 to be worn by a user.

Figure 5B:
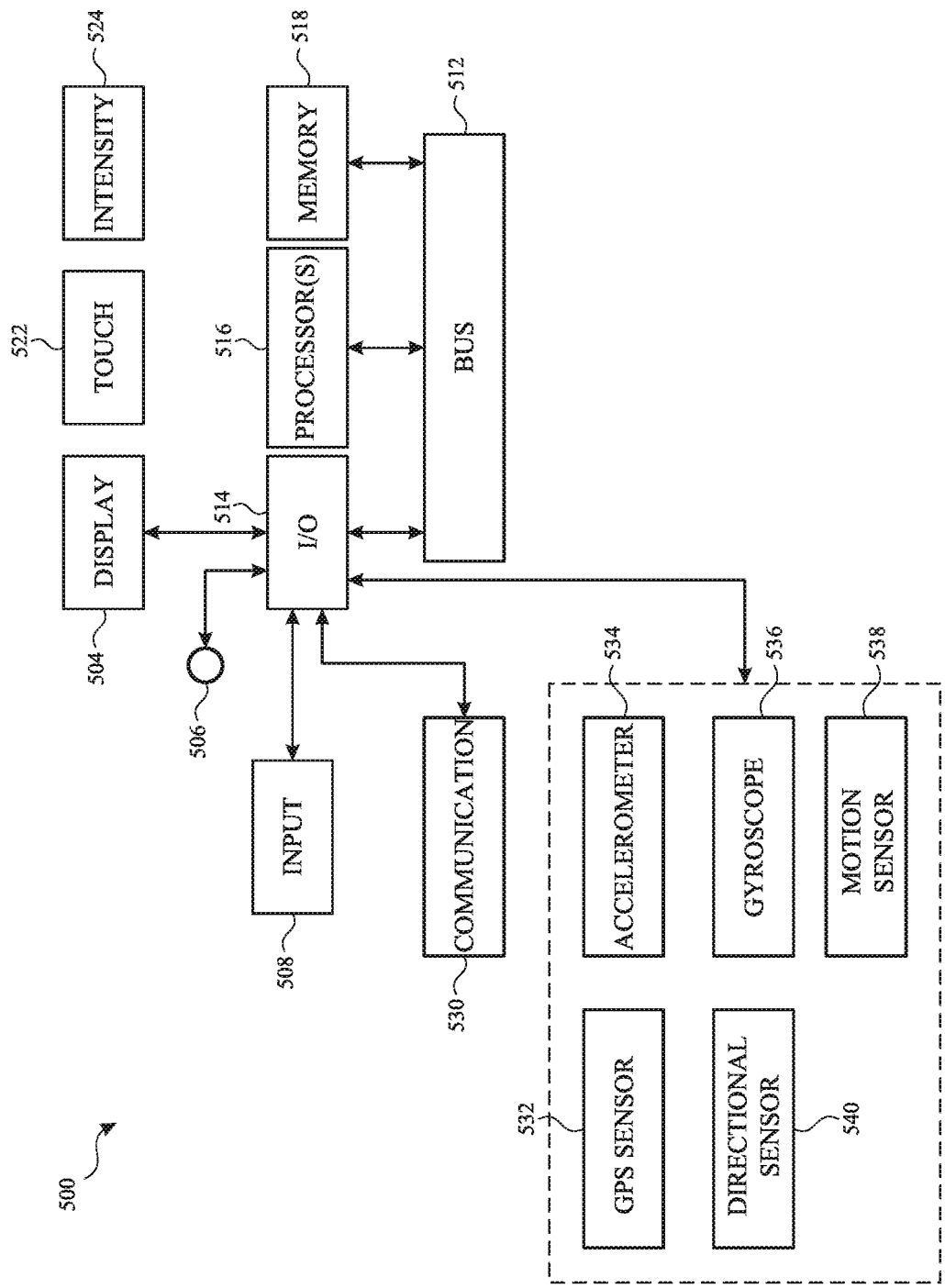
FIG. 5B is a block diagram illustrating a personal electronic device in accordance with some embodiments.

FIG. 5B depicts exemplary personal electronic device 500. In some embodiments, device 500 can include some or all of the components described with respect to FIGS. 1A, 1B, and 3. Device 500 has bus 512 that operatively couples I/O section 514 with one or more computer processors 516 and memory 518. I/O section 514 can be connected to display 504, which can have touch-sensitive component 522 and, optionally, intensity sensor 524 (e.g., contact intensity sensor). In addition, I/O section 514 can be connected with communication unit 530 for receiving application and operating system data, using Wi-Fi, Bluetooth, near field communication (NFC), cellular, and/or other wireless communication techniques. Device 500 can include input mechanisms 506 and/or 508. Input mechanism 506 is, optionally, a rotatable input device or a depressible and rotatable input device, for example. Input mechanism 508 is, optionally, a button, in some examples.

Input mechanism 508 is, optionally, a microphone, in some examples. Personal electronic device 500 optionally includes various sensors, such as GPS sensor 532, accelerometer 534, directional sensor 540 (e.g., compass), gyroscope 536, motion sensor 538, and/or a combination thereof, all of which can be operatively connected to I/O section 514.

Memory 518 of personal electronic device 500 can include one or more non-transitory computer-readable storage mediums, for storing computer-executable instructions, which, when executed by one or more computer processors 516, for example, can cause the computer processors to perform the techniques described below, including processes 700 and 900 (FIGS. 7A-7D and 9A-9B). A computer-readable storage medium can be any medium that can tangibly contain or store computer-executable instructions for use by or in connection with the instruction execution system, apparatus, or device. In some examples, the storage medium is a transitory computer-readable storage medium. In some examples, the storage medium is a non-transitory computer-readable storage medium. The non-transitory computer-readable storage medium can include, but is not limited to, magnetic, optical, and/or semiconductor storages. Examples of such storage include magnetic disks, optical discs based on CD, DVD, or Blu-ray technologies, as well as persistent solid-state memory such as flash, solid-state drives, and the like. Personal electronic device 500 is not limited to the components and configuration of FIG. 5B, but can include other or additional components in multiple configurations.

As used here, the term "affordance" refers to a user-interactive graphical user interface object that is, optionally, displayed on the display screen of devices 100, 300, and/or 500 (FIGS. 1A, 3, and 5A-5B). For example, an image (e.g., icon), a button, and text (e.g., hyperlink) each optionally constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider, or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some embodiments, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally, based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some embodiments, the duration of the contact is used in determining the characteristic intensity (e.g., when the characteristic intensity is an average of the intensity of the contact over time). In some embodiments, the characteristic intensity is compared to a set of one or more intensity thresholds to determine whether an operation has been performed by a user. For example, the set of one or more intensity thresholds optionally includes a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation. In some embodiments, a comparison between the characteristic intensity and one or more thresholds is used to determine whether or not to perform one or more operations (e.g., whether to perform a respective operation or forgo performing the respective operation), rather than being used to determine whether to perform a first operation or a second operation.

Figure 5C:
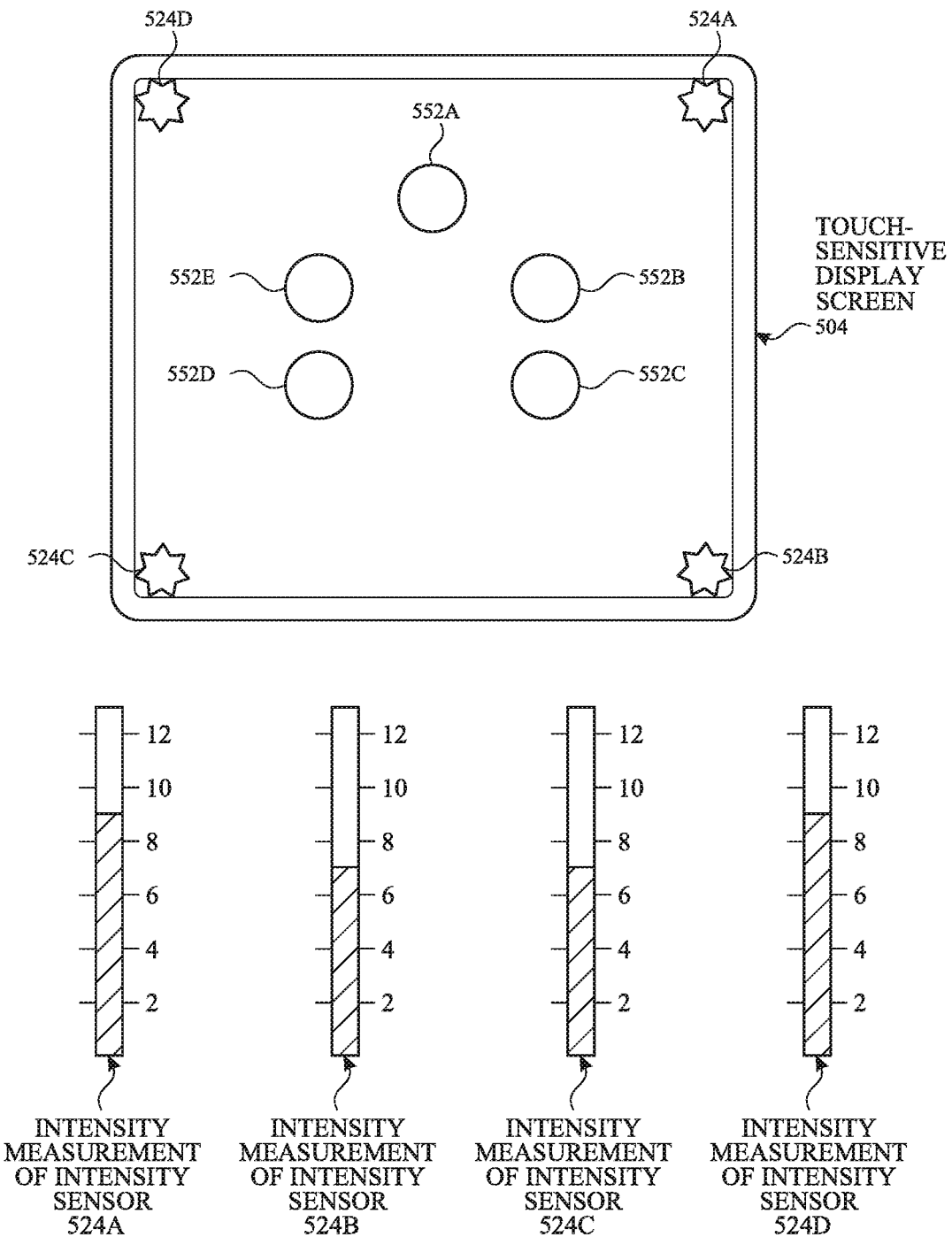
FIGS. 5C-5D illustrate exemplary components of a personal electronic device having a touch-sensitive display and intensity sensors in accordance with some embodiments.
Figure 5D:
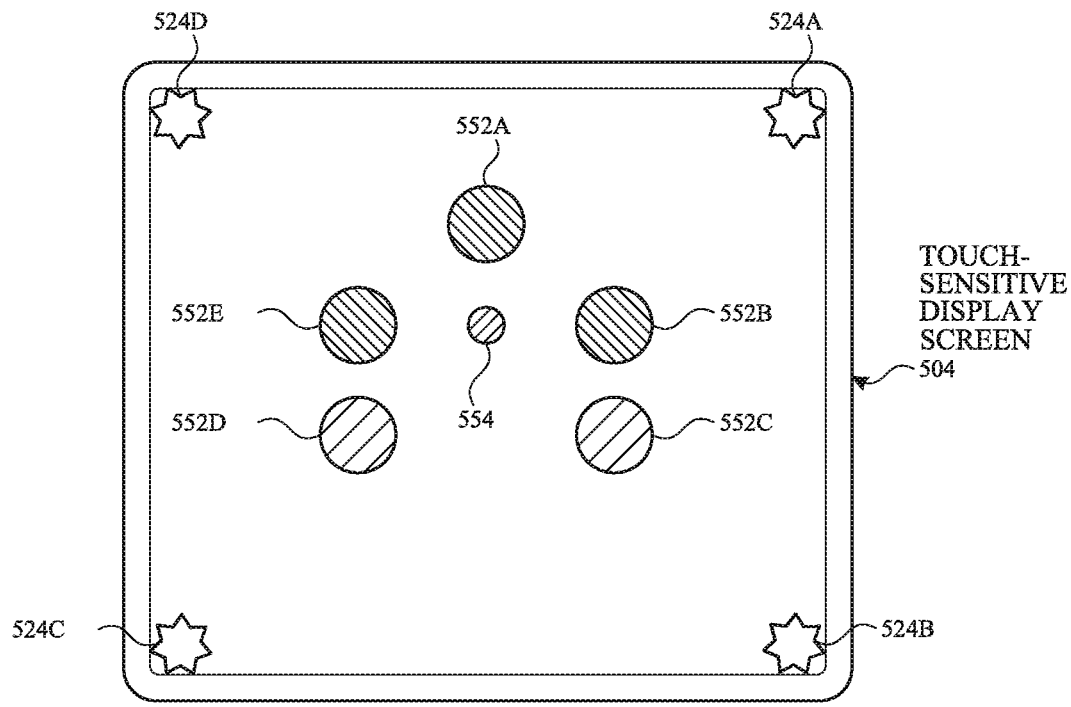
Figure 5D:
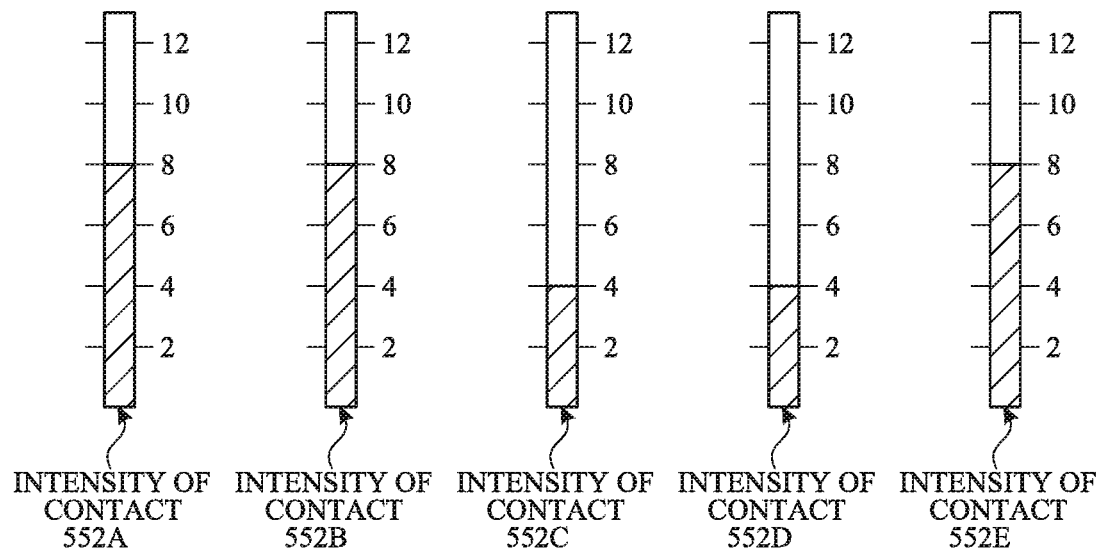

FIG. 5C illustrates detecting a plurality of contacts 552A-552E on touch-sensitive display screen 504 with a plurality of intensity sensors 524A-524D. FIG. 5C additionally includes intensity diagrams that show the current intensity measurements of the intensity sensors 524A-524D relative to units of intensity. In this example, the intensity measurements of intensity sensors 524A and 524D are each 9 units of intensity, and the intensity measurements of intensity sensors 524B and 524C are each 7 units of intensity. In some implementations, an aggregate intensity is the sum of the intensity measurements of the plurality of intensity sensors 524A-524D, which in this example is 32 intensity units. In some embodiments, each contact is assigned a respective intensity that is a portion of the aggregate intensity. FIG. 5D illustrates assigning the aggregate intensity to contacts 552A-552E based on their distance from the center of force 554. In this example, each of contacts 552A, 552B, and 552E are assigned an intensity of contact of 8 intensity units of the aggregate intensity, and each of contacts 552C and 552D are assigned an intensity of contact of 4 intensity units of the aggregate intensity. More generally, in some implementations, each contact j is assigned a respective intensity Ij that is a portion of the aggregate intensity, A, in accordance with a predefined mathematical function, $Ij=A \cdot (Dj/\Sigma Di)$, where Dj is the distance of the respective contact j to the center of force, and $\Sigma Di$ is the sum of the distances of all the respective contacts (e.g., i=1 to last) to the center of force. The operations described with reference to FIGS. 5C-5D can be performed using an electronic device similar or identical to device 100, 300, or 500. In some embodiments, a characteristic intensity of a contact is based on one or more intensities of the contact. In some embodiments, the intensity sensors are used to determine a single characteristic intensity (e.g., a single characteristic intensity of a single contact). It should be noted that the intensity diagrams are not part of a displayed user interface, but are included in FIGS. 5C-5D to aid the reader.

In some embodiments, a portion of a gesture is identified for purposes of determining a characteristic intensity. For example, a touch-sensitive surface optionally receives a continuous swipe contact transitioning from a start location and reaching an end location, at which point the intensity of the contact increases. In this example, the characteristic intensity of the contact at the end location is, optionally, based on only a portion of the continuous swipe contact, and not the entire swipe contact (e.g., only the portion of the swipe contact at the end location). In some embodiments, a smoothing algorithm is, optionally, applied to the intensities of the swipe contact prior to determining the characteristic intensity of the contact. For example, the smoothing algorithm optionally includes one or more of: an unweighted sliding-average smoothing algorithm, a triangular smoothing algorithm, a median filter smoothing algorithm, and/or an exponential smoothing algorithm. In some circumstances, these smoothing algorithms eliminate narrow spikes or dips in the intensities of the swipe contact for purposes of determining a characteristic intensity.

The intensity of a contact on the touch-sensitive surface is, optionally, characterized relative to one or more intensity thresholds, such as a contact-detection intensity threshold, a light press intensity threshold, a deep press intensity threshold, and/or one or more other intensity thresholds. In some embodiments, the light press intensity threshold corresponds to an intensity at which the device will perform operations typically associated with clicking a button of a physical mouse or a trackpad. In some embodiments, the deep press intensity threshold corresponds to an intensity at which the device will perform operations that are different from operations typically associated with clicking a button of a physical mouse or a trackpad. In some embodiments, when a contact is detected with a characteristic intensity below the light press intensity threshold (e.g., and above a nominal contact-detection intensity threshold below which the contact is no longer detected), the device will move a focus selector in accordance with movement of the contact on the touch-sensitive surface without performing an operation associated with the light press intensity threshold or the deep press intensity threshold. Generally, unless otherwise stated, these intensity thresholds are consistent between different sets of user interface figures.

An increase of characteristic intensity of the contact from an intensity below the light press intensity threshold to an intensity between the light press intensity threshold and the deep press intensity threshold is sometimes referred to as a "light press" input. An increase of characteristic intensity of the contact from an intensity below the deep press intensity threshold to an intensity above the deep press intensity threshold is sometimes referred to as a "deep press" input. An increase of characteristic intensity of the contact from an intensity below the contact-detection intensity threshold to an intensity between the contact-detection intensity threshold and the light press intensity threshold is sometimes referred to as detecting the contact on the touch-surface. A decrease of characteristic intensity of the contact from an intensity above the contact-detection intensity threshold to an intensity below the contact-detection intensity threshold is sometimes referred to as detecting liftoff of the contact from the touch-surface. In some embodiments, the contact-detection intensity threshold is zero. In some embodiments, the contact-detection intensity threshold is greater than zero.

In some embodiments described herein, one or more operations are performed in response to detecting a gesture that includes a respective press input or in response to detecting the respective press input performed with a respective contact (or a plurality of contacts), where the respective press input is detected based at least in part on detecting an increase in intensity of the contact (or plurality of contacts) above a press-input intensity threshold. In some embodiments, the respective operation is performed in response to detecting the increase in intensity of the respective contact above the press-input intensity threshold (e.g., a "down stroke" of the respective press input). In some embodiments, the press input includes an increase in intensity of the respective contact above the press-input intensity threshold and a subsequent decrease in intensity of the contact below the press-input intensity threshold, and the respective operation is performed in response to detecting the subsequent decrease in intensity of the respective contact below the press-input threshold (e.g., an "up stroke" of the respective press input).

Figure 5E:
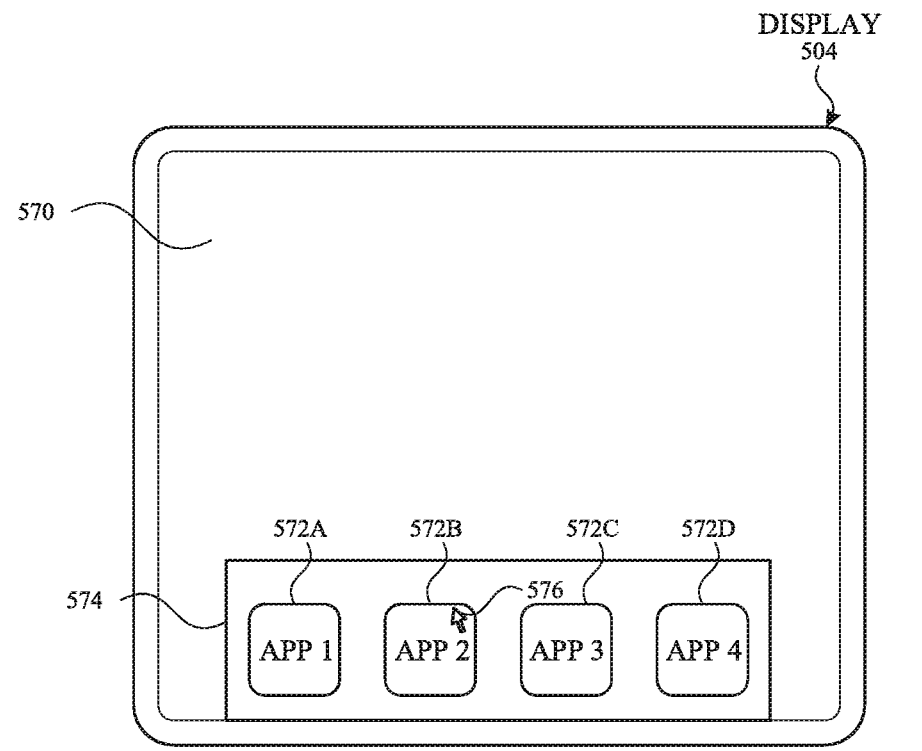
FIGS. 5E-5H illustrate exemplary components and user interfaces of a personal electronic device in accordance with some embodiments.
Figure 5E:
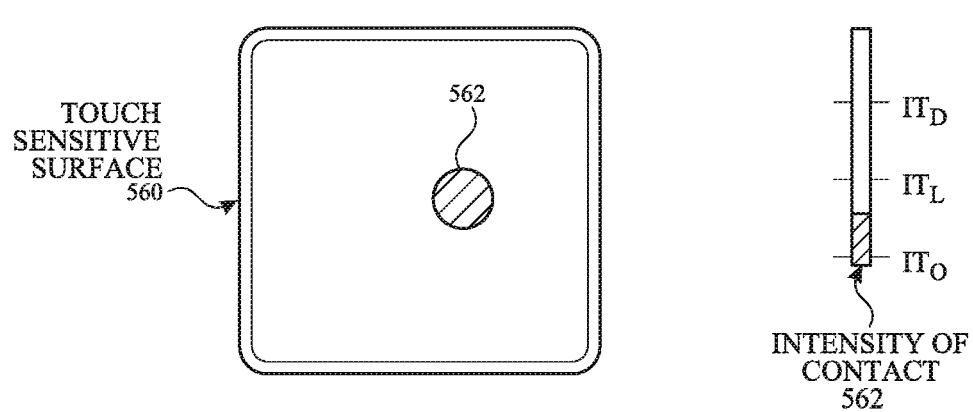
Figure 5F:
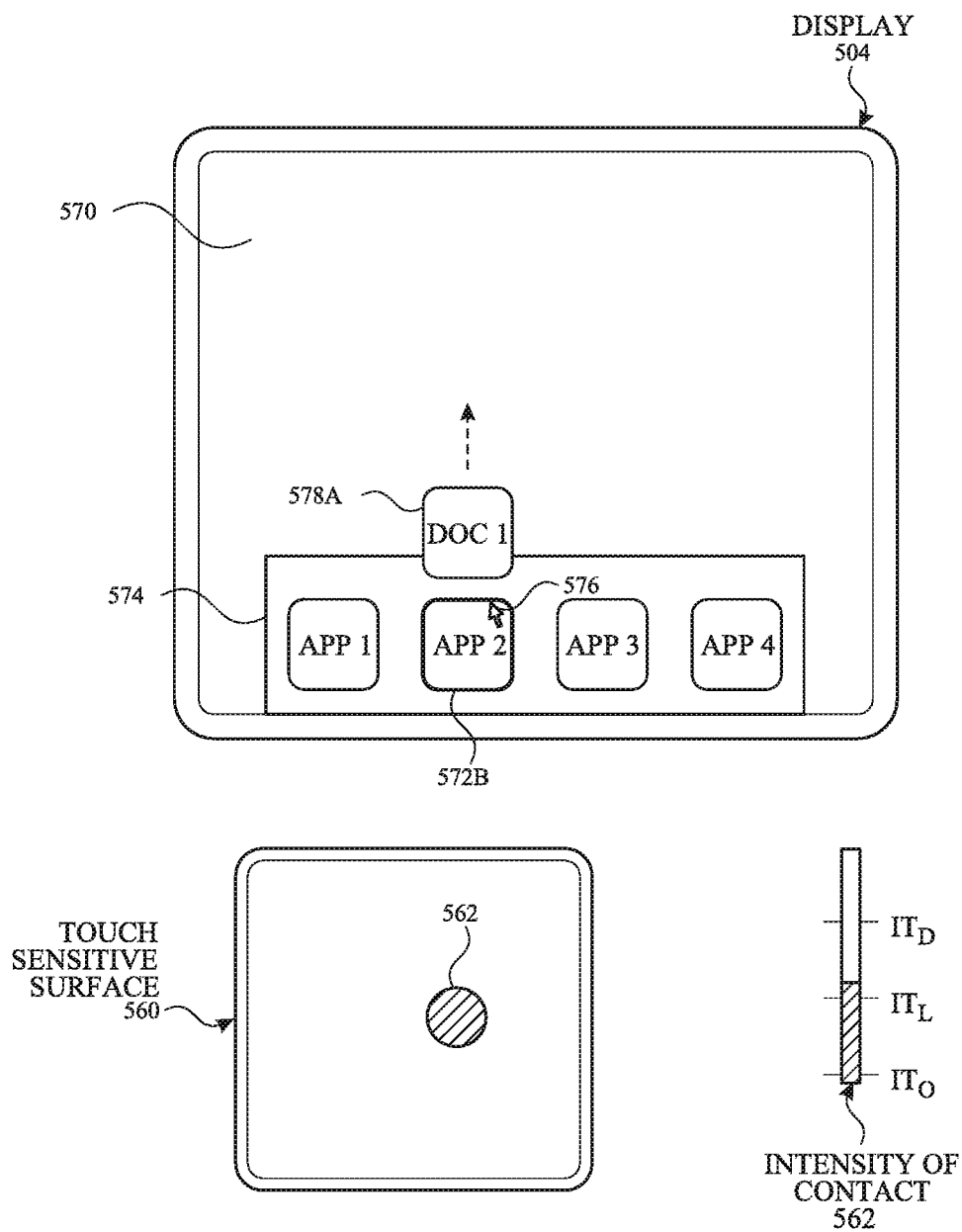
Figure 5G:
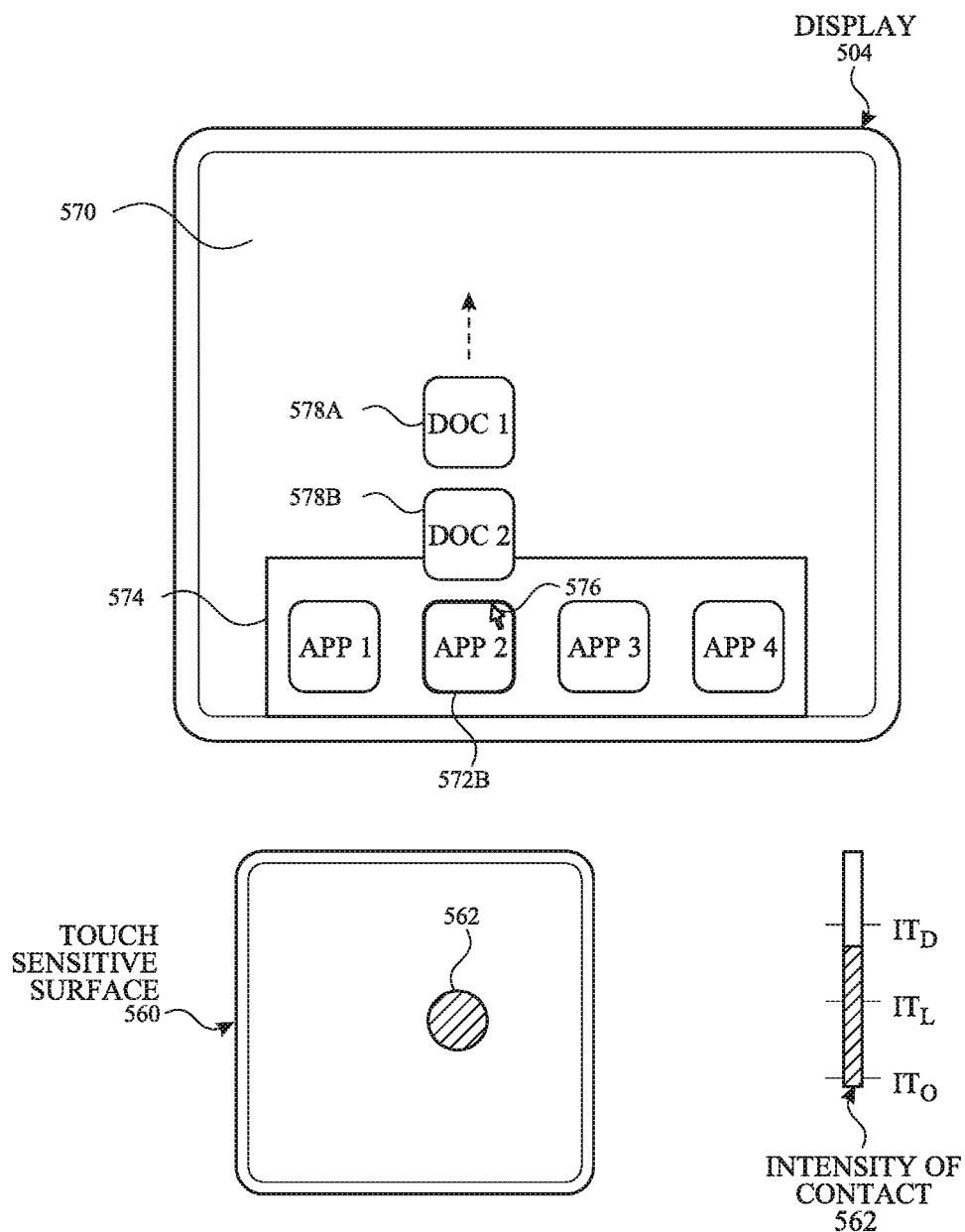
Figure 5H:
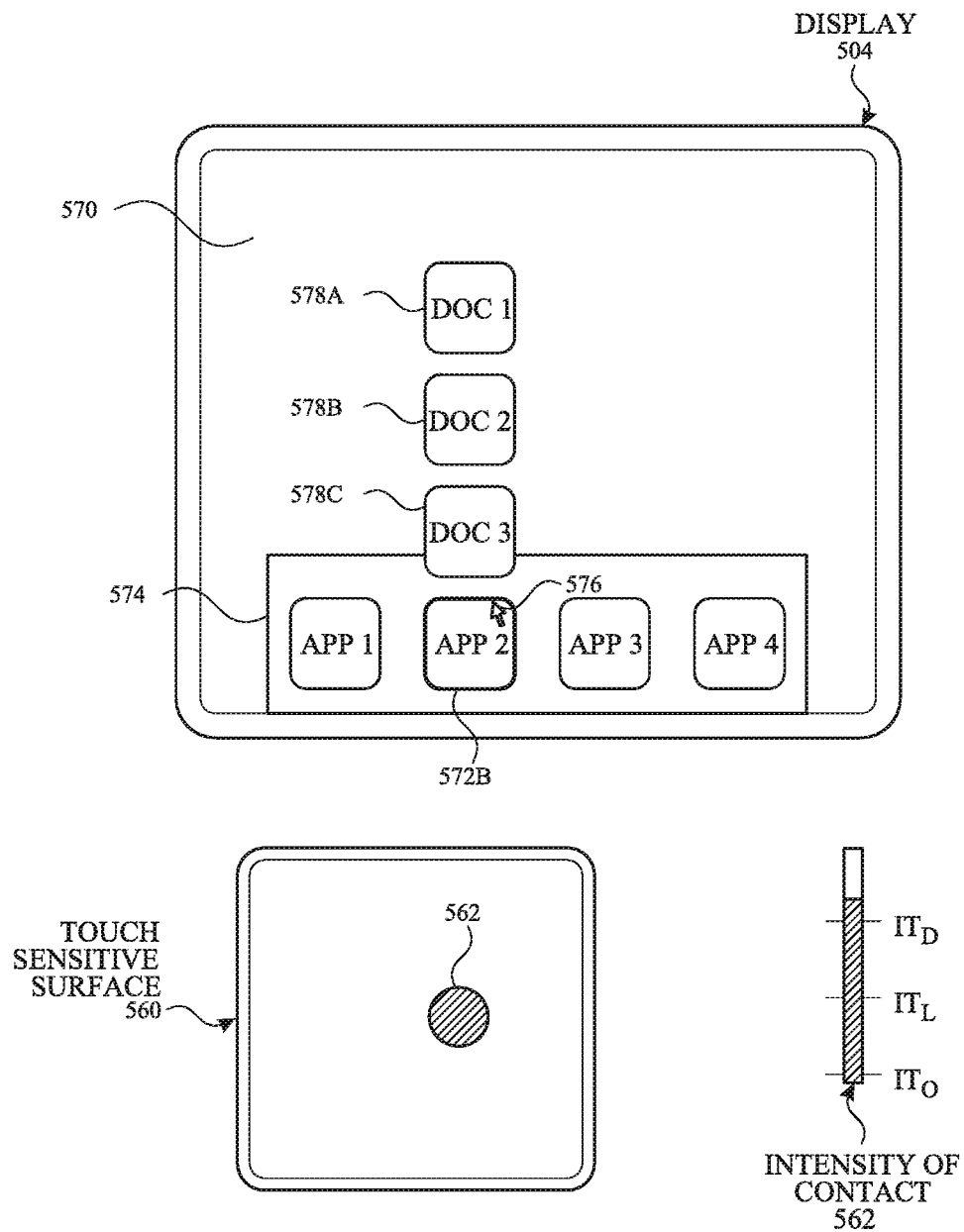

FIGS. 5E-5H illustrate detection of a gesture that includes a press input that corresponds to an increase in intensity of a contact 562 from an intensity below a light press intensity threshold (e.g., "$IT_L$") in FIG. 5E, to an intensity above a deep press intensity threshold (e.g., "$IT_D$") in FIG. 5H. The gesture performed with contact 562 is detected on touch-sensitive surface 560 while cursor 576 is displayed over application icon 572B corresponding to App 2, on a displayed user interface 570 that includes application icons 572A-572D displayed in predefined region 574. In some embodiments, the gesture is detected on touch-sensitive display 504. The intensity sensors detect the intensity of contacts on touch-sensitive surface 560. The device determines that the intensity of contact 562 peaked above the deep press intensity threshold (e.g., "$IT_D$"). Contact 562 is maintained on touch-sensitive surface 560. In response to the detection of the gesture, and in accordance with contact 562 having an intensity that goes above the deep press intensity threshold (e.g., "$IT_D$") during the gesture, reduced-scale representations 578A-578C (e.g., thumbnails) of recently opened documents for App 2 are displayed, as shown in FIGS. 5F-5H. In some embodiments, the intensity, which is compared to the one or more intensity thresholds, is the characteristic intensity of a contact. It should be noted that the intensity diagram for contact 562 is not part of a displayed user interface, but is included in FIGS. 5E-5H to aid the reader.

In some embodiments, the display of representations 578A-578C includes an animation. For example, representation 578A is initially displayed in proximity of application icon 572B, as shown in FIG. 5F. As the animation proceeds, representation 578A moves upward and representation 578B is displayed in proximity of application icon 572B, as shown in FIG. 5G. Then, representations 578A moves upward, 578B moves upward toward representation 578A, and representation 578C is displayed in proximity of application icon 572B, as shown in FIG. 5H. Representations 578A-578C form an array above icon 572B. In some embodiments, the animation progresses in accordance with an intensity of contact 562, as shown in FIGS. 5F-5G, where the representations 578A-578C appear and move upwards as the intensity of contact 562 increases toward the deep press intensity threshold (e.g., "$IT_D$"). In some embodiments, the intensity, on which the progress of the animation is based, is the characteristic intensity of the contact. The operations described with reference to FIGS. 5E-5H can be performed using an electronic device similar or identical to device 100, 300, or 500.

In some embodiments, the device employs intensity hysteresis to avoid accidental inputs sometimes termed "jitter," where the device defines or selects a hysteresis intensity threshold with a predefined relationship to the press-input intensity threshold (e.g., the hysteresis intensity threshold is X intensity units lower than the press-input intensity threshold or the hysteresis intensity threshold is 75%, 90%, or some reasonable proportion of the press-input intensity threshold). Thus, in some embodiments, the press input includes an increase in intensity of the respective contact above the press-input intensity threshold and a subsequent decrease in intensity of the contact below the hysteresis intensity threshold that corresponds to the press-input intensity threshold, and the respective operation is performed in response to detecting the subsequent decrease in intensity of the respective contact below the hysteresis intensity threshold (e.g., an "up stroke" of the respective press input). Similarly, in some embodiments, the press input is detected only when the device detects an increase in intensity of the contact from an intensity at or below the hysteresis intensity threshold to an intensity at or above the press-input intensity threshold and, optionally, a subsequent decrease in intensity of the contact to an intensity at or below the hysteresis intensity, and the respective operation is performed in response to detecting the press input (e.g., the increase in intensity of the contact or the decrease in intensity of the contact, depending on the circumstances).

For ease of explanation, the descriptions of operations performed in response to a press input associated with a press-input intensity threshold or in response to a gesture including the press input are, optionally, triggered in response to detecting either: an increase in intensity of a contact above the press-input intensity threshold, an increase in intensity of a contact from an intensity below the hysteresis intensity threshold to an intensity above the press-input intensity threshold, a decrease in intensity of the contact below the press-input intensity threshold, and/or a decrease in intensity of the contact below the hysteresis intensity threshold corresponding to the press-input intensity threshold. Additionally, in examples where an operation is described as being performed in response to detecting a decrease in intensity of a contact below the press-input intensity threshold, the operation is, optionally, performed in response to detecting a decrease in intensity of the contact below a hysteresis intensity threshold corresponding to, and lower than, the press-input intensity threshold.

As used herein, an "installed application" refers to a software application that has been downloaded onto an electronic device (e.g., devices 100, 300, and/or 500) and is ready to be launched (e.g., become opened) on the device. In some embodiments, a downloaded application becomes an installed application by way of an installation program that extracts program portions from a downloaded package and integrates the extracted portions with the operating system of the computer system.

As used herein, the terms "open application" or "executing application" refer to a software application with retained state information (e.g., as part of device/global internal state 157 and/or application internal state 192). An open or executing application is, optionally, any one of the following types of applications:
  an active application, which is currently displayed on a display screen of the device that the application is being used on;
  a background application (or background processes), which is not currently displayed, but one or more processes for the application are being processed by one or more processors; and
  a suspended or hibernated application, which is not running, but has state information that is stored in memory (volatile and non-volatile, respectively) and that can be used to resume execution of the application.

As used herein, the term "closed application" refers to software applications without retained state information (e.g., state information for closed applications is not stored in a memory of the device). Accordingly, closing an application includes stopping and/or removing application processes for the application and removing state information for the application from the memory of the device. Generally, opening a second application while in a first application does not close the first application. When the second application is displayed and the first application ceases to be displayed, the first application becomes a background application.

Attention is now directed towards embodiments of user interfaces ("UI") and associated processes that are implemented on an electronic device, such as portable multifunction device 100, device 300, or device 500.

FIGS. 6A-6W illustrate exemplary user interfaces for monitoring fitness activity, in accordance with some embodiments. In particular, FIGS. 6A-6I, 6M, 6P, and 6U illustrate user interfaces for monitoring fitness activity while a device is in a youth-specific device mode (e.g., a mode optimized for users below the age of 13), whereas, FIGS. 6J-6L, 6N, and 6Q illustrate corresponding user interfaces for monitoring fitness activity while the device is in a second device mode (e.g., a mode optimized for adults and users above the age of 13). FIGS. 6R-6W illustrate additional user interface related to transitioning between device modes. The user interfaces in these figures are used to illustrate the processes described below, including the processes in FIGS. 7A-7C.

FIG. 6A illustrates device 600 with display 602 and rotatable and depressible input mechanism 604 (e.g., rotatable and depressible in relation to a housing or frame of the device), and button 606. In some embodiments, device 600 is a wearable electronic device, such as smartwatch. In some embodiments, device 600 includes one or more features of devices 100, 300, or 500.

As illustrated in FIG. 6A, while operating in a youth device mode, device 600 displays clock user interface 608A on display 602. Clock user interface 608A includes digital indication of time 610 (e.g., a representation of digital clock displaying current hour, minute, and second values), and multiple affordances (e.g., watch face complications), each affordance associated with an application on device 600. Date affordance 612 indicates a current date and launches a calendar application upon selection. Workout affordance 614 launches a workout application upon selection (e.g., an application to track workouts performed by a user of device 600).

As depicted in FIG. 6A, clock user interface 608A also includes multiple affordances indicating user activity data obtained from an activity tracking application (e.g., activity metrics quantifying recorded physical activity of a user of device 600 during a current day). Clock user interface 608A also includes numeric activity affordance 616, graphical activity affordance 618, and textual activity affordance 620. The data indicated by each activity affordance (e.g., as described below), is concurrently updated in response to receiving data from the associated activity application.

Numeric activity affordance 616 includes move value 616A representing a movement metric (e.g., minutes of general physical movement of a user of device 600), exercise value 616B representing an exercise metric (e.g., minutes of strenuous physical activity of a user of device 600, such as time playing a sport), and stand value 616C representing a standing hours metric (e.g. number of hours a user of device 600 has stood for a minimum amount of time such as 2-minutes). In some embodiments, the movement metric represented by move value 616A, is a time-based activity metric (e.g., minutes of activity that meet an activity threshold). In some embodiments, the movement metric is derived from another metric (e.g., an energy or calorie-based metric) which is based on received user activity data.

Graphical activity affordance 618 includes three concentric rings (e.g., move ring 618A; exercise ring 618B, and stand ring 618C), corresponding to move value 616A, exercise value 616B, and stand value 616C, respectively. The angular length of each ring (e.g., the angular distance covered by the arc associated with each ring relative to 360 degrees) indicates current progress towards a respective activity goal associated with a ring (e.g., ring 618C shows 60% of a completed ring indicating completion of 6 standing hours out of a daily goal of 10 standing hours). Textual activity affordance 620 includes textual representations of activity data values (e.g., textual move value 620A, textual exercise value 620B, and textual stand value 620C) corresponding to data described above with respect to numeric activity affordance 616 and graphical activity affordance 618 (e.g., textual move value 620A indicates move minutes and corresponds to move value 616A and ring 618A).

At FIG. 6A, device 600 receives user input 622 corresponding to selection of graphical activity affordance 618. In response to user input 622, device 600 launches the activity tracking application associated the affordance (e.g., displays of a user interface of the Activity application, such as user interface 624A as depicted in FIG. 6B).

Figure 6B:
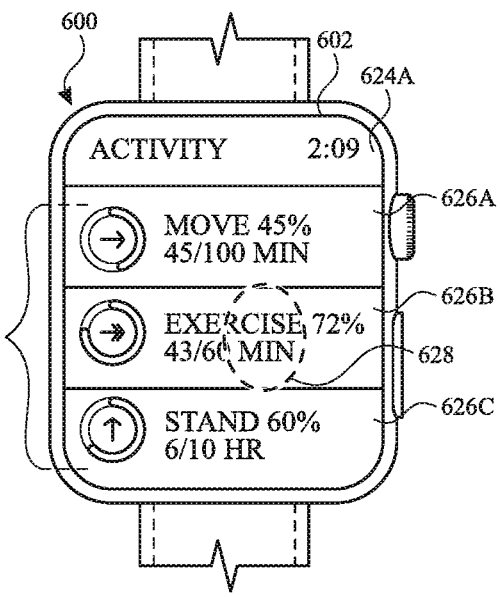

As illustrated in FIG. 6B, user interface 624A includes activity platters 626 (e.g., move platter 626A, exercise platter 626B, and stand platter 626C), which summarize user activity the data displayed by numeric activity affordance 616, graphical activity affordance 618, and textual activity affordance 620 (e.g., move platter 626A includes representations of the data shown by move value 616A, move ring 618A, and textual move value 620A).

Figure 6C:
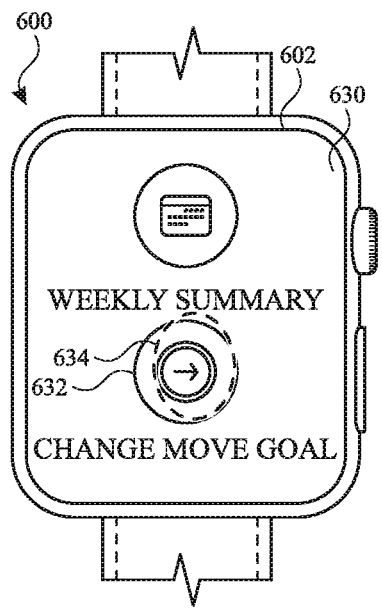

At FIG. 6B, device 600 receives user input 628. In response to user input 628 (e.g., a tap input with characteristic intensity beyond an threshold intensity, an input lasting longer than a threshold period of time), device 600 displays user interface 630 as depicted in FIG. 6C. User interface 630 includes change goal affordance 632 for changing a user activity goal associated with a user activity metric (e.g., movement goal, move minutes goal). FIG. 6C depicts device 600 receiving user input 634 corresponding to selection of change goal affordance 632. In response to user input 634, device 600 displays of user interface 636 as depicted in FIG. 6D.

Figure 6D:
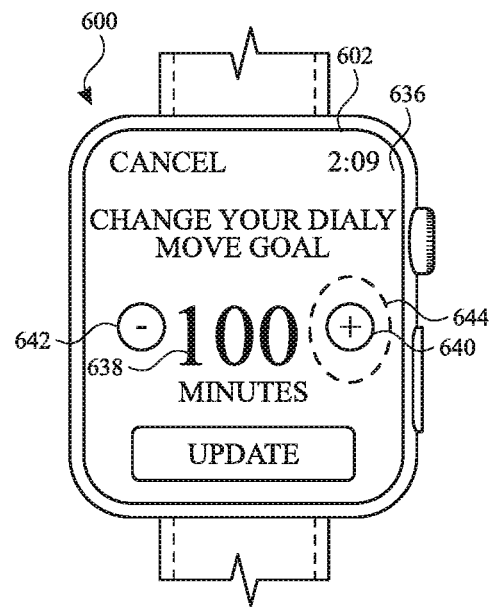
Figure 6E:

User interface 636, as illustrated in FIG. 6D, permits a user to adjust activity goal value 638 by selecting add affordance 640 or subtract affordance 642. FIG. 6D depicts device 600 receiving user input 644 corresponding selection of add affordance 640, which causes device 600 to display user interface 646 as depicted in FIG. 6E. User interface 646 shows that activity goal value 638 has been updated to a new value (e.g., now reflecting 110 move minutes rather than the 100 move minutes as previously shown in FIG. 6D), in response to user input 644.

Figure 6F:
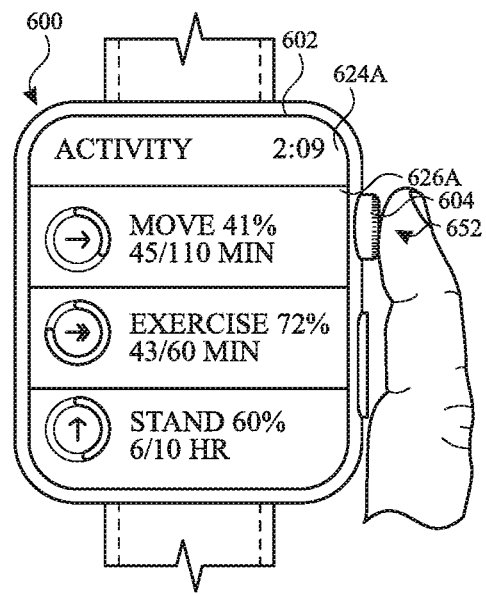

At FIG. 6E, device 600 receives user input 648 at update affordance 650. In response to user input 648, device 600 saves updated activity goal 638 and re-displays user interface 624A (e.g., as depicted in FIG. 6F). As shown in FIG. 6F, move platter 626A displays user activity data according to the updated move goal of 110. For example, move platter 626A indicates that only 41% (e.g., compared the previous 45% as shown in FIG. 6B) of the current move goal has been completed (e.g., 45/110).

Figure 6G:
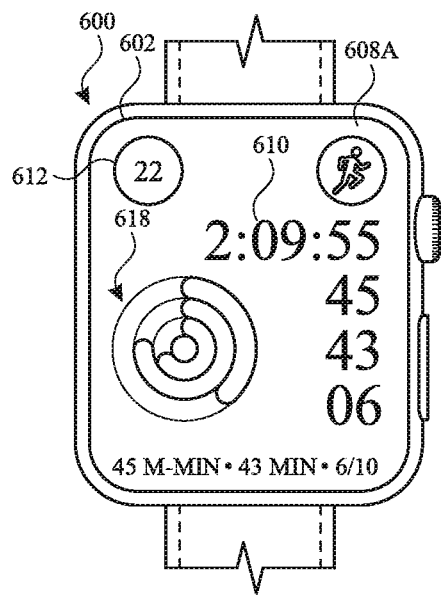

At FIG. 6F, device 600 receives user input 652, a depression of rotatable and depressible input mechanism 604. In response to user input 652, device 600 displays clock user interface 608A (e.g., a watch face) with an updated graphical activity affordance 618, as depicted in FIG. 6G. FIG. 6G depicts clock user interface 608A at a current time of 2:09:55 (e.g., 16 seconds have elapsed since device 600 displayed clock user interface 608A as depicted in FIG. 6A) on the $22^{nd}$ day of a current month (e.g., May 2019), as indicated by date affordance 612 (e.g., "22").

Figure 6H:
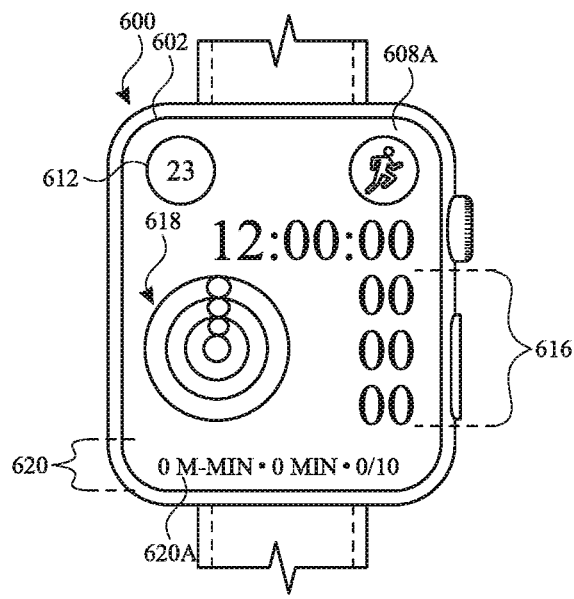

FIG. 6H depicts clock user interface 608A the day after the $22^{nd}$ day of the current month (e.g., on the $23^{rd}$ day of May 2019). Numeric activity affordance 616, graphical activity affordance 618, and textual activity affordance 620 have reset to reflect that no activity data has been recorded by the activity application for the current day (e.g., the $23^{rd}$ day of May 2019). For example, textual move value 620A indicates that "0 M-MINS" (e.g., move minutes) have been recorded.

Figure 6I:
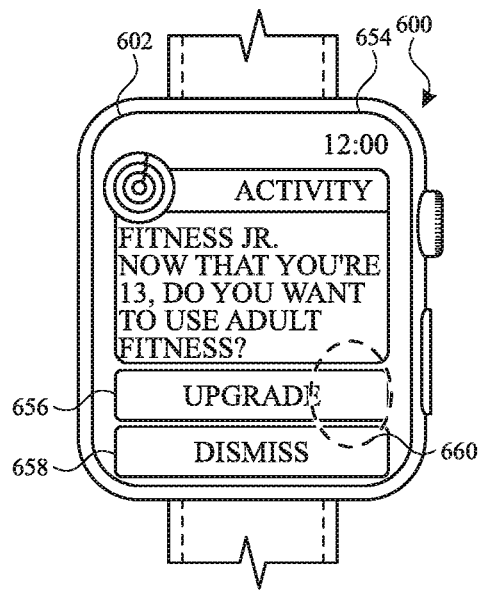

In response to determining that the age of a user of device 600 has changed from 12 years old to 13 years old (e.g., the users 13th birthday is the 23rd day of the current month (e.g., May 2019)), device 600 displays user interface 654 as depicted in FIG. 6I. In some embodiments, device 600 determines a change in age by comparing birth data associated with a user of device 600 to a current date. User interface 654 includes a prompt describing the availability of a new device mode (e.g., an adult device mode associated with displaying a move calories metric), upgrade affordance 656 for opting into the new adult device mode, and dismiss affordance 658 for maintaining operation of device 600 in youth device mode (e.g. a device mode associated with displaying a move minutes metric). In some embodiments, device 600 displays user interface 654 a predetermined period (e.g., a day) prior to a user age exceeding a threshold age (e.g., 13 years).

Figure 6J:
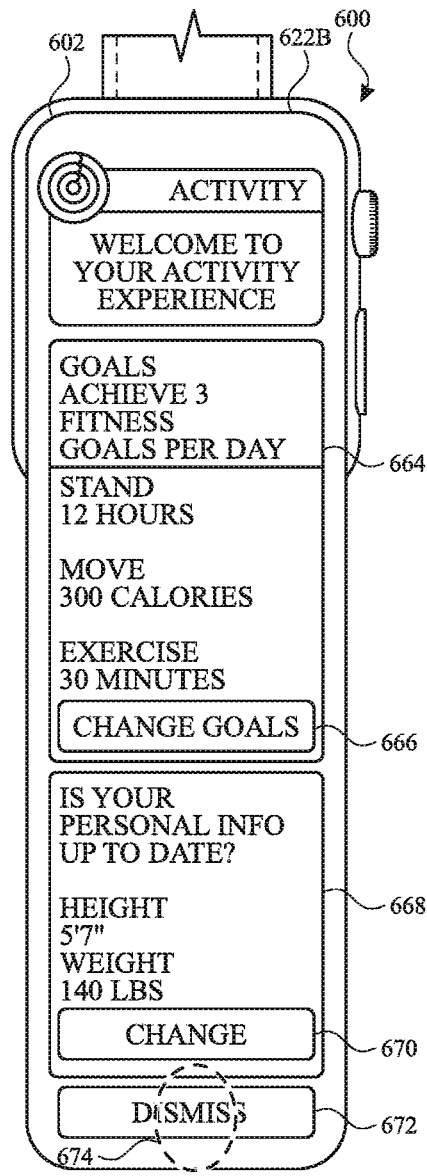
Figure 6K:
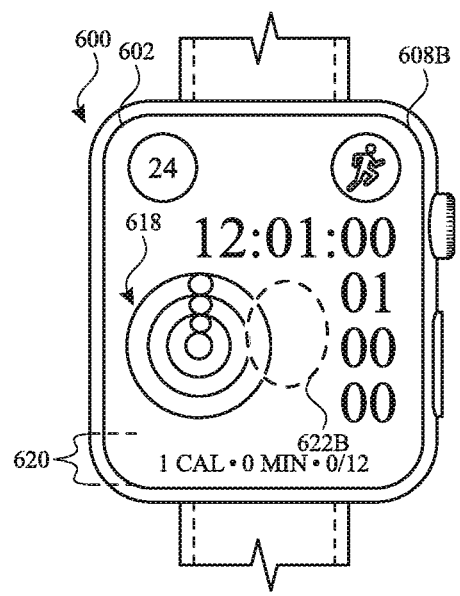
Figure 6L:
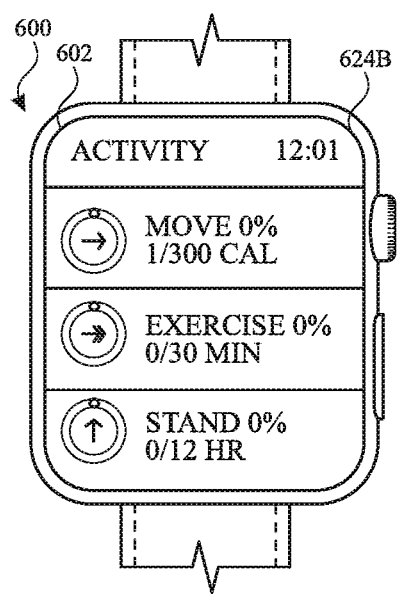

At FIG. 6I, device 600 receives user input 660 corresponding to selection of upgrade affordance 656. In response to user input 660, device 600 transitions from operating in a youth mode (e.g., a mode displaying a move minutes metric as illustrated in FIGS. 6A and 6B) to operating in an adult mode (e.g., a mode displaying a different metric, move calories as illustrated in FIGS. 6K and 6L). In response to user input 660, device 600 displays adult mode welcome user interface 662B as depicted in FIG. 6J, further emphasizing that device 600 is now currently operating an adult device mode. In some embodiments, a user selects the upgrade affordance in the middle of a day (e.g., noon on Monday May 23) and the transition to adult mode does not occur until the next day (e.g., 12:00a on Tuesday May 24). In some embodiments, after selecting the upgrade affordance, the device may no longer operate in youth mode (e.g., the transition to operating in adult mode is irreversible after user's age is greater than a predetermined age).

As depicted in FIG. 6J, adult mode welcome interface 662B includes activity goal summary 664, personal information summary 668, and dismiss affordance 672. Activity goal summary 664 includes change goals affordance 666 for editing activity goals. In some embodiments, initial activity goals are set to default values associated with device 600 operating in adult mode (e.g., 300 move calories, 30 exercise minutes, and 12 stand hours). In some embodiments, initial activity goals are based in part user data (e.g., historic activity, age, gender, weight, and the like). In some embodiments, selection of change goals affordance 666 causes device 600 to display a series of interfaces similar to those depicted in FIGS. 6D and 6E, which permit individual activity metric goals to be updated. Personal information summary 668 includes a summary of personal data (e.g., height and weight) used by device 600 to derive activity metric data (e.g., data used to show progress towards move calories, exercise minutes, and stand hours goals shown in activity goal summary 664) and change information affordance 670 for editing personal data. In some embodiments, selection of change information affordance 670 causes device 600 to display a series of interfaces which permit updating user height and weight information. In some embodiments, goals and personal info are changed via a settings menu rather than from adult mode welcome interface 662B.

In some embodiments, in response to determining, while the device is in the youth mode, that the age of a user of device 600 has changed from 17 years old to 18 years old (e.g., the users 18th birthday is the 23rd day of the current month (e.g., May 2019)), device 600 foregoes displaying user interface 654 as depicted in FIG. 6I and instead directly transitions (e.g. without receiving user input corresponding to consent or permission) to operating in an adult mode (e.g., a device mode associated with display a move calories metric), and subsequently displays welcome user interface 662B (e.g. the transition of device 600 from operating in youth mode to operating in an adult is not optional). In some embodiments, the transition to adult mode does not occur until the day after a user age exceeds a predetermined threshold (e.g., user turns 18 on Monday, May 23 and device 600 transitions to operating in adult mode on Tuesday, May 24).

At FIG. 6J device 600 receives user input 674 at dismiss affordance 672. In response to user input 674, device 600 displays user interface 608B (e.g., a clock face interface in adult mode) as depicted in FIG. 6K. FIG. 6K depicts clock user interface 608B (e.g., corresponding to an adult version of clock user interface 608A) which includes updated time and date affordances (e.g., indicating a new current time and date), and updated activity complications (e.g., activity complications 616, 618, and 620 display data representing current progress towards respective activity goals). For example, as depictive in FIG. 6K, textual activity complication 620 includes a depiction of a CAL value (e.g., move calories metric) rather than a depiction of M-MINS value (e.g., move minutes metric). In some embodiments, the move calories metric is based at least in part on user-defined data (e.g., weight, height, sex, or age, etc.). In some embodiments, the move calories metric is based at least in part on data measured by the device (e.g., heart rate, historical motion data, etc.).

At FIG. 6K device 600 receives user input 622B, an input corresponding to selection of graphical activity affordance 618. In response to user input 622B, device 600 launches the activity tracking application resulting in device 600 displaying user interface 624B (e.g., an adult mode user interface corresponding to the youth mode user interface 624A depicted in FIG. 6B) as depicted in FIG. 6L. User interface 624B includes activity platters 626, which summarize user activity the data displayed by numeric activity affordance 616, graphical activity affordance 618, and textual activity affordance 620 while device is operating in adult mode (e.g., a device mode associated displaying a move calories metric).

Figure 6M:
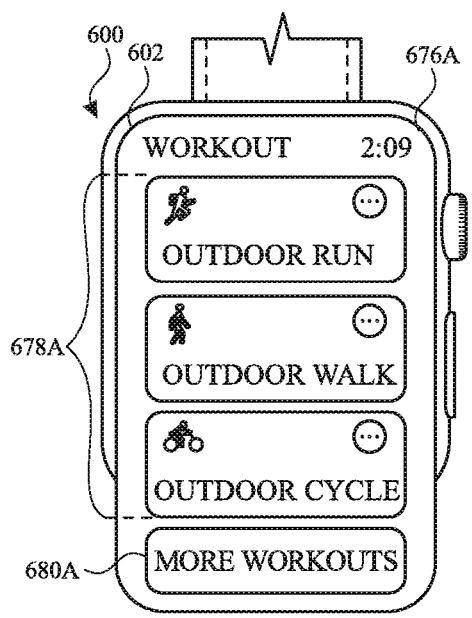
Figure 6N:
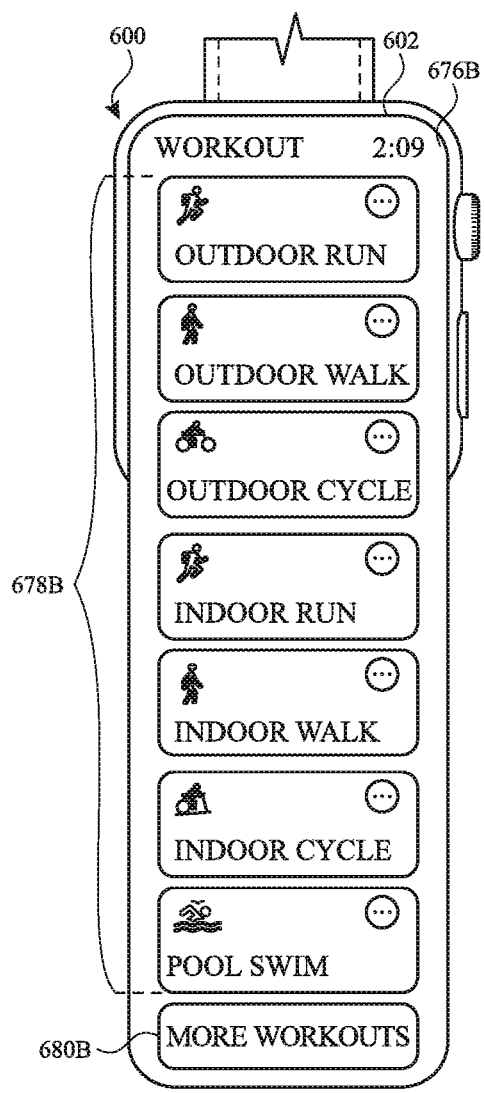

FIGS. 6M and 6N depict device 600 displaying corresponding workout application interfaces while operating in youth mode (e.g., a device mode associated displaying a move minutes metric) and adult mode (e.g., a device mode associated displaying a move calories metric), respectively. Device 600 displays user interface 676A in response to, for example, detecting selection of workout affordance 614 of FIG. 6A. User interface 676A includes workout group 678A (e.g., including outdoor run, outdoor walk, and outdoor cycle activity affordances that when selected cause device 600 to initiate an activity monitoring process corresponding the selected workout activity). In some embodiments, activity monitoring processes include receiving motion data based on user movement (e.g., movement of a device worn by the use), determining workout metrics (e.g. active calorie burn, total calorie burn, heart rate, distance traveled, etc.) based on received motion data, and displaying representations of the workout metrics on one or more display devices. In some embodiments, the activity monitoring processes determine workout metrics according to algorithms optimized for younger users (e.g., tuned specifically to provide accurate metrics for children as opposed to adults).

Device 600 displays user interface 676B in response to, for example, detecting selection of workout affordance 614 of FIG. 6K. User interface 676B includes workout group 678B, which includes affordances corresponding to each workout displayed in workout group 678A, in addition to other workout affordances (e.g., indoor run, indoor walk, indoor cycle, pool swim, etc.). In some embodiments, workout group 678B includes a subset of a larger set of available workouts which is accessed by selecting a "more workouts" affordance or the like.

In some embodiments, while device 600 is operating in youth mode (e.g., a device mode associated with displaying a move minutes metric), additional workouts may be added to workout group 678A (e.g., additional workouts from workout group 676B or other workouts not included in workout group 678B) by selecting a "more workouts" affordance 680A or the like. In some embodiments, in response to selecting a "more workouts" affordance 680A, device 600 displays a prompt indicating that additional workouts may not be optimized for younger users (e.g., "adding additional workouts may result in accurate activity tracking"). In some embodiments, workouts added in youth mode appear in adult mode after the transition (e.g., if archery is added to workout group 678A in youth mode, upon transition to adult mode, workout group 678B additionally includes archery).

Figure 6O:
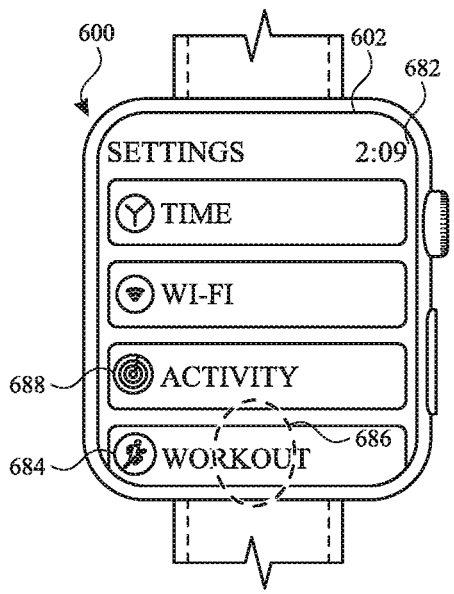
Figure 6P:
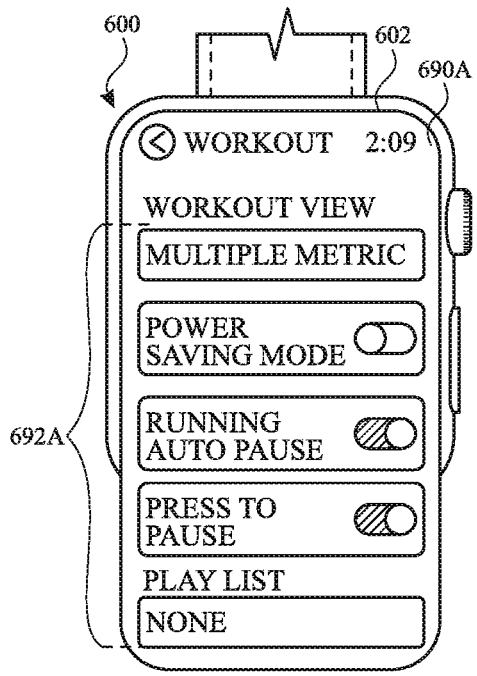

FIG. 6O depicts a setting menu of device 600 (e.g. watch settings) which includes workout settings affordance 684 for accessing settings associated with a workout application on device 600 (e.g., the workout application associated with workout complication 614) and activity settings affordance 688 for accessing settings associated with the activity application (e.g., the activity application associated with activity complication 618). At FIG. 6O, device 600 receives user input 686 corresponding to selection of workout settings affordance 684. In response to receiving user input 686, while device 600 is operating in youth mode (e.g., a device mode associated displaying a move calories metric), user interface 690A is displayed (e.g. as depicted in FIG. 6P). User interface 690A includes workout settings group 692A (e.g., including affordances for adjusting settings associated with the workout application).

Figure 6Q:
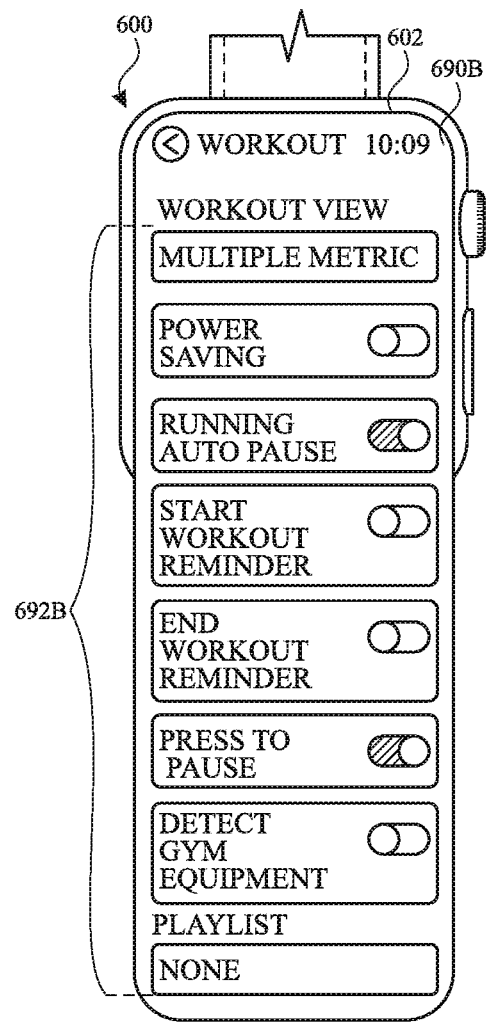

In response to receiving user input 686 while device 600 is operating in adult mode (e.g., a device mode associated displaying a move calories metric), device 600 displays user interface 690B (e.g., as depicted in FIG. 6Q). In contrast to user interface 690A (e.g., the corresponding youth mode interface), user interface 690B includes additional workout settings affordances. For example, workout settings group 692B includes affordances to enable or disable workout features unavailable in youth mode (e.g., start workout reminder, end workout reminder, and detect gym equipment). In some embodiments, the additional features included in workout settings group 692B (e.g., features not included in workout settings group 692A or otherwise available while device 600 is operating in youth mode) are disabled by default upon device 600 transitioning from operating in youth mode to operating in adult mode.

Figure 6R:
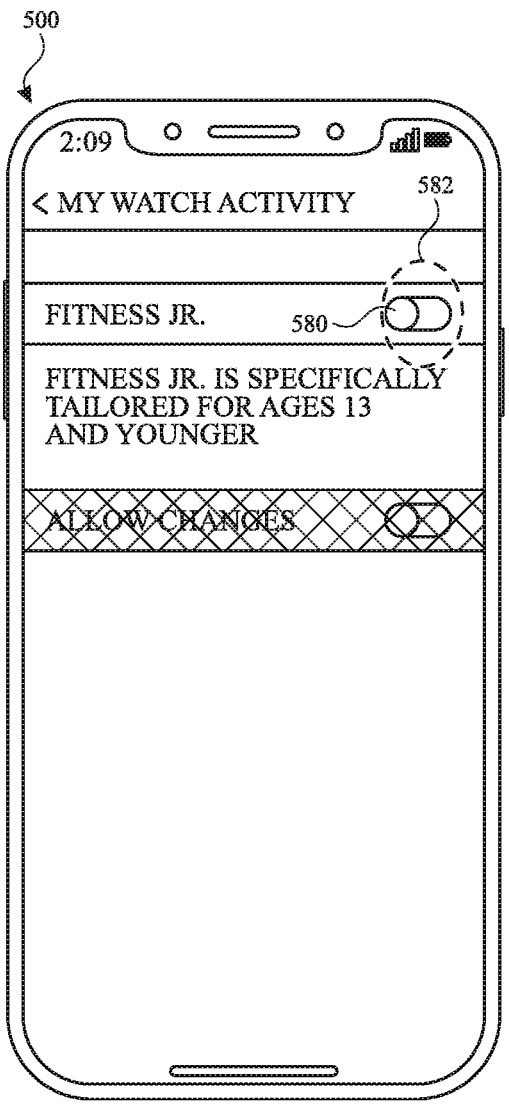
Figure 6S:
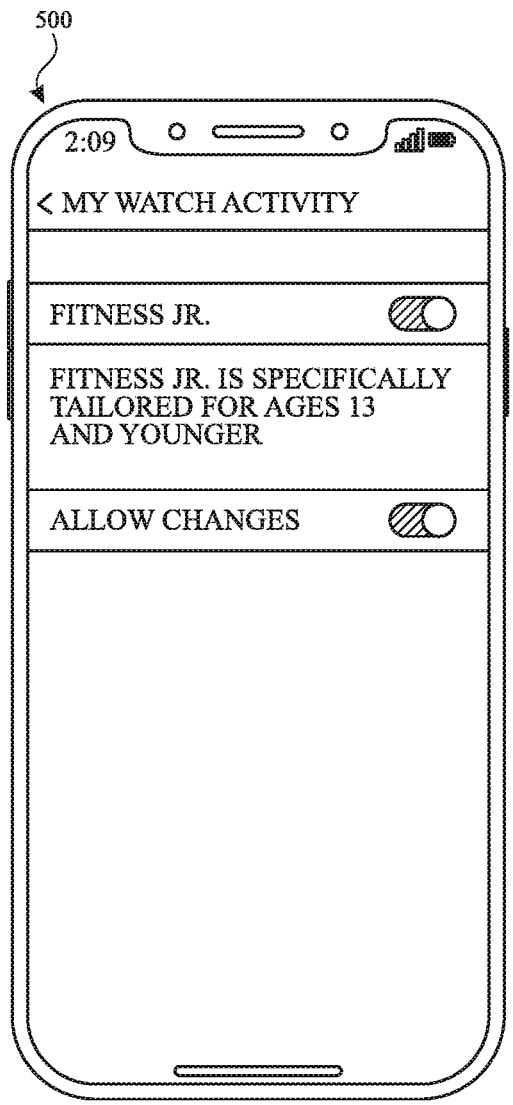

FIGS. 6R and 6S illustrate a second device (e.g., device 500) wirelessly linked to device 600. In some embodiments, device 600 receives configuration data indicating a selection of a device mode from device 500 (e.g., device 500 transmits data representing a request enable youth mode of device 600 in response to receiving input 582 at youth mode affordance 580). In some embodiments, in response to receiving data indicating a selection of a device mode, device 600 displays user interface 694 as depicted in FIG. 6T. In some embodiments, data indicating selection of the youth mode from a second device indicates parental consent (e.g., for device 600 to collect of information from a user of device 600 under the age of 13).

At FIG. 6T, device 600 displays a warning prompt (e.g., interface 694) indicating the selection of a device mode (e.g. adult mode) from device 500. In some embodiments, device 600 will only transition from operating in a first mode (e.g. adult mode) to operating in a second mode (e.g., youth mode), in response to detecting an input corresponding to a selection of confirmation affordance 696.

At FIG. 6T, device 600 receives an input 696 corresponding to a selection of mode change confirmation affordance 695 and in response to receiving input 696, device 600 displays youth mode welcome interface 622A of FIG. 6U. As depicted in FIG. 6U, youth mode welcome interface 662A includes elements corresponding the elements of adult mode welcome interface 662B (e.g., as described above in reference to FIG. 6J). In some embodiments, initial activity goals are set to default values associated with device 600 operating in youth mode (e.g., 100 move minutes, 60 exercise minutes, and 10 stand hours. In some embodiments, initial activity goals are based in part user data (e.g., historic activity, age, gender, weight, and the like). In some embodiments, selection of a change goals affordance causes device 600 to display a series of interfaces similar to those illustrated by FIGS. 6D and 6E, which permit activity metric goals to be updated. In some embodiments, goals and personal info are changed via settings menu rather than from welcome prompt.

Figure 6V:
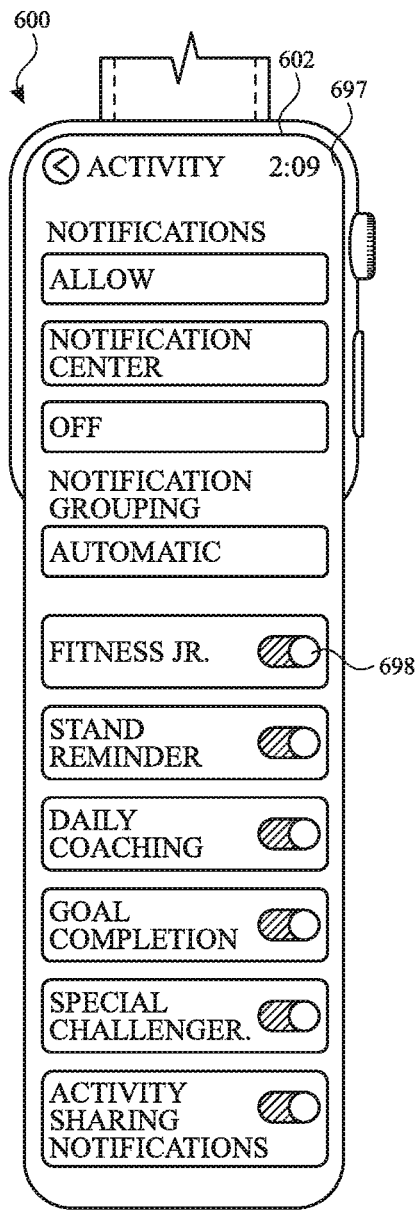
Figure 6W:
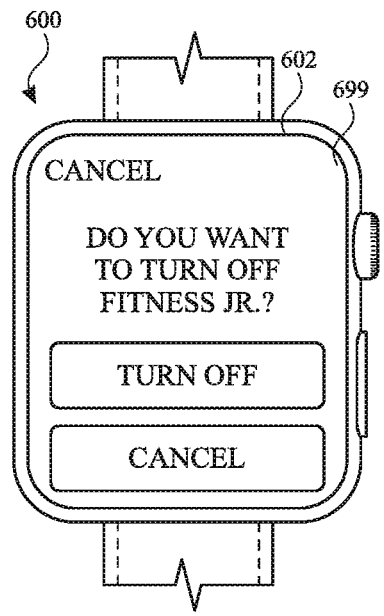
Figure 7A:
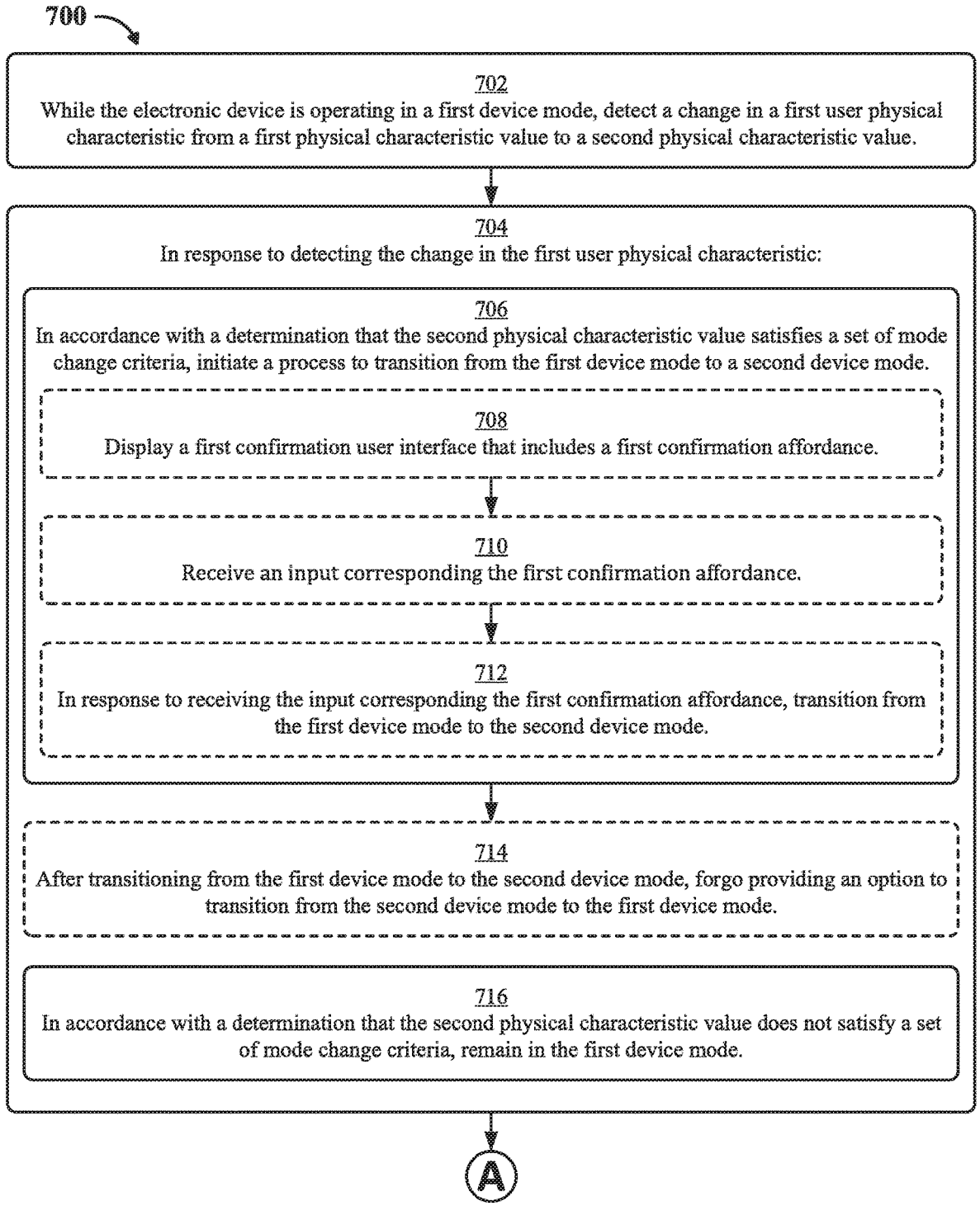
Figure 7B:
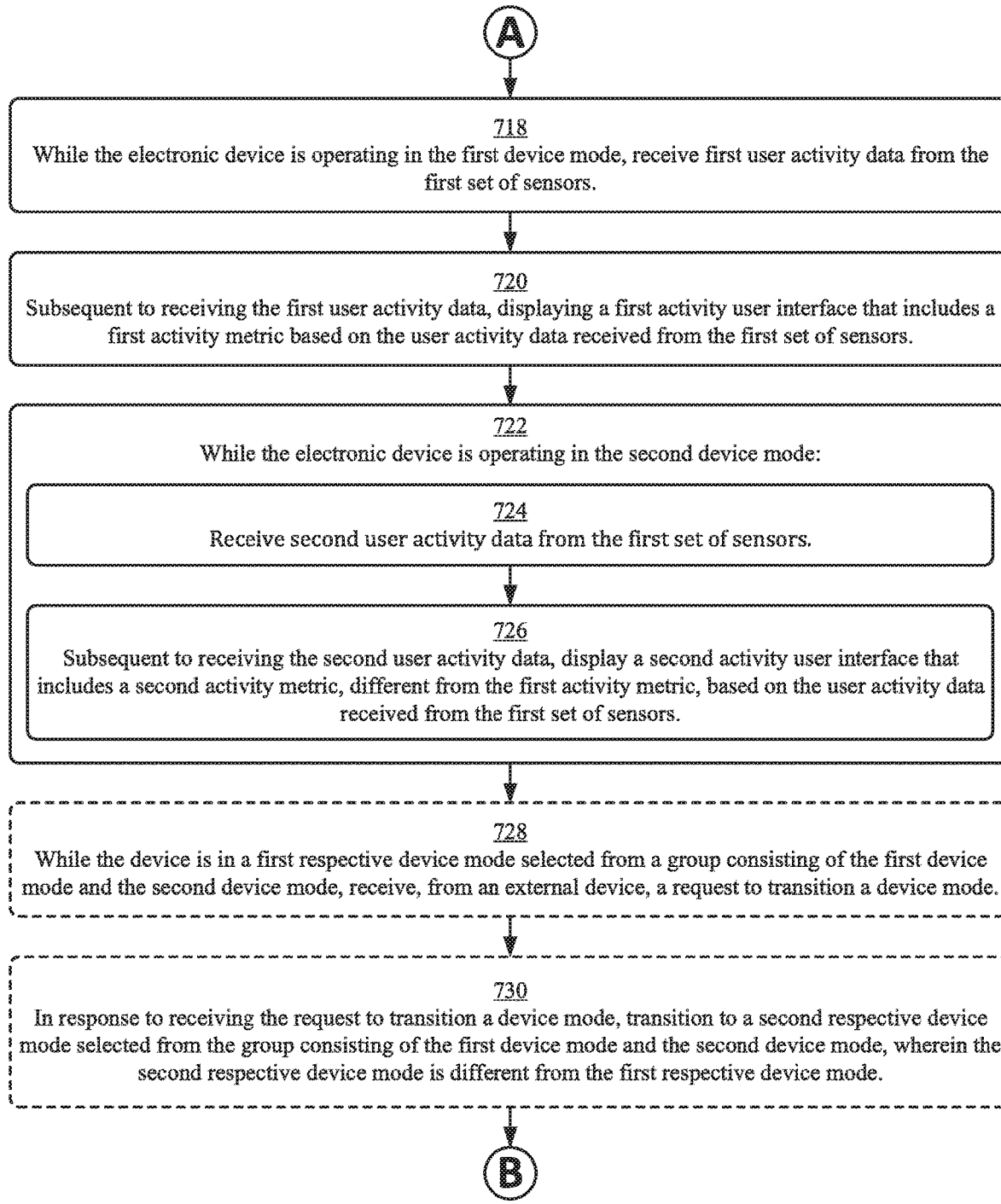

FIG. 6V depicts activity application settings user interface 697 of device 600. In some embodiments, device 600 displays activity application settings user interface 697 in response to receiving an input corresponding to selection of activity settings affordance 688 (e.g., as depicted in FIG. 6O). As depicted in FIG. 6V, activity application settings user interface 697 includes activity affordances for enabling or disabling features associated with the activity application on device 600 (e.g., the active application associated with activity affordance 616). In some embodiments, activity application settings user interface 697 includes mode affordance 698 which when selected, causes device 600 to initiate a transition from operating in a first device mode (e.g., youth mode) to operating in a second device modes (e.g., adult mode). In some embodiments, mode affordance 698 is not displayed or disabled such that user input detected at the affordance does not initiate a transition between device modes. In some embodiments, once device 600 transitions to operating in adult mode (e.g., a mode associated with displaying a move calories metric), mode affordance 698 is not displayed as part of activity application settings user interface 698, thus preventing the user of device 600 from manually changing device modes. In some embodiments, mode affordance 698 is displayed in a disabled state (e.g., greyed out and unresponsive to user input), in response to receiving configuration data from a second device (e.g., device 500) including instructions to disable mode changes on device 600 (e.g., device 600 receives data from device 500 in response to device 500 receiving input at an "allow changes" affordance (e.g., as depicted in FIG. 6S)).

At FIG. 6W, device 600 displays warning prompt interface 699 in response to receiving a request to change between adult mode and youth mode (e.g., selection of a mode affordance 698 for enabling and disabling the youth mode). In some embodiments, device 600 will only transition from operating in a first mode (e.g. youth mode) to operating in a second mode (e.g., adult mode) and vice versa, in response to detecting an input corresponding to a selection of a confirmation affordance (e.g. device will not transition operating modes without first confirming the users intent to initiation a mode transition).

FIGS. 7A-7D are a flow diagram illustrating a method for monitoring fitness activity using an electronic device in accordance with some embodiments. Method 700 is performed by an electronic device (e.g., 100, 300, 600, 800) with a display device and one or more sensors (e.g., accelerometers, GPS sensors; heart rate sensors). In some embodiments, the electronic device is a wearable device with an attachment mechanism, such as a band. Some operations in method 700 are, optionally, combined, the orders of some operations are, optionally, changed, and some operations are, optionally, omitted.

In some embodiments, the electronic device (e.g., 600) is a computer system. The computer system is optionally in communication (e.g., wired communication, wireless communication) with a display generation component and with one or more input devices. The display generation component is configured to provide visual output, such as display via a CRT display, display via an LED display, or display via image projection. In some embodiments, the display generation component is integrated with the computer system. In some embodiments, the display generation component is separate from the computer system. The one or more input devices are configured to receive input, such as a touch-sensitive surface receiving user input. In some embodiments, the one or more input devices are integrated with the computer system. In some embodiments, the one or more input devices are separate from the computer system. Thus, the computer system can transmit, via a wired or wireless connection, data (e.g., image data or video data) to an integrated or external display generation component to visually produce the content (e.g., using a display device) and can receive, a wired or wireless connection, input from the one or more input devices.

As described below, method 700 provides an intuitive way for monitoring fitness activity. The method reduces the cognitive burden on a user to monitor fitness activity, thereby creating a more efficient human-machine interface. For battery-operated computing devices, enabling a user to monitor fitness activity faster and more efficiently conserves power and increases the time between battery charges.

While the electronic device (e.g., device 600) is operating in a first device mode (e.g., youth mode) (e.g., device 600 in FIGS. 6A-6H), the electronic device detects (e.g., based on receiving updated information; based on a context of the device, such as the current date) (e.g., the current date indicates that a user is a different age, using birth date information) (702) a change in a first user physical characteristic (e.g., age; weight; body mass index) from a first physical characteristic value (e.g. user age of 17) to a second physical characteristic value (e.g., use age of 18) (e.g., FIGS. 6G and 6H, device 600 detects change in user age based on time and/or date).

In some embodiments, the first user physical characteristic is an age (e.g., in years) of a user associated with the electronic device, the first physical characteristic value is a first age value (e.g., a value less than 13 years; a value less than 17 years), and the second physical characteristic is a second age value, greater than the first age value (e.g., 13 years; 17 years).

In response to detecting the change in the first user physical characteristic (704), in accordance with a determination that the second physical characteristic value satisfies a set of mode change criteria (e.g., the second physical characteristic value exceeds a predetermined threshold; the second physical characteristic value matches one or more values in a predetermined set of values), the electronic device initiates (706) a process to transition (In some embodiments, completing the process) from the first device mode (e.g., youth mode) to a second device mode (e.g., adult mode) (e.g., device 600 displays user interface 654). Initiating (e.g., automatically, without further user input) the process to transition from the first device mode (e.g., youth mode) to the second device mode (e.g., adult mode) in accordance with the determination that the second physical characteristic value satisfies a set of mode change criteria enable a user to quickly and easily access the second device mode. Performing an operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, initiating the process to transition from the first device mode the second device mode includes displaying (708) a first confirmation user interface that includes a first confirmation affordance (e.g., "upgrade") (e.g., 656), receiving (710) an input corresponding the first confirmation affordance (e.g., 660), and in response to receiving the input corresponding the first confirmation affordance, transitioning (e.g., immediately transitioning, transitioning after a predetermined time; transitioning at a selected time (e.g., 12:00 AM)) (712) from the first device mode to the second device mode (e.g., 622B). In some embodiments, the confirmation user interface includes a dismiss/rejection affordance (e.g., 658) that, when selected, causes the device to remain in the first mode.

In some embodiments, detecting the change in a first user physical characteristic from a first physical characteristic value to a second physical characteristic value occurs at a first time. In some embodiments, initiating the process to transition from the first device mode to the second device mode includes transitioning from the first device mode to the second device mode at a second time, later than the first time, that is the next (e.g., upcoming) occurrence of a specific time of day (e.g., the next 12:00 AM) after the first time (e.g., 608B of FIG. 6K). In some embodiments, initiating the process to transition from a child mode to an adult mode takes place in the middle of a day (e.g., Monday) and transition to adult mode occurs beginning the next day (e.g., Tuesday).

In some embodiments, initiating the process to transition from the first device mode the second device mode includes transitioning from the first device mode to the second device mode. In some embodiments, after transitioning from the first device mode to the second device mode, the electronic device forgoes providing (714) an option (e.g., any option) to transition from the second device mode to the first device mode. Forgoing providing the option to transition from the second device mode to the first device mode after transitioning from the first device mode to the second device mode enables the device to be secured (e.g., locked) in the second device mode without being (e.g., unintentionally) reverted back to the first device mode, which in turn enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, the transition from the first device mode to the second device mode is not reversible, under normal use (e.g., without resetting the electronic device). In some embodiments, the second electronic device does not include (or provide) a discrete setting or option to transition from the second device mode the first device mode.

In response to detecting the change in the first user physical characteristic (704), in accordance with a determination that the second physical characteristic value does not satisfy a set of mode change criteria, the electronic device remains (716) in the first device mode (e.g., youth mode) (608A in FIG. 6G).

While the electronic device is operating in the first device mode (e.g., youth mode), the electronic device receives (718) first user activity data from the first set of sensors (e.g., data detected using one or more sensors of the device).

Subsequent to receiving the first user activity data, the electronic device displays (720) a first activity user interface that includes a first activity metric (e.g., a visual indication of the metric) based on (e.g., calculated from; derived from) the user activity data received from the first set of sensors (e.g. 616, 618, and 620 of FIGS. 6A and 6G) (e.g. 626 of FIG. 6B). In some embodiments, the first activity user interface does not include the second activity metric (e.g., 608A, 624A). In some embodiments, the first activity user interfaces includes an activity metric based on received activity data using a first unit of measure, for example, minutes of movement (e.g., 620A of FIG. 6A and 626A of FIG. 6B). Displaying (e.g., automatically, without further user input) the first activity user interface that includes the first activity metric when the electronic device is operating in the first device mode provides a user with quick and easy access to the activity metric that may be or is more likely to be relevant or useful to the user. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

While the electronic device is operating in the second device mode (e.g., adult mode) (722), the electronic device receives (724) second user activity data from the first set of sensors (e.g., data detected using one or more sensors of the device) (e.g., activity data displayed on user interface 608B is received).

While the electronic device is operating in the second device mode (e.g., adult mode) (722), subsequent to receiving the second user activity data, the electronic device displays (726) a second activity user interface (e.g., 608B) that includes a second activity metric, different from the first activity metric, based on (e.g., calculated from; derived from) the user activity data received from the first set of sensors. In some embodiments, the second activity user interface does not include the first activity metric (e.g. 608B, 624B). In some embodiments, the second activity user interface includes an activity metric based on received activity data using a second unit of measure, for example, calories burned (e.g., 608B, 624B). Displaying (e.g., automatically, without further user input) the second activity user interface that includes the second activity metric when the electronic device is operating in the second device mode provides a user with quick and easy access to the activity metric that may be or is more likely to be relevant or useful to the user. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, while the device is in a first respective device mode selected from a group consisting of the first device mode and the second device mode, the electronic device receives (728), from an external device (e.g., a smartphone that is paired with or connected to the electronic device) (e.g., device 500 in FIGS. 6R-6S), a request to transition a device mode (e.g., a request to transition to a different mode; a request to transition to a specific mode (e.g., specifically the first device mode or the second device mode)) (e.g., 694). In some embodiments, in response to receiving the request to transition a device mode, the electronic device transitions (730) to a second respective device mode selected from the group consisting of the first device mode and the second device mode, wherein the second respective device mode is different than the first respective device mode (e.g., if the first respective device mode is the first device mode, the second respective device mode is the second device mode, and vice versa).

In some embodiments, while the device is in a third respective device mode selected from a group consisting of the first device mode and the second device mode, the electronic device receives (732), from a second external device (e.g., a smartphone that is paired with or connected to the electronic device), a second request to transition a device mode (e.g., a request to transition to a different mode; a request to transition to a specific mode (e.g., specifically the first device mode or the second device mode)). In some embodiments, in response to receiving the second request to transition a device mode, the electronic device displays (734) a second confirmation user interface (e.g., 694) that includes a second confirmation affordance (e.g., 695) and a first rejection affordance (e.g., an interface to accept or reject the request to transition).

In some embodiments, while displaying the second confirmation affordance, the electronic device receives (736) a first input (e.g., 696). In some embodiments, in response to receiving the first input (738), in accordance with a determination that the first input corresponds to the second confirmation affordance, the electronic device transitions (740) to a second respective device mode selected from the group consisting of the first device mode and the second device mode, wherein the third respective device mode is different than the fourth respective device mode (e.g., if the third respective device mode is the first device mode, the fourth respective device mode is the second device mode, and vice versa) (e.g., 622A of FIG. 6U). In some embodiments, in response to receiving the first input (738), in accordance with a determination that the first input corresponds to the second confirmation affordance, the electronic device remains (742) in the third respective device mode (e.g., forgoing transitioning modes).

In some embodiments, the electronic device includes an input device (e.g., an integrated input device (e.g., a touch-sensitive surface)). In some embodiments, while the device is in a fifth respective device mode selected from a group consisting of the first device mode and the second device mode, the electronic device receives (744), via the input device, a third request to transition a device mode (e.g., a selection of a mode transition affordance). In some embodiments, in response to receiving the third request to transition a device mode, the electronic device transitions (746) to a sixth respective device mode selected from the group consisting of the first device mode and the second device mode, wherein the sixth respective device mode is different than the fifth respective device mode (e.g., if the fifth respective device mode is the first device mode, the sixth respective device mode is the second device mode, and vice versa).

In some embodiments, while the electronic device is operating in the first device mode, the electronic device displays (748) a first physical activity tracking user interface (e.g., a workouts user interface) (e.g., 676A) that includes a first set of one or more activity tracking affordances (e.g., 678A) that includes a first activity tracking affordance (e.g., an outdoor run affordance, an outdoor walk affordance) that, when selected, initiates a first activity tracking function (e.g., an outdoor run tracking function, an outdoor walk tracking function). In some embodiments, while the electronic device is operating in the second device mode, the electronic device displays (750) a second physical activity tracking user interface (e.g., a workouts user interface) (e.g., 676B) that includes a second set of one or more activity tracking affordances (e.g., 678B) that includes the first activity tracking and a second activity tracking affordance (e.g., a pool swim affordance) that, when selected, initiates a second activity tracking function (e.g., an pool swim tracking function), wherein the second activity tracking affordance is not included in the first physical activity tracking user interface (e.g., not included in the first set of one or more activity tracking affordances; not included in a default instance of the first physical activity tracking user interface). Displaying either the first physical activity tracking user interface or the second physical activity tracking user interface based on whether the electronic device is operating in the first device mode or the second device mode, respectively, provides a user with quick and easy access to the activity tracking user interface that is more relevant and/or more useful to the user, which in turn enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, youth mode top level workouts (e.g., the initial or first workout activities displayed when the workout application is launched)(e.g., 678A) include a subset set of the workouts in adult mode (e.g., youth mode includes outdoor run, outdoor walk, and outdoor cycle whereas adult mode includes a workouts in addition to outdoor run, outdoor walk, and outdoor cycle). In some embodiments, adult mode include a set of workouts corresponding to the workouts in youth mode (e.g., adult mode includes an outdoor run workout but it is optimized differently than the outdoor run workout in the youth mode) (e.g., 678B).

In some embodiments, while the electronic device is operating in the first device mode, the electronic device displays (752) a first settings user interface (e.g., a settings user interface for an activity-related application of the electronic device) (e.g., 690A) that includes a first set of one or more settings affordances (e.g., 692A) that includes a first setting affordance (e.g., an auto-pause affordance) that, when selected, alters a first setting (e.g., an auto-pause setting). In some embodiments, while the electronic device is operating in the second device mode, the electronic device displays (754) a second settings user interface (e.g., 690B) that includes a second set of one or more settings affordances (e.g., 692B) that includes the first setting affordance and a second setting affordance (e.g., a start workout reminder affordance) that, when selected, alters a second setting (e.g., setting that controls whether start workout reminders are sent), wherein the second setting affordance is not included in the first settings user interface (e.g., not included in the first set of one or more settings affordances; not included in a default instance of the first settings user interface). In some embodiments, the feature associated with the second setting affordance is disabled by default upon transitioning from the first device mode (e.g., youth mode) to the second device mode (e.g., adult mode). Displaying either the first settings user interface or the second settings user interface based on whether the electronic device is operating in the first device mode or the second device mode, respectively, provides a user with quick and easy access to the settings user interface that is more relevant and/or more useful to the user, which in turn enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first activity metric is a time-based activity metric (e.g., minutes of activity that met an activity threshold) (e.g., 616A of FIG. 6A). In some embodiments, the first activity metric is derived from another metric (e.g., an energy or calorie based metric) which is based on received activity data. In some embodiments, the second activity metric is an energy-based activity metric (e.g., calories) (e.g., 622B, "CAL" in FIGS. 6K and 6L). In some embodiments, the second activity metric is based at least in part on user-defined data (e.g., weight, height, sex, or age, etc.) (e.g., 668). In some embodiments, the second activity metric is based at least in part on data measured by the device (e.g., heart rate, historical motion data, etc.).

In some embodiments, displaying the first activity user interface includes displaying a first activity goal for the first activity metric (e.g., a target of 30 minutes of activity that exceeds an activity threshold), the first activity goal having a first value (e.g., 30 minutes) (e.g., 608A of FIG. 6A, 624A of FIG. 6B), and while displaying the first activity goal for the first activity metric, the electronic device receives a first set of one or more inputs (e.g., 622, 628, 634, 644) and in response to receiving the first set of one or more inputs (e.g., one or more inputs in a user interface for adjusting the activity goal value), the electronic device displays a second instance of the first activity user interface that includes a second activity goal for the first activity metric, the second activity goal having a second value (e.g., 60 minutes) different than the first value of the first activity goal (e.g., 624A of 6F and 608A of FIG. 6G).

In some embodiments, activity goals change to new defaults upon mode transition (e.g., from 10 stand hours for youth to 12 stand hours for adult, etc.) (e.g., 622A, 622B). In some embodiments, in response to adding to the top-level (e.g., default) workouts displayed in the child mode (e.g., via "more workouts" affordance), the electronic device displays a warning prompt about optimization (e.g., "adding additional workouts may result in inaccurate activity tracking"). Displaying the warning prompt about optimization enables a user to quickly and easily recognize that adding additional workouts may (e.g., negatively) influence the accuracy of the activity tracking of existing workouts. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, workouts added in youth mode appear in adult mode after the transition (e.g., if archery is added in youth mode, upon transition the default list of workouts includes all regular plus archery).

In some embodiments, the electronic device displays a welcome or setup prompt following a transition between modes (e.g., prompt displays current goals and personal info and provides affordances to edit) (e.g., 622A, 622B). In some embodiments, goals and personal info are changed via settings menu rather than from welcome/setup prompt. In some embodiments, the electronic device displays a warning prompt in response toggling modes at the device and requires confirmation before transitioning modes (e.g., 654, 694, 699).

Note that details of the processes described above with respect to method 700 (e.g., FIGS. 7A-7D) are also applicable in an analogous manner to the methods described below. For example, method 700 optionally includes one or more of the characteristics of the various methods described above with reference to method 900. For example, device 600 may display commentary (as described with respect to device 802 and device 804 of FIGS. 8A-8H below) while operating in a first device mode (e.g., youth mode) and display different commentary (as described with respect to device 800 of FIGS. 8A-8H below) while operating in a second device mode (e.g., adult mode). For brevity, these details are not repeated below.

FIGS. 8A-8H illustrate exemplary user interfaces for providing dynamic activity commentary, in accordance with some embodiments. In particular, FIGS. 8A-8H illustrate user interfaces for dynamically providing activity commentary in response to activity-based events (e.g., issue a congratulatory comment, encouraging statement, or new activity challenge when an activity-based goal is met or near completion) based on a characteristic of a user of a device (e.g., age). FIGS. 8A-8H contrast the corresponding user interfaces (e.g., user interfaces including textual and graphical content) provided by (e.g., displayed by) a device (e.g., device 800, device 802, device 804) under various scenarios related to monitoring or tracking physical activity (e.g., conditions triggering a device to display commentary) while a device operated by users having different characteristics (e.g., users having an age determined to be within a set of predetermined age ranges, for example, below 9 years of age, between 9 and 12 years of age, and above 12 years of age). In some embodiments, simplified stand reminders, daily coaching, goal completion notifications, activity summaries, and special challenge notifications are provided to a first class of users and not a second class of user.

In some embodiments, a characteristic of a user includes an input by the user indicative of cognitive ability (e.g., age of the user, highest level of education of the user, a standardized test score of the user). In some embodiments, the user inputs information related to the characteristic (e.g., cognitive ability). For example, the user may input information during an initial setup of the device 800, the device 802, and/or the device 804 related to the age of the user, the highest level of education of the user (e.g., grade school class, expected high school or college graduation date, master's degree, doctorate degree, professional degree), a standardized test result achieved by the user (e.g., National Assessment of Educational Progress (NAEP), Metropolitan Achievement Test (MAT8), one or more state administered standardized tests, such as the California Standardized Testing and Reporting (STAR), the Texas Assessment of Knowledge and Skills (TAKS), and the New York State Testing Program (NYSTP)), and/or an option selected by the user related to the user's preference for activity commentary (e.g., a sample activity commentary of a plurality of sample activity commentaries that the user comprehends best and/or, an option to use emoji characters in activity commentary). In some embodiments, the output of activity commentary is based on the information inputted by the user.

Throughout FIGS. 8A-8H, device 800, device 802, and device 804 (and the user interfaces each respective device is depicted displaying) are each associated with (e.g., operated by) a user with a of user of a different age. Device 800 is associated with a user of an age within a first age range (e.g., age 13 years or older). Device 802 is associated with a user of an age within a second age range (e.g., age 9 years to 12 years). Device 804 is associated with a user of an age within a third age range (e.g., less than 9 years).

In some embodiments, device 800, device 802, and device 804 (hereafter, collectively referred to as "the group of devices") determine an age of a user by interpreting age data received at the respective device (e.g., configuration information or profile information inputted at the respective device or otherwise conveyed to and/or received by the respective device). In some embodiments, device 800, device 802, and device 804 determine an age of a user by comparing age data received at the device to data representing a current date. The user interfaces in these figures are used to illustrate the processes described below, including the processes in FIGS. 9A-9B.

Figure 8A:
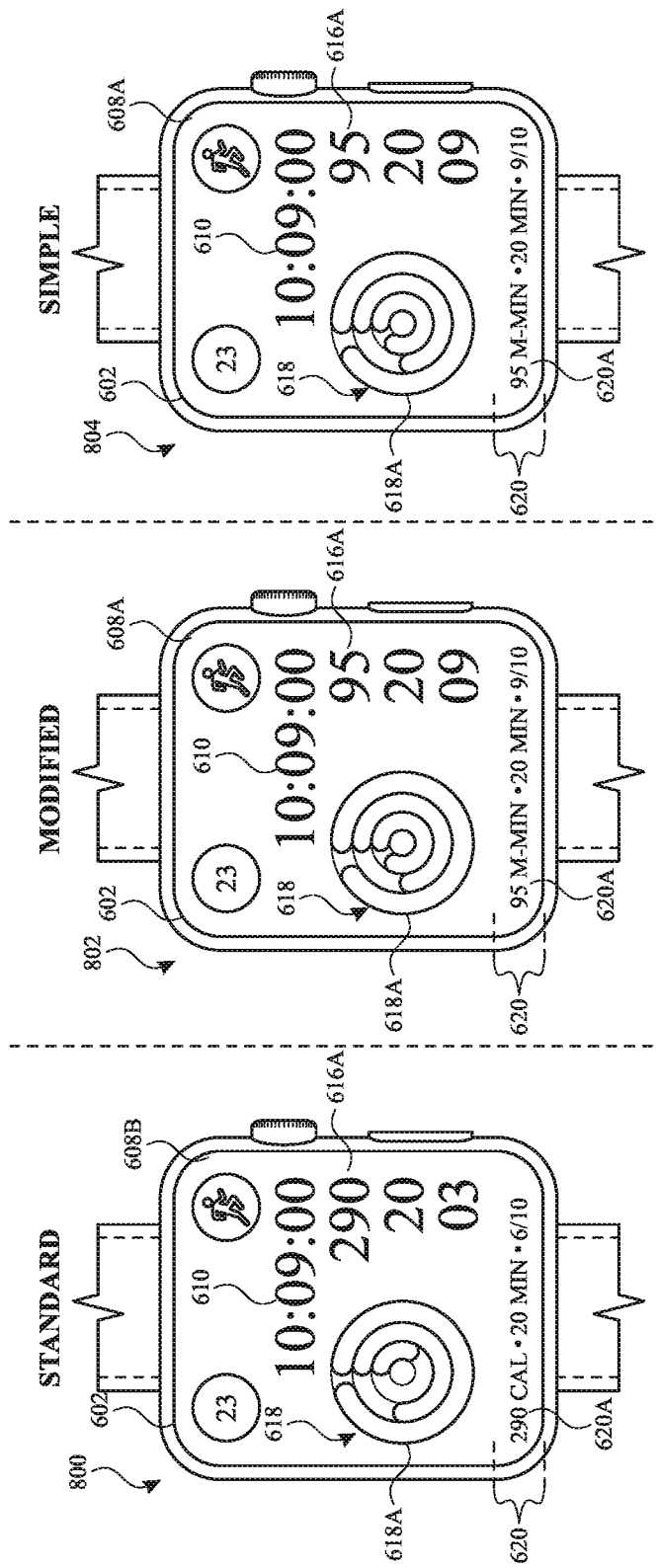
FIGS. 8A-8H illustrate exemplary user interfaces for monitoring fitness activity.
Figure 9A:
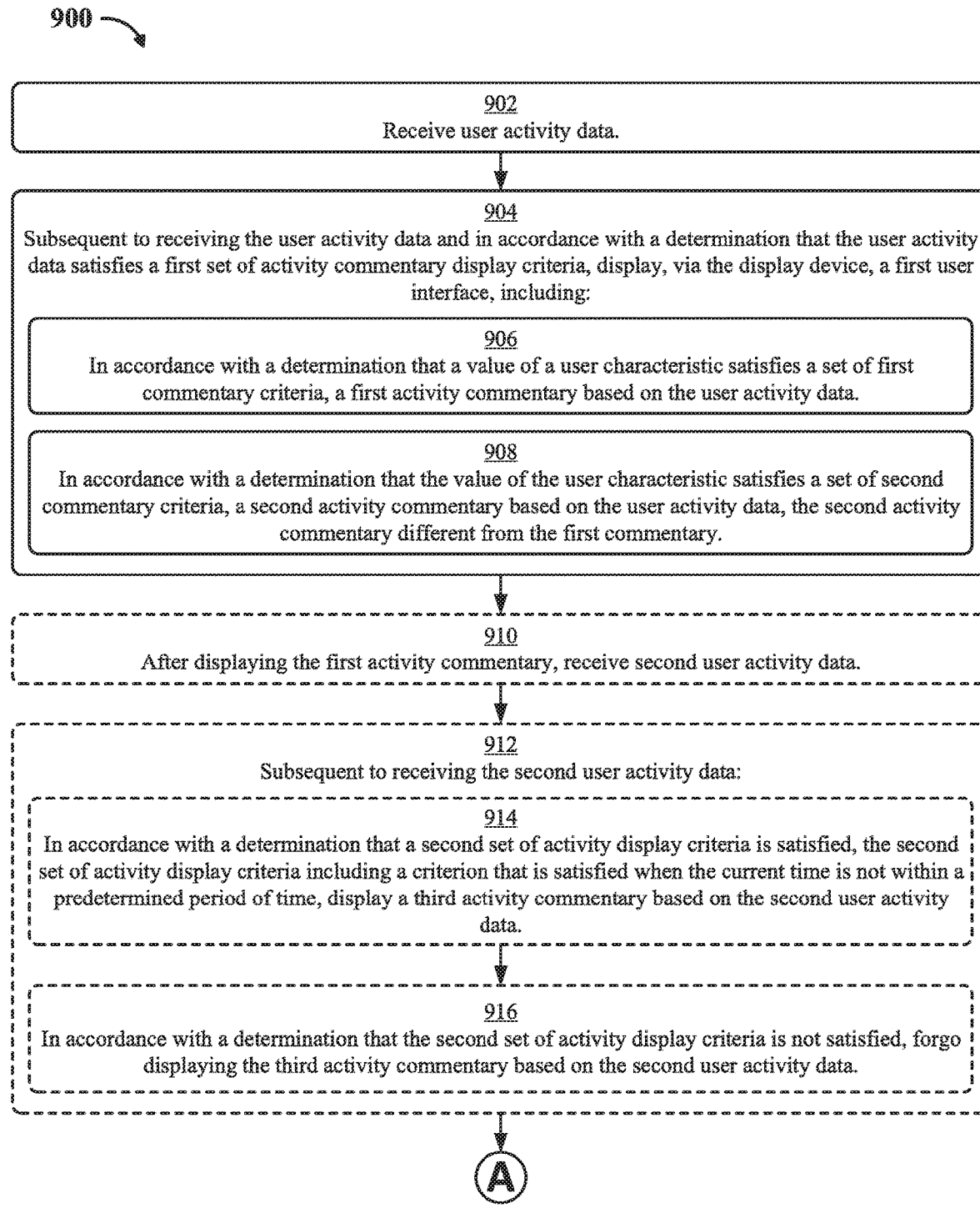
FIGS. 9A-9B illustrate flow diagram depicting a method for providing user interfaces in accordance with some embodiments.
Figure 9B:
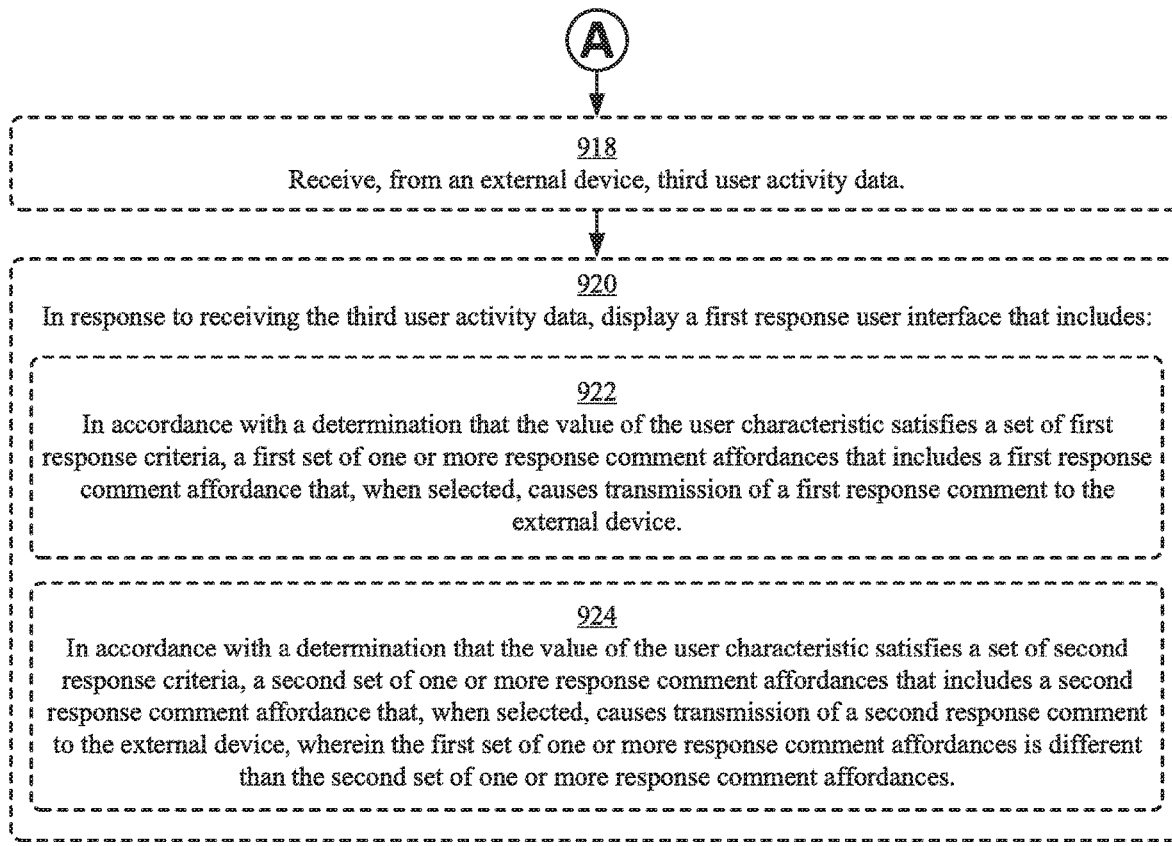

FIG. 8A depicts device 800, device 802, and device 804 (e.g. each device as described above with respect to device 600 in FIG. 6A). As depicted in FIG. 8A, device 800 displays clock user interface 608B (e.g., as described above with respect to FIG. 6J) and device 802 and device 804 display clock user interface 608A (e.g., as described above with respect to FIG. 6A). Clock user interface 608B (left illustration) and clock user interface 600A (center and right illustrations) each indicate a current time 10:09:00 in the evening (e.g., as depicted by time indicator 610) and indicate a move metric goal is near completion (e.g., activity ring 618-A has nearly completed 360 degrees of rotation).

Figure 8B:
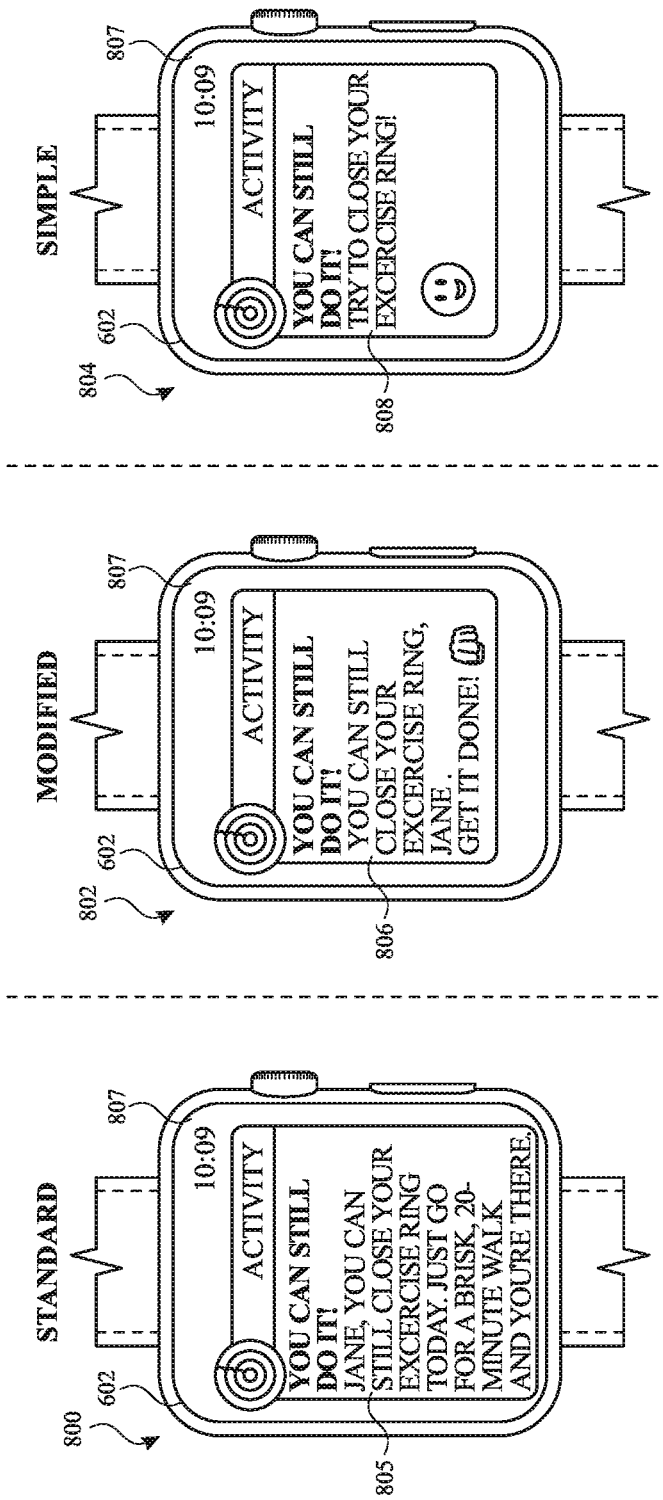

FIG. 8B depicts the group of devices displaying an evening update user interface 802 after a first set of commentary triggering conditions have been met. For example, in some embodiments, the devices display evening update user interface 807 after determining that a predetermined portion (e.g., 75%) of a current day has elapsed and that an activity metric is within a predetermined threshold (e.g., 5%) of completion. In some embodiments, the group of devices determine that a predetermined portion of a current day has elapsed based on a current time. In some embodiments, the group of devices determine that an activity metric is within a predetermined threshold of completion based on received activity data. In some embodiments, the group of devices determines a set of commentary criteria have been met based on or more of a current time, a current day, received activity data, a device status, or the like.

As depicted by FIG. 8B, the group of devices display evening update user interface 807, however, evening update user interface 807 includes different commentary (e.g., evening prompt 805, evening prompt 806, evening prompt 808), depending on the age of the user associated with each respective devices (e.g., as discussed above, device 800 is associated with a user of an age within a first age range, device 802 is associated with a user of an age within a second age range, device 804 is associated with a user of an age within a third age range). As depicted by FIG. 8B, evening prompt 805 is longer than evening prompt 806. Likewise, evening prompt 806 is longer than evening prompt 808. In some embodiments, the total characters included in displayed commentary is below a respective threshold amount of characters based on an age of a user of a device (e.g., maximum prompt lengths are higher for older or more mature device users). In some embodiments, each word included in displayed commentary is below a respective threshold amount of characters based on an age of a user of a device (e.g., maximum word length is higher for older or more mature device users).

As depicted by FIG. 8B, evening prompt 806 and evening prompt 808 include graphical content (e.g. emojis), whereas, evening prompt 804 does not include graphical content. In some embodiments, the amount of graphical content included in displayed commentary is based in part on a characteristic of a user the device (e.g., emojis are displayed to younger device users (e.g., ages 6-9) and not displayed to older device users (e.g., ages above 9)). In some embodiments, the ratio of graphical content (e.g., emojis) to textual content (e.g., characters) included in displayed commentary is based in part on a characteristic of a user the device (e.g., the ratio is higher in devices for younger users and lower in devices for older users).

In some embodiments, commentary is simplified for younger users (e.g., feedback is limited to activity ring goals for youngest users whereas feedback for older users may include activity ring goals in addition to other types goals (e.g., total calorie burn, total distance, etc.)). In some embodiments, commentary progressively increases the use of advanced concepts (e.g., long term goals) as user age increases. In some embodiments, monthly challenges for young users are limited to activity ring metrics (e.g., move minutes, stand hours, and workout minutes). In some embodiments, monthly challenges for young users are do not include specific workouts or total distance goals, etc.

As depicted by FIG. 8B, evening update prompt 805 includes activity-based instructions (e.g., " . . . go for a brisk, 20-minute walk") to accomplish an activity goal, whereas, evening prompt 806 and evening prompt 808 do not include activity-based instructions. In some embodiments, the amount or inclusion of activity-based instructions in displayed commentary is based in part on a characteristic of a user the device (e.g., more activity-based instructions are displayed to older or more mature device users than to younger device users.

Figure 8C:
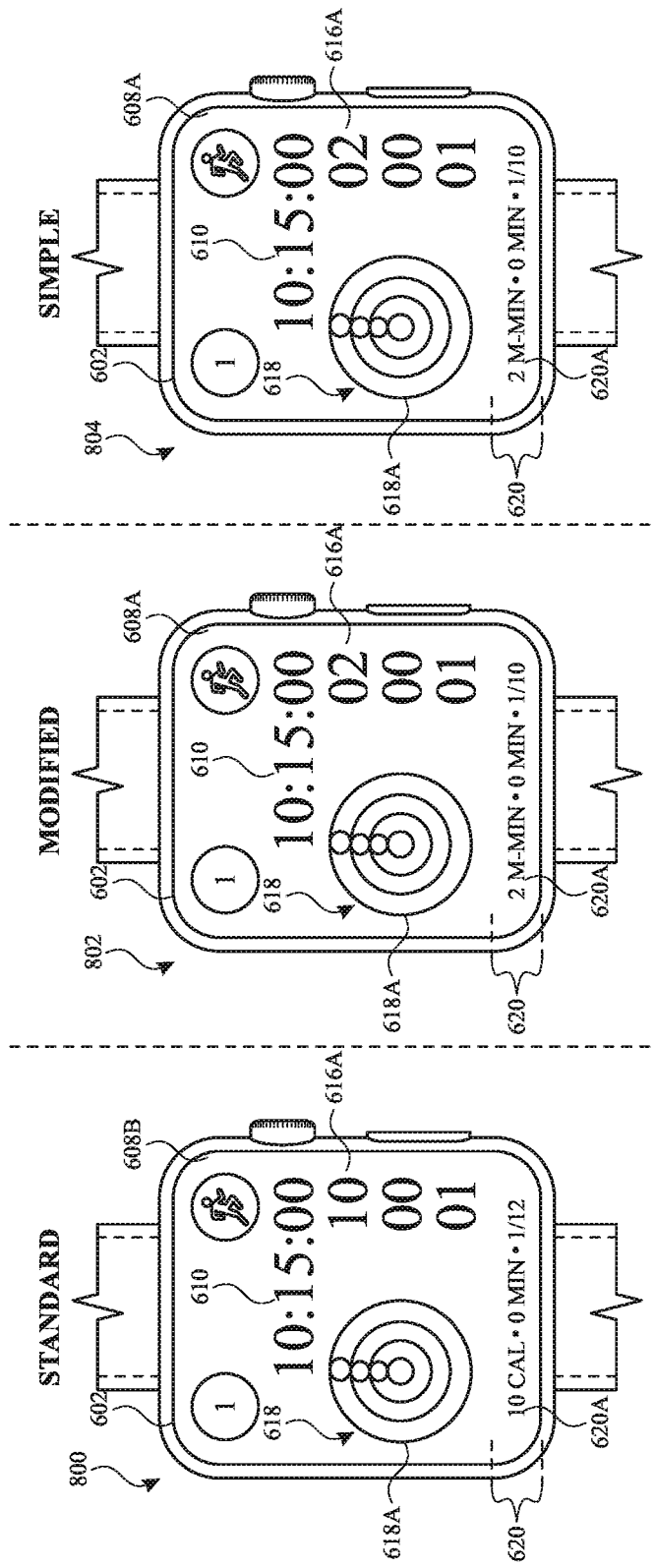

FIG. 8C depicts the group of devices (e.g., device 800, 802, and 804) at a first time, just prior to a second set of commentary triggering conditions being met. In FIG. 8C, device 800 displays clock user interface 608B, device 802 displays clock user interface 602A, and device 804 displays clock user interface 608A. As depicted in FIG. 8C, the group of devices indicate a current time of 10:15 am on a first day of a current month (e.g., as indicated by time indicator 610 and date affordance 612).

Figure 8D:
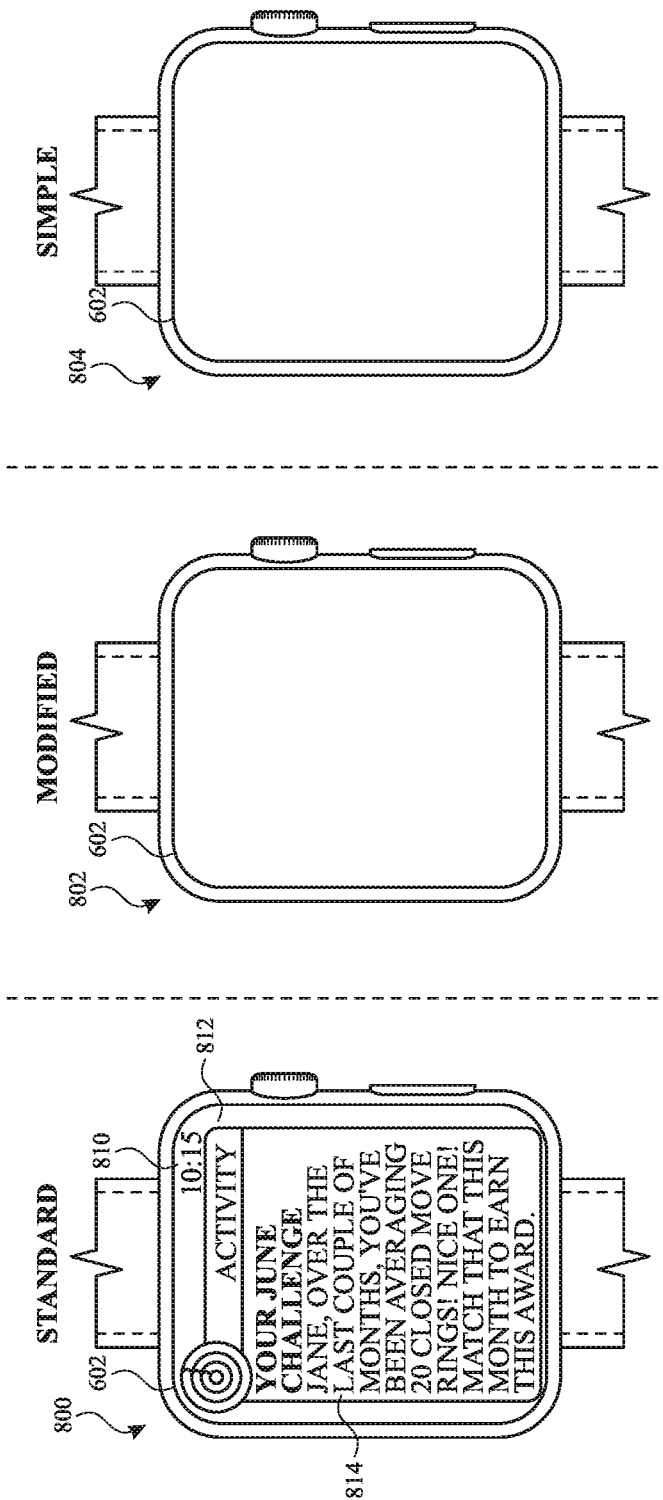

FIG. 8D depicts the group of devices at a second time after the second set of commentary triggering conditions have been net. For example, FIG. 8D depicts the appearance of the devices (e.g., the content displayed by each device) upon determining that a predetermined period of time (e.g., 10-minutes) has elapsed since each device detected an on-wrist condition (e.g., the device detected that the user put the watch on at approximately 10:05 am). As depicted in FIG. 8D, the group of devices display or forgo displaying activity challenge user interface 814 (e.g. a notification with associated commentary), depending on the age of the user associated with each respective device. For example, device 800 (e.g., a device associated a user above the age of 12) displays activity challenge user interface 814 (e.g. a notification) including prompt 812. (e.g., commentary). In contrast, device 802 and device 804 (e.g. each device associated with younger users) do not display activity challenge user interface 814 (e.g., their displays remain off) at the second time.

Figure 8E:
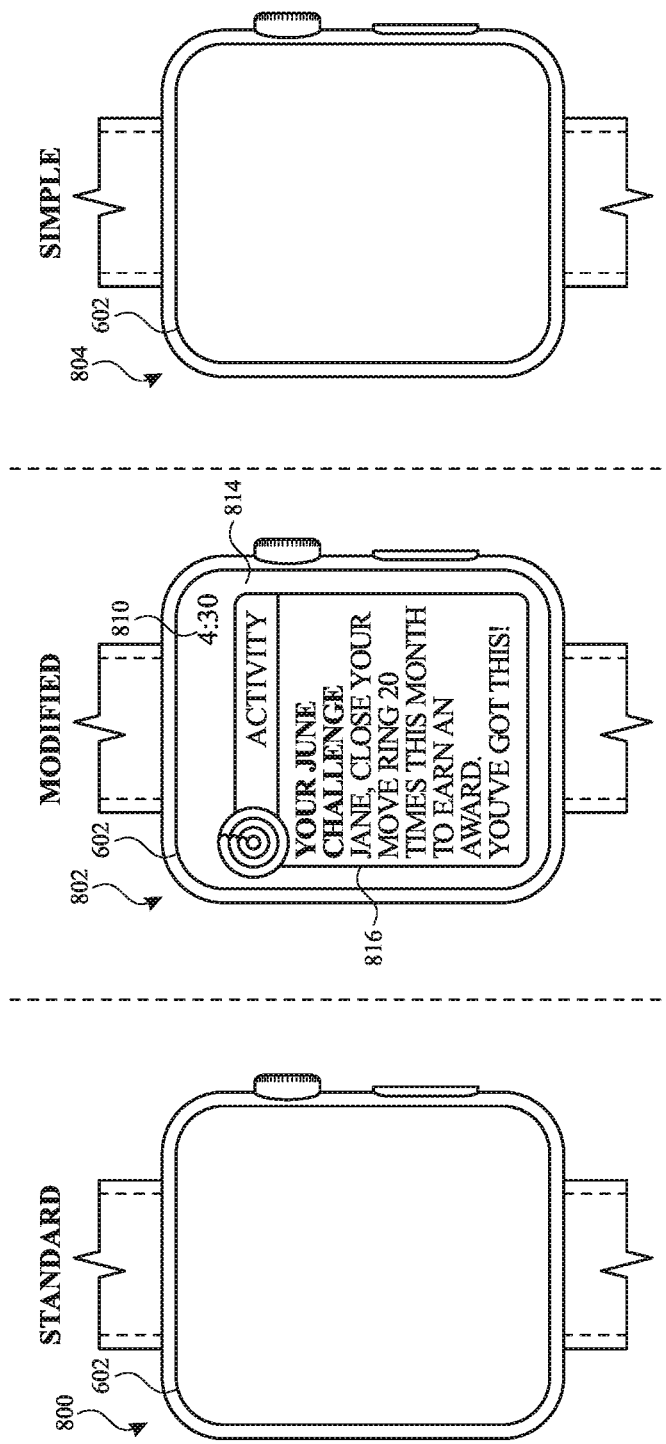

FIG. 8E depicts the group of devices at a third time after the second time (e.g., 4:30 pm as indicated by time indicator 810). As depicted in FIG. 8E, the group of devices display or continue to forgo displaying activity challenge user interface 814 (e.g. a notification), depending on the age of the user associated with each respective device. For example, device 802 (e.g., a device associated with a 9-12 year old user) displays activity challenge user interface 814 (e.g. a notification) including prompt 816. In contrast, device 804 continues to forgo displaying activity challenge user interface 814. In some embodiments, display commentary such as activity challenge user interface 814 is forgone indefinitely based on the age of the user associated with each the device. In some embodiments, commentary is suppressed (e.g., no commentary is issued) during typical school hours for school-aged users (e.g. age 6-12, 4-12, 4-18, or 6-18). In some embodiments, commentary is suppressed (e.g., no commentary is issued) during a predetermine sleeping period (e.g., past a bedtime). In some embodiments, commentary is suppressed (e.g., no commentary is issued) during one or more periods associated with predetermined schedule based on an age of a user.

Figure 8F:
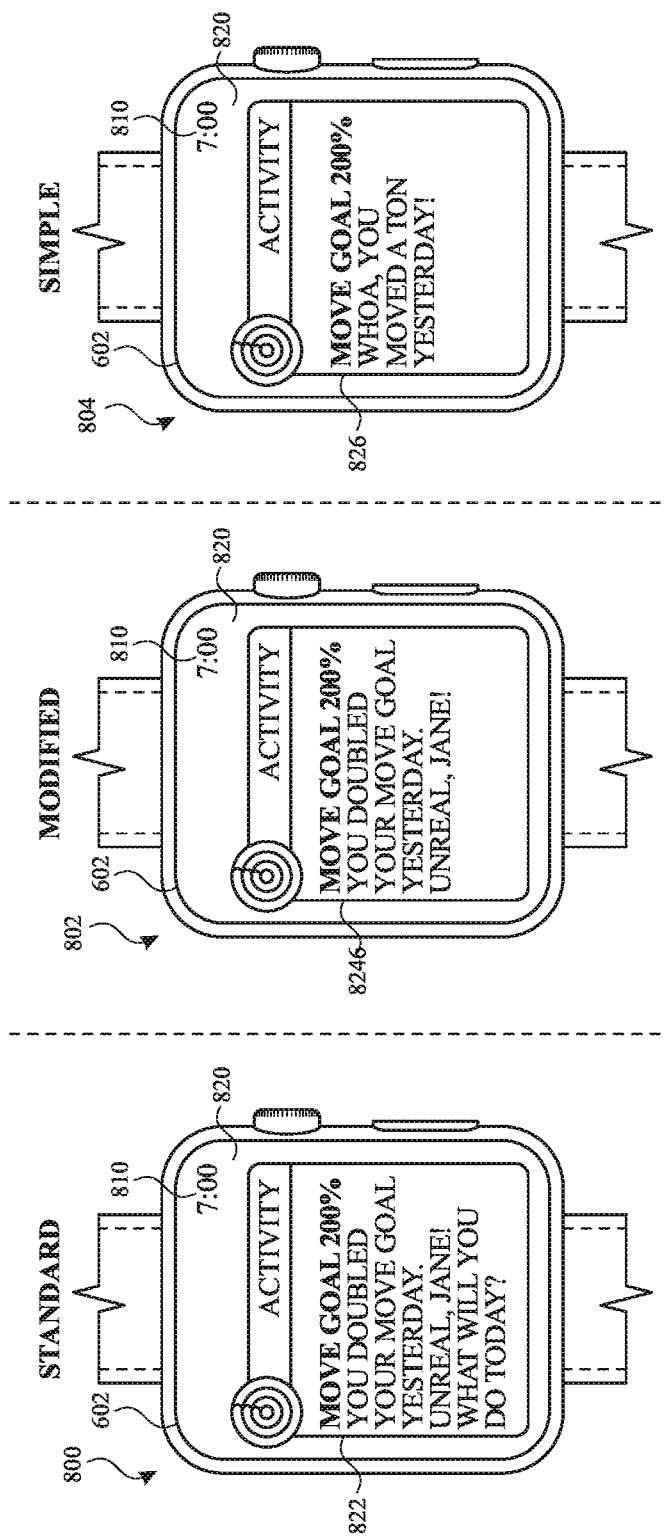

FIG. 8F depicts the group of devices after a third set of commentary triggering conditions are met. For example, the group of devices displays morning user interface 820 after determining that a current time has reached a predetermined time (e.g. 7:00 am) and after determining that one or more activity metric goals were exceeded by predetermined amount (e.g., by 200%, 300%, 400%) during a previous day.

As depicted by FIG. 8F, the group of devices each display morning user interface 820, however, morning user interface 820 includes different commentary (e.g., morning prompt 822, morning prompt 824, morning prompt 826), depending on the age of the user associated with each respective devices (e.g., as discussed above, device 800 is associated with a user of an age within a first age range, device 802 is associated with a user of an age within a second age range, device 804 is associated with a user of an age within a third age range).

As depicted by FIG. 8F, morning prompt 822 and morning prompt 824 include a textual reference to a mathematical concept (e.g., "doubled") while, morning prompt 826 does not include a textual reference to a mathematical concept. In some embodiments, the inclusion of mathematical concepts (e.g., references to averages, doubling, tripling, quadrupling, etc.) in displayed commentary is based on a characteristic (e.g., age) of a user of a device (e.g., only prompts for older or more mature device users include mathematical concepts). In some embodiments, the quantity (e.g., number) of mathematical concepts in displayed commentary is based on a characteristic (e.g., age) of a user of a device.

As depicted by FIG. 8F, morning prompt 822 includes an interrogatory statement (e.g., a question) while, morning prompt 824 and morning prompt 826 do not include an interrogatory statement. In some embodiments, the inclusion of interrogatory statements in displayed commentary on a characteristic (e.g., age) of a user of a device (e.g., the amount of interrogatory statements included in commentary is proportional to the or more mature device users). In some embodiments, the quantity (e.g., number) of interrogatory statements in displayed commentary is based on a characteristic (e.g., age) of a user of a device.

Figure 8G:
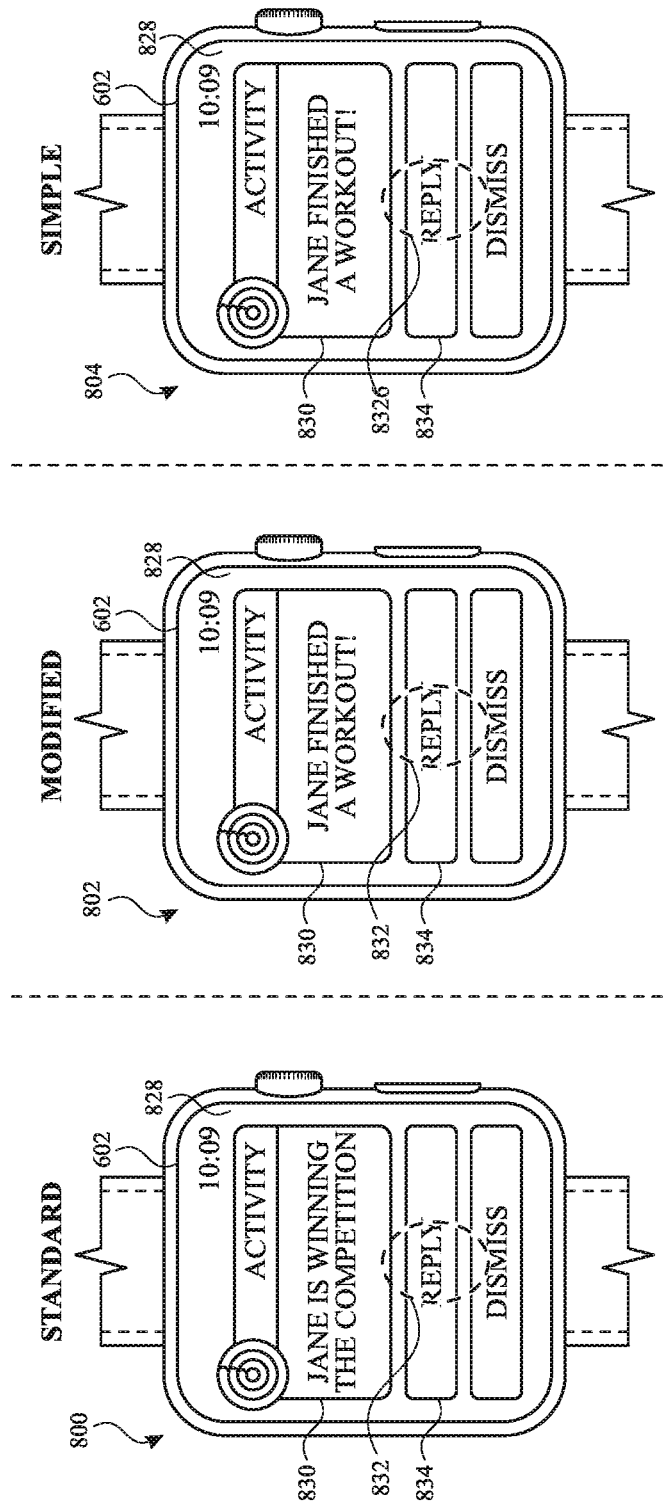

FIG. 8G depicts the group of devices displaying recent activity user interface 828 (e.g., an interface including a notification) after receiving activity data from an external device. In some embodiments, the received activity data indicates a friend or parent is ahead of the user in a fitness-based competition or indicates a friend or parent recently completed a workout). As depicted in FIG. 8G, recent activity user interface 828 includes activity description 830 and reply affordance 832. FIG. 8G depicts the group of devices receiving user input 832 (e.g., a tap) corresponding to selection of reply affordance 832. In response to user input 832, the group of devices display user interface 836 as depicted in FIG. 8H.

Figure 8H:
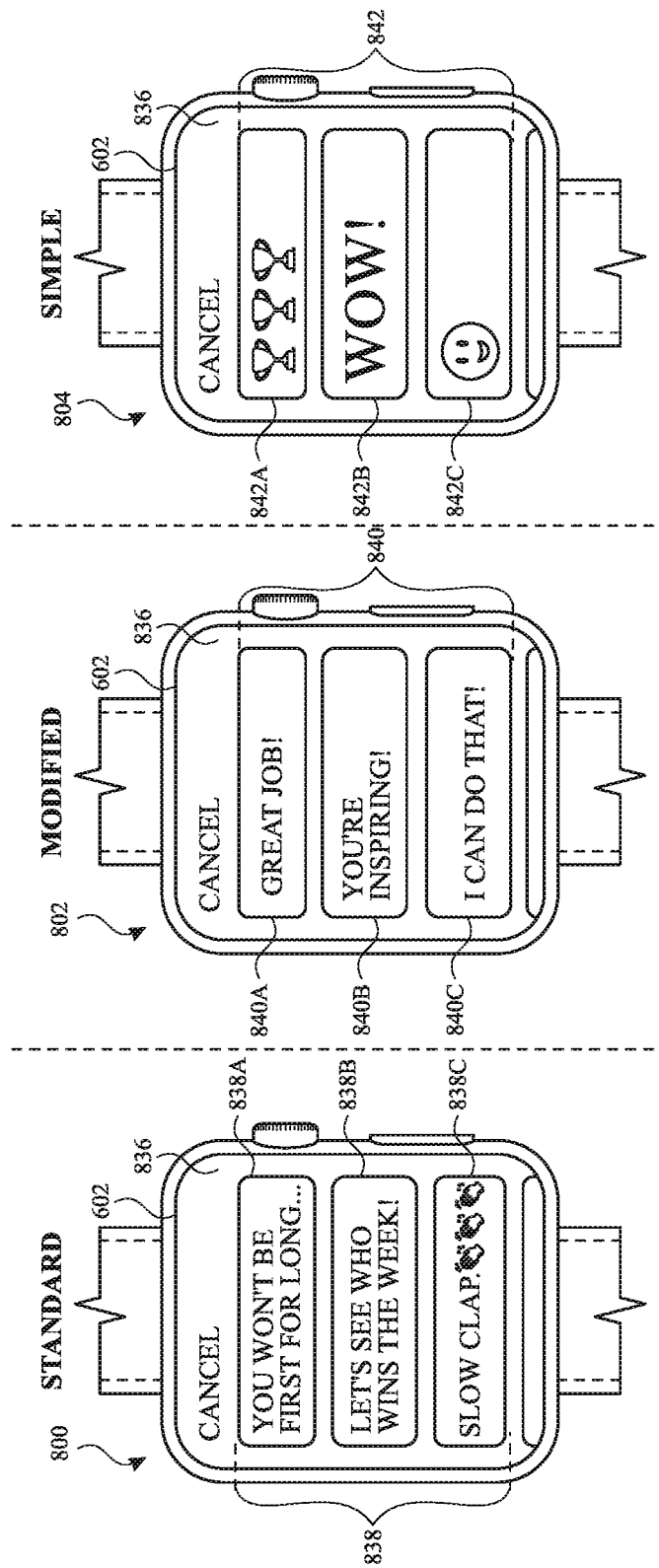

As depicted in FIG. 8H, user interface 836 includes a different set of response affordances (e.g., 838, 840, and 842) depending on a characteristic (e.g., age) of the user of the device. Each set of response affordances is associated with a set of predetermined statements (e.g., the content displayed on each individual affordance), which are transmitted to the external device (e.g., the device associated with the received activity data). In some embodiments, data representing a respective predetermined statement is sent via a text message or message associated with an activity or workout application. However, the content of the predetermined statements associated with (and displayed by) each set of response affordances (e.g., 838, 840, and 842) is based on the age of the user associated with the respective device (e.g., as discussed above, device 800 is associated with a user of an age within a first age range, device 802 is associated with a user of an age within a second age range, device 804 is associated with a user of an age within a third age range).

As depicted by FIG. 8H, set of response affordances 838 includes predetermined statements (e.g., commentary) which include dismissive (e.g., sarcastic) remarks (e.g., 838C) and aggressive (e.g., inflammatory) language (e.g., 838A, 838B). In contrast, set of response affordances 840 and set of response affordances 842 do not include predetermined statements (e.g., commentary) which include dismissive remarks or aggressive language (e.g., 840A, 840B, 840C, 842A, 842B, and 842C each correspond to remarks with a positive sentiment or are otherwise non-inflammatory). In some embodiments, the sentiment of content included in displayed commentary is based in part on a characteristic of a user the device (e.g., commentary is with a negative sentiment is displayed to older device users (e.g., ages above 12) but not to younger device users (e.g., ages below 12). In some embodiments, a set of available commentary associated with response affordances on a device associated with a user having a first characteristic (e.g., age below 9) is a subset of a larger set of available commentary associated on a device associated with a user having a second characteristic (e.g., age 9-12 or above 12).

FIGS. 9A-9B is a flow diagram illustrating a method for dynamically providing activity commentary using an electronic device, in accordance with some embodiments. Method 900 is performed at a first electronic device (e.g., 100, 300, 500, 600, 800) that includes a display device. In some embodiments, the first electronic device is a wearable device with an attachment mechanism, such as a band. Some operations in method 900 are, optionally, combined, the orders of some operations are, optionally, changed, and some operations are, optionally, omitted.

In some embodiments, the electronic device (e.g., 800) is a computer system. The computer system is optionally in communication (e.g., wired communication, wireless communication) with a display generation component and with one or more input devices. The display generation component is configured to provide visual output, such as display via a CRT display, display via an LED display, or display via image projection. In some embodiments, the display generation component is integrated with the computer system. In some embodiments, the display generation component is separate from the computer system. The one or more input devices are configured to receive input, such as a touch-sensitive surface receiving user input. In some embodiments, the one or more input devices are integrated with the computer system. In some embodiments, the one or more input devices are separate from the computer system. Thus, the computer system can transmit, via a wired or wireless connection, data (e.g., image data or video data) to an integrated or external display generation component to visually produce the content (e.g., using a display device) and can receive, a wired or wireless connection, input from the one or more input devices.

As described below, method 900 provides an intuitive way for dynamically providing activity commentary. The method provides a user with decipherable commentary that quickly draws the user's attention to relevant information (e.g., a coaching advice, encouraging statements, fitness data, etc.) and/or reduces the cognitive burden on a user for identifying a state of a device (e.g., a current activity metric as measured by a device), thereby creating a more efficient human-machine interface. Providing improved visual feedback to the user enhances the operability of the device and makes the user-device interface more efficient (e.g., by helping the user to quickly resolve the displayed information, the user does not need to spend as much time interacting with the device) which, additionally, reduces power usage and improves battery life of the device by enabling the user to use the device more efficiently.

The first electronic device receives (902) user activity data (e.g., data representing recorded movement of the user of the device) (e.g., activity data depicted by 616, 618, 620 of FIG. 8A).

Subsequent to receiving the user activity data and in accordance with a determination that the user activity data satisfies a first set of activity commentary display criteria (e.g., the data indicates that an activity goal/threshold is met or nearly met (e.g., 618A), a workout is completed, an activity achievement is earned, a lead change in an activity competition, activity is below a threshold level), the first electronic device displays (904), via the display device, a first user interface (e.g., 807). Displaying (e.g., automatically, without further user input) the first user interface subsequent to receiving the user activity data and in accordance with a determination that the user activity data satisfies a first set of activity commentary display criteria provides quick access to the first user interface when the interface may be (e.g., is likely to be) needed or useful to the user. Performing an operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In accordance with a determination that a value of a user characteristic (e.g., user age; user weight; user body mass index; education level of user; standardized test result achieved by user; option selected by user) satisfies a set of first commentary criteria (e.g., user age greater than 9; user education level above third grade; user standardized test result achieved within a first threshold range) (e.g., user of device 802), the first user interface includes a first activity commentary based (e.g., 806) on the user activity data (e.g., a congratulatory comment, encouraging or coaching statement, activity reminder, or new activity challenge when an activity ring is closed or near closing) (906). In some embodiments, commentary criteria includes a user age determined to be within a range, for example, ages 6-9, and 9-13. In some embodiments, the value of the user characteristic is received from another device (e.g., from a server storing profile data for the user). Including the first activity commentary based on the user activity data in the first user interface in accordance with a determination that a value of a user characteristic (e.g., user age; user weight; user body mass index; education level of user; standardized test result achieved by user; option selected by user) satisfies the set of first commentary criteria provides a user with quick and easy access to relevant and/or useful information. Performing an operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In accordance with a determination that the value of the user characteristic (e.g., user age; user weight; user body mass index; education level of user; standardized test result achieved by user; option selected by user) satisfies a set of second commentary criteria (e.g., user age 6-9; user education level between first and third grade; user standardized test result achieved within a second threshold range (e.g., second threshold range includes lower scores than first threshold range)) (e.g., user of device 804), the first user interface includes a second activity commentary (e.g., 808) based on the user activity data, the second activity commentary different from the first commentary (e.g., simplified versions of first activity commentary) (908). In some embodiments, simplified commentary such as stand reminders, daily coaching statements, goal completion notifications, and activity challenge notifications are provided to a first class of users and not a second class of user. In some embodiments, the set of second commentary criteria are satisfied when the set of first commentary criteria are not satisfied. In some embodiments, the value of the user characteristic is received from another device (e.g., from a server storing profile data for the user). Including the second activity commentary based on the user activity data in the first user interface in accordance with a determination that a value of a user characteristic (e.g., user age; user weight; user body mass index; education level of user; standardized test result achieved by user; option selected by user) satisfies the set of second commentary criteria provides a user with quick and easy access to relevant and/or useful information. Performing an operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the user characteristic is an age (e.g., in years) of a user associated with the first electronic device (e.g., 800, 802, 804). In some embodiments, the first set of first commentary criteria includes a criterion that is satisfied when the age of the user associated with the first electronic device is below a predetermined threshold value (e.g., user of device 802).

In some embodiments, the first activity commentary (e.g., 806) has a first length (e.g., word count, letter count) and the second activity commentary (e.g., 808) has a second length that is greater than the first length. In some embodiments, the first activity commentary is formatted (e.g., selected, sized) according to a first commentary template that includes a maximum length limit that is less than a maximum length limit of a second commentary template that the second activity commentary is formatted with.

In some embodiments, in accordance with (e.g., a determination that) the value of the user characteristic being within a first predetermined range, the first activity commentary (e.g., 806, 808) includes a graphical element (e.g., an emoji, an icon, an image) based on the user activity data (e.g., based on a value of the user activity data) and in accordance with the value of the user characteristic not being within the first predetermined range, the first activity commentary (e.g., 805) does not include a graphical element (e.g., an emoji, an icon, an image) based on the user activity data (e.g., based on a value of the user activity data). Including the graphical element based on the user activity data in accordance with (e.g., a determination that) the value of the user characteristic being within the first predetermined range and not including the graphical element based on the user activity data in accordance with the value of the user characteristic not being within the first predetermined range enables a user improves visual feedback by providing the graphical element to a user and/or in a situation where the graphical element is more likely to be helpful. Providing improved visual feedback to the user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, after displaying the first activity commentary, the first electronic device receives (910) second user activity data (e.g., activity data depicted by 616, 618, 620 of FIG. 8C). In some embodiments, subsequent to receiving the second user activity data (912), in accordance with a determination that a second set of activity display criteria (e.g., the data indicates that an activity goal/threshold is met or nearly met; the first set of activity commentary display criteria) is satisfied (e.g., FIG. 8C), the second set of activity display criteria including a criterion that is satisfied when the current time is not within a predetermined period of time (e.g., between the hours of 8 AM and 3 PM; a period of time that corresponds to an expected event (e.g., a school day; sleeping schedule)), the first electronic device displays (914) a third activity commentary (e.g., 814, 816) based on the second user activity data. In some embodiments, subsequent to receiving the second user activity data (912), in accordance with a determination that the second set of activity display criteria (e.g., the data indicates that an activity goal/threshold is met or nearly met; the first set of activity commentary display criteria) is not satisfied, the first electronic device forgoes displaying (916) the third activity commentary based on the second user activity data (e.g., 802 and 804 in FIG. 8D). In some embodiments, displaying the third activity commentary (e.g., 816 and 804 in FIG. 8E) is delayed until the second set of activity display criteria are met.

In some embodiments, the first electronic device receives (918), from an external device, third user activity data (e.g., user activity data for a user other than the user associated with the user activity data) (e.g., 830). In some embodiments, the third activity data indicates that an activity goal/threshold is met or nearly met, a workout is completed, an activity achievement is earned, a lead change in an activity competition, activity is below a threshold level. In some embodiments, in response to receiving the third user activity data, the first electronic device displays (922) a first response user interface (e.g., an interface for sending a response to the external device) (e.g., 828). Displaying the first response user interface in response to receiving the third user activity data provides a user with quick and easy access to information corresponding to the third activity data. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently. In some embodiments, in accordance with a determination that the value of the user characteristic satisfies a set of first response criteria, the first response user interface includes a first set of one or more response comment affordances (e.g., 840) that includes a first response comment affordance that, when selected, causes transmission of a first response comment to the external device (922). In some embodiments, in accordance with a determination that the value of the user characteristic satisfies a set of second response criteria, the first response user interface includes a second set of one or more response comment affordances (e.g., 842) that includes a second response comment affordance that, when selected, causes transmission of a second response comment to the external device, wherein the first set of one or more response comment affordances is different than the second set of one or more response comment affordances (e.g., the first set does not include the second response comment affordance; the second set does not include the first response comment affordance) (924).

In some embodiments, prior to receiving the user activity data (e.g., activity data depicted by 616, 618, 620 of FIG. 8A), the first electronic device receives the value of the user characteristic via a user input (e.g., user characteristic is input by user during set-up of the first electronic device prior to the first electronic device collecting activity data). Enabling a user to input the user characteristic provides the user with additional control over the activity commentary that is displayed by the device. The additional control over the activity commentary provides the user with enhanced visual feedback of relevant and/or useful information. Providing improved visual feedback to the user enhances the operability of the device and makes the user-device interface more efficient (e.g., by helping the user to provide proper inputs and reducing user mistakes when operating/interacting with the device), which additionally, reduces power usage and improves battery life of the device by enabling the user to use the device more quickly and efficiently.

In some embodiments, the value of the user characteristic is selected from the group consisting of age (e.g., one or more age thresholds, one or more age range thresholds), a highest level of education of a user (e.g., one or more grade level thresholds, one or more grade level range thresholds), a standardized test result achieved by the user (e.g., one or more score thresholds, one or more score range thresholds), an option selected by the user (e.g., first electronic device receives user input corresponding to selection of an option of a plurality of options related to example activity commentary), and any combination thereof. In some embodiments, standardized test results may include National Assessment of Education Progress (NAEP), Metropolitan Achievement Test (MAT8), one or more state administered standardized tests, such as the California Standardized Testing and Reporting (STAR), the Texas Assessment of Knowledge and Skills (TAKS), and the New York State Testing Program (NYSTP). In some embodiments, a user selects an option of activity commentary that the user best comprehends or understands.

Note that details of the processes described above with respect to method 900 (e.g., FIGS. 9A-9B) are also applicable in an analogous manner to the methods described above. For example, method 900 optionally includes one or more of the characteristics of the various methods described above with reference to method 700. For example, a mode in which the device is operating in—a first device mode (e.g., a youth mode) and a second device mode (an adult mode)—can be used to at least in part determine the type of commentary to display on the device. For brevity, these details are not repeated below.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

As described above, one aspect of the present technology is the gathering and use of data available from various sources to improve the delivery to users of invitational content or any other content that may be of interest to them. The present disclosure contemplates that in some instances, this gathered data may include personal information data that uniquely identifies or can be used to contact or locate a specific person. Such personal information data can include demographic data, location-based data, telephone numbers, email addresses, twitter IDs, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data (e.g., health and fitness data may be used) can be used to provide insights into a user's general wellness, or may be used as positive feedback (e.g., fitness-related advice or coaching) to individuals using technology to pursue wellness goals. Accordingly, use of such personal information data enables users to obtain better health outcomes by more providing more useful feedback regarding fitness-related activities. Further, other uses for personal information data that benefit the user are also contemplated by the present disclosure.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of providing insights into a user's general wellness, the present technology can be configured to allow users to select to "opt in" or "opt out" of participation in the collection of personal information data during registration for services or anytime thereafter. In another example, users can select not to provide health and fitness-associated data for providing positive feedback (e.g., fitness-related advice or coaching) to individuals using technology to pursue wellness goals. In yet another example, users can select to limit the length of time health and fitness data is maintained or entirely prohibit the development of a baseline health and fitness profile. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring health and fitness data sharing preferences based on non-personal information data or a bare minimum amount of personal information, such as the content being requested by the device associated with a user, other non-personal information publicly available information.

What is claimed is:

1. A first electronic device, comprising:
a display device;
one or more processors; and
memory storing one or more programs configured to be executed by the one or more processors, the one or more programs including instructions for:
receiving user activity data; and
subsequent to receiving the user activity data and in accordance with a determination that the user activity data satisfies a first set of activity commentary display criteria, displaying, via the display device, a first user interface, including:
in accordance with a determination that a value of a user characteristic satisfies a set of first commentary criteria; a first activity commentary based on the user activity, data, wherein the first activity commentary includes a first amount of characters, and wherein the first activity commentary does not include activity-based instructions; and
in accordance with a determination that the value of the user characteristic satisfies a set of second commentary criteria, a second activity commentary based on the user activity data, the second activity commentary different from the first commentary, wherein the second activity commentary includes a second amount of characters that is greater than the first amount of characters, and wherein the second activity commentary includes the activity-based instructions.

2. The first electronic device of claim 1, wherein the user characteristic is an age of a user associated with the electronic device.

3. The first electronic device of claim 1, wherein the one or more programs further include instructions for:
after displaying the first activity commentary, receiving second user activity data; and
subsequent to receiving the second user activity data:
in accordance with a determination that a second set of activity display criteria is satisfied, the second set of activity display criteria including a criterion that is satisfied when a current time is not within a predetermined period of time, displaying a third activity commentary based on the second user activity data; and
in accordance with a determination that the second set of activity display criteria is not satisfied, forgoing displaying the third activity commentary based on the second user activity data.

4. The first electronic device of claim 1, wherein the first activity commentary:
in accordance with the value of the user characteristic being within a first predetermined range, includes a graphical element based on the user activity data; and
in accordance with the value of the user characteristic not being within the first predetermined range, does not include a graphical element based on the user activity data.

5. The first electronic device of claim 1, wherein the one or more programs further include instructions for:
receiving, from an external device, third user activity data; and
in response to receiving the third user activity data, displaying a first response user interface that includes:
in accordance with a determination that the value of the user characteristic satisfies a set of first response criteria, a first set of one or more response comment affordances that includes a first response comment affordance that, when selected, causes transmission of a first response comment to the external device; and
in accordance with a determination that the value of the user characteristic satisfies a set of second response criteria, a second set of one or more response comment affordances that includes a second response comment affordance that, when selected, causes transmission of a second response comment to the external device, wherein the first set of one or more response comment affordances is different than the second set of one or more response comment affordances.

6. The first electronic device of claim 1, wherein the one or more programs further include instructions for:
prior to receiving the user activity data, receiving the value of the user characteristic via a user input.

7. The first electronic device of claim 1, wherein the value of the user characteristic is selected from the group consisting of age, a highest level education of a user, a standardized test result achieved by the user, an option selected by the user, and any combination thereof.

8. A non-transitory computer-readable storage medium storing one or more programs configured to be executed by one or more processors of a first electronic device that includes a display device, the one or more programs including instructions for:

receiving user activity data; and subsequent to receiving the user activity data and in accordance with a determination that the user activity data satisfies a first set of activity commentary display criteria, displaying, via the display device, a first user interface, including:

in accordance with a determination that a value of a user characteristic satisfies a set of first commentary criteria, a first activity commentary based on the user activity data, wherein the first activity commentary includes a first amount of characters, and wherein the first activity commentary does not include activity-based instructions; and in accordance with a determination that the value of the user characteristic satisfies a set of second commentary criteria, a second activity commentary based on the user activity data, the second activity commentary different from the first commentary, wherein the second activity commentary includes a second amount of characters that is greater than the first amount of characters, and wherein the second activity commentary includes the activity-based instructions.

9. The non-transitory computer-readable storage medium of claim 8, wherein the user characteristic is an age of a user associated with the electronic device.

10. The non-transitory computer-readable storage medium of claim 8; wherein the one or more programs further include instructions for:

after displaying the first activity commentary, receiving second user activity data; and subsequent to receiving the second user activity data:

in accordance with a determination that a second set of activity display criteria is satisfied, the second set of activity display criteria including a criterion that is satisfied when a current time is not within a predetermined period of time, displaying a third activity commentary based on the second user activity data; and in accordance with a determination that the second set of activity display criteria is not satisfied, forgoing displaying the third activity commentary based on the second user activity data.

11. The non-transitory computer-readable storage medium of claim 8, wherein the first activity commentary:

in accordance with the value of the user characteristic being within a first predetermined range, includes a graphical element based on the user activity data; and in accordance with the value of the user characteristic not being within the first predetermined range, does not include a graphical element based on the user activity data.

12. The non-transitory computer-readable storage medium of claim 8, wherein the one or more programs further include instructions for:

receiving, from an external device, third user activity data; and in response to receiving the third user activity data, displaying a first response user interface that includes:

in accordance with a determination that the value of the user characteristic satisfies a set of first response criteria, a first set of one or more response comment affordances that includes a first response comment affordance that, when selected, causes transmission of a first response comment to the external device; and in accordance with a determination that the value of the user characteristic satisfies a set of second response criteria, a second set of one or more response comment affordances that includes a second response comment affordance that, when selected, causes transmission of a second response comment to the external device, wherein the first set of one or more response comment affordances is different than the second set of one or more response comment affordances.

13. The non-transitory computer-readable storage medium of claim 8, wherein the one or more programs further include instructions for:

prior to receiving the user activity data, receiving the value of the user characteristic via a user input.

14. The non-transitory computer-readable storage medium of claim 8, wherein the value of the user characteristic is selected from the group consisting of age, a highest level education of a user, a standardized test result achieved by the user, an option selected by the user, and any combination thereof.

15. A method comprising:

at a first electronic device including a display device:

receiving user activity data; and subsequent to receiving the user activity data and in accordance with a determination that the user activity data satisfies a first set of activity commentary display criteria, displaying, via the display device, a first user interface, including:

in accordance with a determination that a value of a user characteristic satisfies a set of first commentary criteria, a first activity commentary based on the user activity data, wherein the first activity commentary includes a first amount of characters, and wherein the first activity commentary does not include activity-based instructions; and in accordance with a determination that the value of the user characteristic satisfies a set of second commentary criteria, a second activity commentary based on the user activity data, the second activity commentary different from the first commentary, wherein the second activity commentary includes a second amount of characters that is greater than the first amount of characters, and wherein the second activity commentary includes the activity-based instructions.

16. The method of claim 15, wherein the user characteristic is an age of a user associated with the electronic device.

17. The method of claim 15, further comprising:

after displaying the first activity commentary, receiving second user activity data; and subsequent to receiving the second user activity data:

in accordance with a determination that a second set of activity display criteria is satisfied, the second set of activity display criteria including a criterion that is satisfied when a current time is not within a predetermined period of time, displaying a third activity commentary based on the second user activity data; and in accordance with a determination that the second set of activity display criteria is not satisfied, forgoing displaying the third activity commentary based on the second user activity data.

18. The method of claim 15, wherein the first activity commentary:
in accordance with the value of the user characteristic being within a first predetermined range, includes a graphical element based on the user activity data; and
in accordance with the value of the user characteristic not being within the first predetermined range, does not include a graphical element based on the user activity data.

19. The method of claim 14, further comprising:
receiving, from an external device, third user activity data; and
in response to receiving the third user activity data, displaying a first response user interface that includes:
in accordance with a determination that the value of the user characteristic satisfies a set of first response criteria, a first set of one or more response comment affordances that includes a first response comment affordance that, when selected, causes transmission of a first response comment to the external device; and
in accordance with a determination that the value of the user characteristic satisfies a set of second response criteria, a second set of one or more response comment affordances that includes a second response comment affordance that, when selected, causes transmission of a second response comment to the external device, wherein the first set of one or more response comment affordances is different than the second set of one or more response comment affordances.

20. The method of claim 15, further comprising:
prior to receiving the user activity data, receiving the value of the user characteristic via a user input.

21. The method of claim 15, wherein the value of the user characteristic is selected from the group consisting of age, a highest level education of a user, a standardized test result achieved by the user, an option selected by the user, and any combination thereof.

\* \* \* \* \*

UNITED STATES PATENT AND TRADEMARK OFFICE
CERTIFICATE OF CORRECTION

PATENT NO. : 11,277,485 B2
APPLICATION NO. : 16/888629
DATED : March 15, 2022
INVENTOR(S) : Julie A. Arney et al.

It is certified that error appears in the above-identified patent and that said Letters Patent is hereby corrected as shown below:

In the Claims

In Claim 1, at Column 57, Line 53, delete "criteria;" and insert -- criteria, --, therefor.

In Claim 1, at Column 57, Line 54, delete "activity," and insert -- activity --, therefor.

In Claim 10, at Column 59, Line 29, delete "claim 8;" and insert -- claim 8, --, therefor.

In Claim 19, at Column 61, Line 9, delete "claim 14," and insert -- claim 15, --, therefor.

Signed and Sealed this
Thirtieth Day of August, 2022

Katherine Kelly Vidal
*Director of the United States Patent and Trademark Office*